United States Patent
Roybal et al.

(10) Patent No.: US 11,897,932 B2
(45) Date of Patent: *Feb. 13, 2024

(54) RECEPTORS FOR LIGAND-DEPENDENT TRANSCRIPTIONAL REGULATION

(71) Applicant: The Regents of the University of California, Oakland, CA (US)

(72) Inventors: Kole T. Roybal, San Francisco, CA (US); Raymond Liu, San Francisco, CA (US); Iowis Zhu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/217,635

(22) Filed: Mar. 30, 2021

(65) Prior Publication Data

US 2021/0246186 A1 Aug. 12, 2021

Related U.S. Application Data

(63) Continuation of application No. PCT/US2020/052324, filed on Sep. 23, 2020.

(60) Provisional application No. 62/935,024, filed on Nov. 13, 2019, provisional application No. 62/905,248, filed on Sep. 24, 2019.

(51) Int. Cl.
*C07K 14/705* (2006.01)
*A61K 35/17* (2015.01)
*C12N 5/0783* (2010.01)

(52) U.S. Cl.
CPC ............ *C07K 14/705* (2013.01); *A61K 35/17* (2013.01); *C12N 5/0636* (2013.01); *C07K 2319/02* (2013.01); *C07K 2319/03* (2013.01); *C07K 2319/09* (2013.01); *C07K 2319/74* (2013.01)

(58) Field of Classification Search
None
See application file for complete search history.

(56) References Cited

U.S. PATENT DOCUMENTS

| | | |
|---|---|---|
| 2008/0241150 A1 | 10/2008 | Blackow et al. |
| 2017/0233474 A1 | 8/2017 | Lim et al. |
| 2018/0346543 A1 | 12/2018 | Qi et al. |

FOREIGN PATENT DOCUMENTS

| | | | | |
|---|---|---|---|---|
| WO | WO-2017095823 A1 | * | 6/2017 | ......... A61K 47/6803 |
| WO | WO-2017/207992 A1 | | 12/2017 | |
| WO | WO-2018039247 A1 | * | 3/2018 | ....... C07K 14/70539 |

OTHER PUBLICATIONS

Hayward et al., Oct. 2018, BioRxiv preprint, pp. 1-45.*
Altschul, S.F. et al. (Oct. 5, 1990). "Basic local alignment search tool," *J Mol Biol* 215(3):403-410.
Devereux, J. et al. (Jan. 11, 1984). "A comprehensive set of sequence analysis programs for the VAX," *Nucleic Acids Res.* 12(Pt 1):387-395.
Dudani, J.S. et al. (2018). "Harnessing Protease Activity to Improve Cancer Care," *Annu. Rev. Cancer Biol.* 2:353-376.
Frankel, M.E. et al. "The rapid determination of binding constants for antiviral antibodies by a radioimmunoassay. An analysis of the interaction between hybridoma proteins and influenza virus," *Mol Immunol* 16(2):101-106.
Gordon, W.R. et al. (Jun. 22, 2015, e-published Jun. 4, 2015). "Mechanical Allostery: Evidence for a Force Requirement in the Proteolytic Activation of Notch," *Dev Cell* 33(6):729-736.
Gordon, W.R. et al. (Oct. 1, 2008). "The molecular logic of Notch signaling—a structural and biochemical perspective," *J Cell Sci* 121(Pt 19):3109-3119.
International Search Report dated Dec. 15, 2020 for PCT Application No. PCT/US2020/052324, 3 pages.
McCaffrey, A.P. et al. (Jul. 4, 2002). "RNA interference in adult mice," *Nature* 418(6893):38-39.
Morsut, L. et al. (Feb. 11, 2016, e-published Jan. 28, 2016). "Engineering Customized Cell Sensing and Response Behaviors Using Synthetic Notch Receptors," *Cell* 164(4):780-791.
Naso, M.F. et al. (Aug. 2017). "Adeno-Associated Virus (AAV) as a Vector for Gene Therapy," *BioDrugs* 31(4):317-334.
Nasri, M. et al. (Dec. 2014, e-published Mar. 6, 2014). "Production, purification and titration of a lentivirus-based vector for gene delivery purposes," *Cytotechnology* 66(6):1031-1038.
Porter, D.L. et al. (Aug. 25, 2011, e-published Aug. 10, 2011). "Chimeric antigen receptor-modified T cells in chronic lymphoid leukemia," *N. Engl J Med.* 365(8): 725-733.
Putnam, D.A. (Jan. 15, 1996). "Antisense strategies and therapeutic applications," *Am. J. Health Syst. Pharm.* 53(2):151-160, erratum at *Am. J. Health Syst. Pharm.* 53:325.

(Continued)

*Primary Examiner* — Amy E Juedes
(74) *Attorney, Agent, or Firm* — Mintz, Levin, Cohn, Ferris, Glovsky and Popeo, P.C.

(57) ABSTRACT

The present disclosure generally relates to, among other things, a new class of receptors engineered to modulate transcriptional regulation in a ligand-dependent manner. Particularly, the new receptors, even though derived from Notch, do not require the Notch negative regulatory regions previously believed to be essential for the functioning of the receptors. The disclosure also provides compositions and methods useful for producing such receptors, nucleic acids encoding same, host cells genetically modified with the nucleic acids, as well as methods for modulating an activity of a cell and/or for the treatment of various health conditions or diseases, such as cancers.

17 Claims, 12 Drawing Sheets

Specification includes a Sequence Listing.

(56) References Cited

OTHER PUBLICATIONS

Roybal, K.T. et al. (Oct. 6, 2016, e-published Sep. 29, 2016). "Engineering T Cells with Customized Therapeutic Response Programs Using Synthetic Notch Receptors," *Cell* 167(2):419-432.

Roybal, K.T. et al. (Feb. 11, 2016, e-published Jan. 28, 2016). "Precision Tumor Recognition by T Cells With Combinatorial Antigen-Sensing Circuits," *Cell* 164(4):770-779.

Sakuma, T. et al. (May 1, 2012). "Lentiviral vectors: basic to translational," *Biochem J.* 443(3):603-618.

Samulski, R.J. et al. (Nov. 2014). "AAV-Mediated Gene Therapy for Research and Therapeutic Purposes," *Annu Rev Virol* 1(1):427-451.

Watson, D.J. et al. (2003). Lentiviral Vectors for Gene Transfer to the Central Nervous System. *Viral vectors for Gene Therapy: Methods and Protocols.* Totowa, NJ, USA: Humana Press, pp. 383-404.

Written Opinion dated Dec. 15, 2020 for PCT Application No. PCT/US2020/052324, 5 pages.

Xia, H. et al. (Oct. 2002, e-published Sep. 16, 2002). "siRNA-mediated gene silencing in vitro and in vivo," *Nat Biotechnol* 20(10):1006-1010.

Zhang, X. et al. (Dec. 11, 2014). "The γ-secretase complex: from structure to function," *Frontiers Cell Neurosci* 8:427.

Deatherage, C.L. et al. (Apr. 12, 2017). "Structural and biochemical differences between the Notch and the amyloid precursor protein transmembrane domains," *Sci Adv* 3(4):e1602794.

Sulis, M.L. et al. (Aug. 1, 2008, e-published Apr. 14, 2008). "NOTCH1 extracellular juxtamembrane expansion mutations in T-ALL," *Blood* 112(3):733-740.

Ashworth, T.D et al. (Dec. 16, 2010, e-published Sep. 17, 2010). "Deletion—based mechanisms of Notch1 activation in T-ALL: key roles for RAG recombinase and a conserved internal translational start site in Notch1," *Blood* 116(25):5455-5464.

Extended European Search Report dated Sep. 12, 2023, for EP Patent Application No. 20869738.3, 12 pages.

Gordon, W.R. et al. (Apr. 2007). "Structural basis for autoinhibition of Notch," *Nature Structural* 14(4):295-300.

Sakamoto, K. et al. (Jan. 15, 2005). "Distinct roles of EGF repeats for the Notch signaling system," *Experimental Cell Research* 302(2):281-291.

Sanchez-Irizarry, C. et al. (Nov. 2004). "Notch subunit heterodimerization and prevention of ligand-independent proteolytic activation depend, respectively, on a novel domain and the LNR repeats," *Molecular and Cellular Biology* 24(21):9265-9273.

Zhu, I. et al. (May 23, 2021). "Design and modular assembly of synthetic intramembrane proteolysis receptors for custom gene regulation in therapeutic cells," *bioRxiv* 25 pages.

Zhu, I. et al. (Apr. 14, 2022). "Modular design of synthetic receptors for programmed gene regulation in cell therapies," *Cell* 185(8):1431-1443.

* cited by examiner

RECEPTORS FOR LIGAND-DEPENDENT TRANSCRIPTIONAL REGULATION

CROSS-REFERENCE TO RELATED APPLICATIONS

This application is a continuation of International Patent Application No. PCT/US2020/052324 filed on Sep. 23, 2020, which claims the benefit of priority to U.S. Provisional Patent Application No. 62/905,248, filed Sep. 24, 2019, and U.S. Provisional Patent Application No. 62/935,024, filed Nov. 13, 2019, the disclosures of which are incorporated by reference herein in their entireties, including any drawings.

STATEMENT REGARDING FEDERALLY SPONSORED R&D

This invention was made with government support under grant no. OD025751 awarded by The National Institutes of Health. The government has certain rights in the invention.

INCORPORATION OF THE SEQUENCE LISTING

This application contains a Sequence Listing which is hereby incorporated by reference in its entirety. The accompanying Sequence Listing text file, named "Sequence Listing_048536-649C01US_ST25.txt," was created on Sep. 23, 2020 and is 92 KB.

FIELD

The present disclosure relates generally to new synthetic cellular receptors that bind cell-surface ligands and have selectable specificities and activities. The disclosure also provides compositions and methods useful for producing such receptors, nucleic acids encoding same, host cells genetically modified with the nucleic acids, as well as methods for modulating an activity of a cell and/or for the treatment of various health conditions or diseases, such as cancers.

BACKGROUND

An important problem limiting the development of engineered cell therapies in humans is the regulation of therapeutic gene expression to reduce or eliminate interactions causing significant side effects on administration of chimeric antigen receptor T cells (CAR-T) such as, for example, off-target activity, on-target/off-tumor activity (i.e., wherein the CAR-T target is also found on normal cells outside the tumor), and inability to modulate or turn off CAR-T activity when needed. A possible solution to these problems is to use an alternative synthetic receptor that is capable of modifying gene expression and/or cellular behavior.

Notch receptors are transmembrane proteins that mediate cell-cell contact signaling and play a central role in development and other aspects of cell-to-cell communication, e.g. communication between two contacting cells, in which one contacting cell is a "receiver" cell and the other contacting cell is a "sender" cell. Notch receptors expressed in a receiver cell recognize their ligands (e.g., the delta/serrate/lag, or "DSL" family of proteins), expressed on a sending cell. The engagement of notch and delta on these contacting cells leads to two-step proteolysis of the notch receptor that ultimately causes the release of the intracellular portion of the receptor from the membrane into the cytoplasm. Notch has a metalloprotease cleavage site (denoted "S2"), which is normally protected from cleavage by the Notch negative regulatory region (NRR), a domain consisting of three LIN-12-Notch repeat (LNR) modules and a heterodimerization domain (HD). It is believed that this proteolysis is regulated by the force exerted by the sending cell: the DSL ligand pulls on the Notch receptor, and changes the conformation of the NRR, exposing the metalloprotease site. That site is then cleaved by a constitutively active protease, releasing the extracellular binding portion and negative regulatory region of the receptor. Release of the ligand-binding portion of the receptor in turn exposes another cleavage site(s) (denoted "S3"), which is cleaved by gamma secretase within the cell membrane to release the nuclear homing intracellular domain from the cell membrane. W. R. Gordon et al., *Dev Cell* (2015) 33:729-36. This released domain alters receiver cell behavior by functioning as a transcriptional regulator. Notch receptors are involved in and required for a variety of cellular functions during development and are important for the function of a vast number of cell-types across species.

Examples of existing first-generation synthetic derivatives of Notch receptors, which are often referred to as "SynNotch receptors", exploit this straightforward signaling behavior by replacing the extracellular ligand-binding domain, which in wild-type Notch contains multiple EGF-like repeats, with an antibody derivative, and replacing the cytoplasmic domain with a transcription activator of choice, while still relying on the Notch NRR (L. Morsut et al., *Cell* (2016) 164:780-91). Generally, SynNotch signaling correlates with ligand binding, but it is difficult to adjust the sensitivity and response of the receptor. Additionally, the NRR spans approximately 160 amino acids, making this domain alone the size of some mature proteins, such as insulin or epidermal growth factor (EGF). This makes expression of the receptor less efficient and, due to vector capacity-related size constraints, the resulting chimeric receptors can exceed the capacity of some cloning and transfection vectors.

All references and patents cited herein are hereby incorporated by reference in full, as if fully set forth herein.

SUMMARY

The present disclosure provides synthetic chimeric receptors that, surprisingly, function despite the complete absence of the Notch negative regulatory region (NRR). Furthermore, these receptors provide a wide range of sensitivity, including a receptor that is sensitive to the degree of T-cell activation when it is expressed in a T cell. Additionally, by omitting one or more domains of the Notch/SynNotch negative regulatory region, polynucleotides encoding the receptors of the disclosure can be made smaller than SynNotch-encoding polynucleotides, which facilitates the use of vectors having more limited capacity, or the inclusion of additional elements that would otherwise be excluded due vector capacity-related size constraints.

In one aspect, provided herein are chimeric polynucleotides including, from N-terminus to C-terminus: (a) an extracellular ligand-binding domain having a binding affinity for a selected ligand; (b) a linking sequence; (c) a transmembrane domain including one or more ligand-inducible proteolytic cleavage sites; and (d) an intracellular domain including a transcriptional regulator, wherein binding of the selected ligand to the extracellular ligand-binding domain induces cleavage at the ligand-inducible proteolytic cleavage site between the transcriptional regulator and the linking sequence, and wherein the chimeric polypeptide does not include a LIN-12-Notch repeat (LNR) and/or a heterodimerization domain (HD) of a Notch receptor.

Non-limiting exemplary embodiments of the chimeric polypeptides according to the present disclosure include one or more of the following features. In some embodiments, the transmembrane domain further includes a stop-transfer-sequence (STS). In some embodiments, the extracellular domain includes an antigen-binding moiety capable of binding to a ligand on the surface of a cell. In some embodiments, the cell is a pathogen. In some embodiments, the cell is a human cell. In some embodiments, the human cell is a tumor cell. In some embodiments, the human cell is a terminally differentiated cell. In some embodiments, the ligand comprises a protein or a carbohydrate. In some embodiments, the ligand is selected from the group consisting of CD1, CD1a, CD1b, CD1c, CD1d, CD1e, CD2, CD3d, CD3e, CD3g, CD4, CD5, CD7, CD8a, CD8b, CD19, CD20, CD21, CD22, CD23, CD25, CD27, CD28, CD33, CD34, CD40, CD45, CD48, CD52, CD59, CD66, CD70, CD71, CD72, CD73, CD79A, CD79B, CD80 (B7.1), CD86 (B7.2), CD94, CD95, CD134, CD140 (PDGFR4), CD152, CD154, CD158, CD178, CD181 (CXCR1), CD182 (CXCR2), CD183 (CXCR3), CD210, CD246, CD252, CD253, CD261, CD262, CD273 (PD-L2), CD274 (PD-L1), CD276 (B7H3), CD279, CD295, CD339 (JAG1), CD340 (HER2), EGFR, FGFR2, CEA, AFP, CA125, MUC-1, MAGE, BCMA (CD269), ALPPL2, GFP, eGFP, and SIRPα.

In another aspect, provided herein are recombinant cells including (a) a chimeric polypeptide as disclosed herein and/or (b) a recombinant nucleic acid as disclosed herein. Also provided, in a related aspect, are cell cultures including at least one recombinant cell as disclosed herein and a culture medium.

In another aspect, provided herein are pharmaceutical compositions including a pharmaceutical acceptable carrier and one or more of the following: (a) a recombinant nucleic acid as disclosed herein, and (b) a recombinant cell as disclosed herein. In some embodiments, the disclosed pharmaceutical composition includes a recombinant nucleic acid as disclosed herein and a pharmaceutically acceptable carrier. In some embodiments, the recombinant nucleic acid is encapsulated in a viral capsid or a lipid nanoparticle.

In another aspect, provided herein are methods for modulating an activity of a cell, including (a) providing a recombinant cell of the disclosure, and (b) contacting it with a selected ligand, wherein binding of the selected ligand to the extracellular ligand-binding domain induces cleavage of a ligand-inducible proteolytic cleavage site and releases the transcriptional regulator, wherein the released transcriptional regulator modulates (e.g., inhibits or induces) an activity of the recombinant cell. Another aspect relates to methods for modulating an activity of a target cell in an individual, including administering to the individual an effective number of the recombinant cells of the disclosure, wherein the recombinant cells modulate (e.g., inhibit or induce) an activity of the target cell in the individual.

Another aspect relates to methods for treating a health condition (e.g., disease) in an individual, including administering to the individual an effective number of the recombinant cells of the disclosure, wherein the recombinant cells treat the health condition in the individual.

In another aspect, some embodiments of the disclosure relate to systems for modulating an activity of a cell, inhibiting a target cancer cell, or treating a health condition (e.g., disease) in an individual in need thereof, wherein the system includes one or more of: a chimeric polypeptide of the disclosure; a polynucleotide of the disclosure; a recombinant cell of the disclosure; or a pharmaceutical composition of the disclosure.

Another aspect of the disclosure relates to methods for making a recombinant cell of the disclosure, including (a) providing a cell capable of protein expression and (b) contacting the provided cell with a recombinant nucleic acid of the disclosure. In some embodiments, the cell is obtained by leukapheresis performed on a sample obtained from a subject, and the cell is contacted ex vivo. In some embodiments, the recombinant nucleic acid is encapsulated in a viral capsid or a lipid nanoparticle.

Yet another aspect of the disclosure is the use of one or more of: a chimeric polypeptide of the disclosure; a polynucleotide of the disclosure; a recombinant cell of the disclosure; or a pharmaceutical composition of the disclosure; for the treatment of a health condition (e.g., disease). In some embodiments, the health condition is a disease (e.g., cancer).

Another aspect of the disclosure is the use of one or more of: a chimeric polypeptide of the disclosure; a polynucleotide of the disclosure; a recombinant cell of the disclosure; or a pharmaceutical composition of the disclosure; for the manufacture of a medicament for the treatment of a disease.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A depicts the schematic structure of an existing synthetic Notch receptor (SynNotch), which includes an extracellular ligand-binding domain (anti-CD19 scFv), a regulatory region, a juxtamembrane region (JMD), transmembrane domain (TMD), a stop transfer sequence (STS), and a transcriptional regulator (TF). This exemplary SynNotch possesses the Notch negative regulatory region (NRR) as a regulatory region, with the JMD, TMD, and STS all from Notch1. FIG. 1B depicts the schematic structure of an exemplary second-generation synthetic Notch receptor as disclosed herein (miniNotch receptor). Compared to SynNotch receptor, the miniNotch receptor does not have an NRR.

FIG. 2A depicts schematics of a SynNotch1 receptor (left panel) and a miniNotch receptor (right panel). FIG. 2B depicts exemplary flow cytometry data of receptor expression demonstrating that MiniNotch receptors are expressed in human CD4+ T-cells. FIG. 2C depicts TCR activation by the MiniNotch receptors. The top panel summarizes the results of a receptor activation testing without TCR activation. $1\times10^5$ double positive T-cells expressing anti-CD19 receptors were co-cultured with: $1\times10^5$ K562 cells (blue) or $1\times10^5$ CD19+K562 cells (red) for 24 hours. Transcriptional activation of an inducible BFP reporter gene was subsequently measured using a Fortessa X-50 (BD Biosciences). The bottom panel summarizes the results of a receptor activation with TCR activation.

In this experiment, phorbol 12-myristate 13-acetate (PMA), a DAG analog, was added to co-cultures to simulate PKC signaling).

Figure 3:
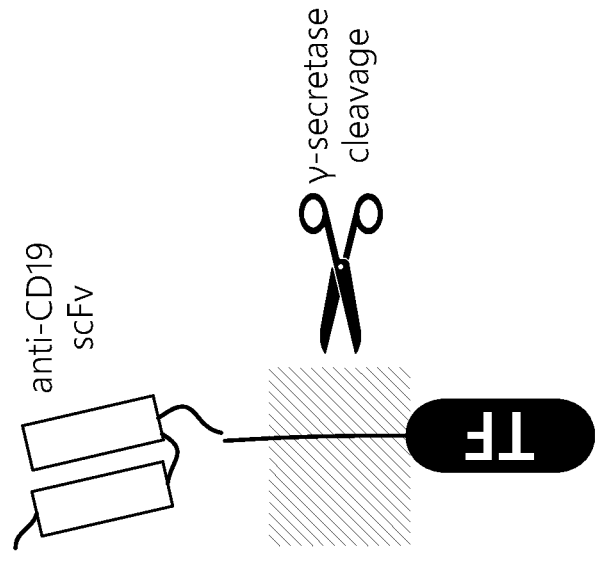
Figure 3:
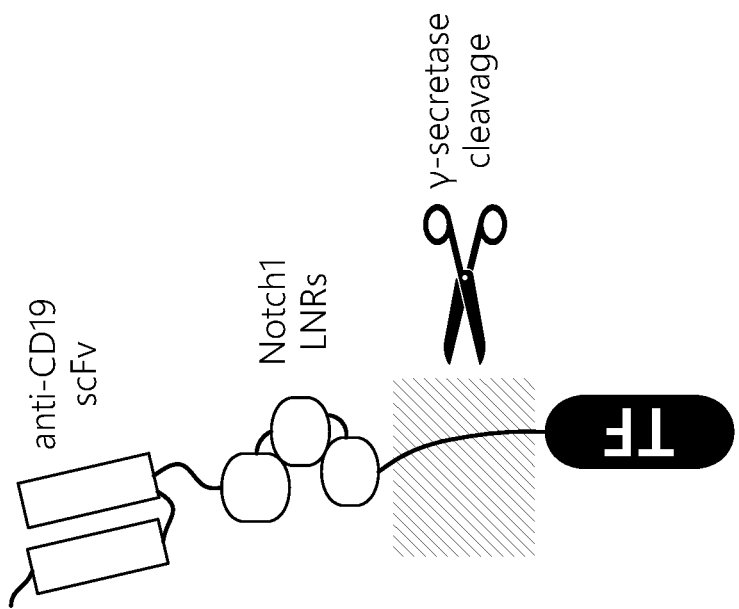
Figure 3:
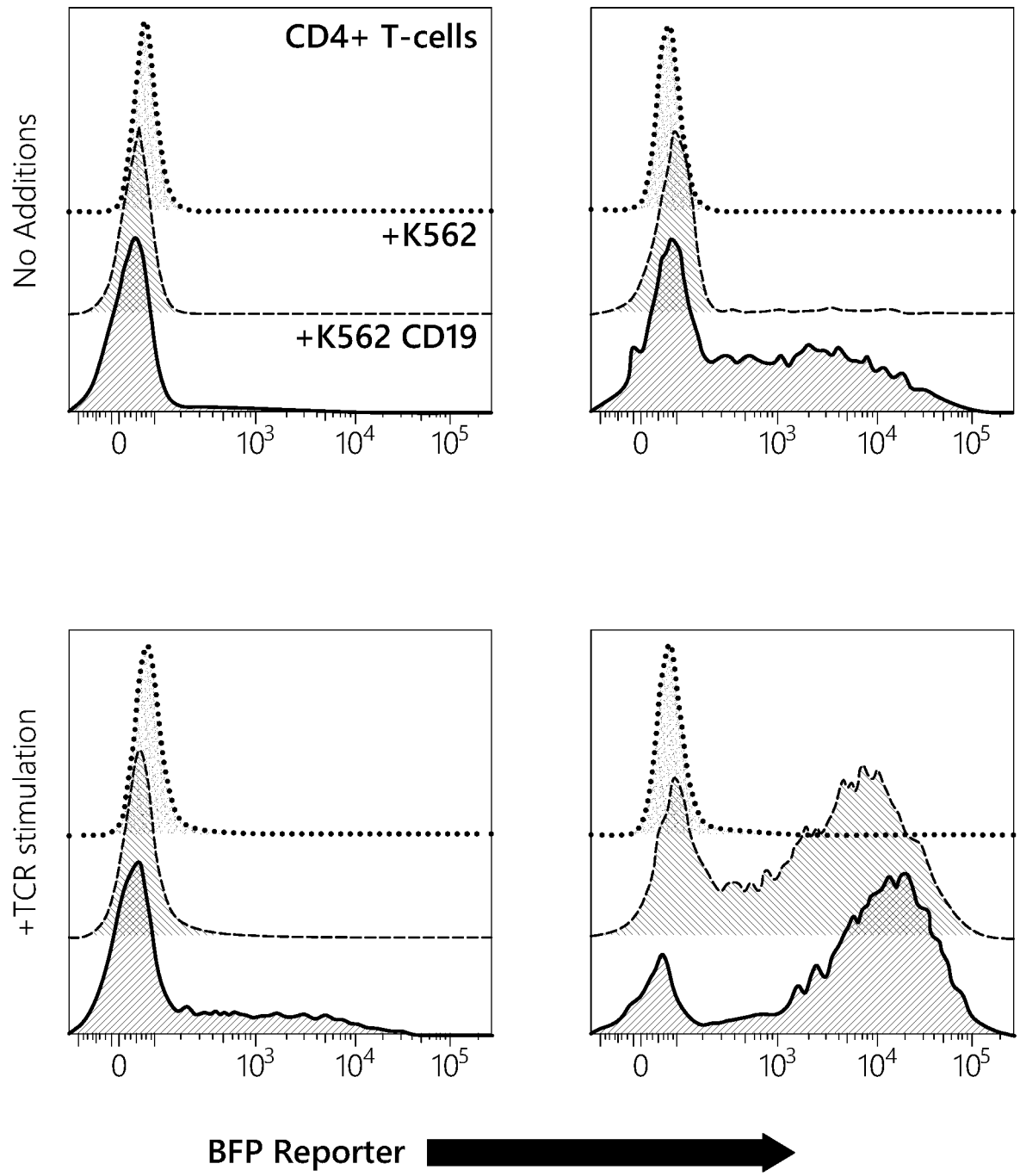

FIG. 3 schematically summarizes the results of experiments where the activation testing of SynNotch and MiniNotch receptor was conducted with concurrent T-cell activation to assess, e.g., TCR signaling. In these experiments, to simulate T-cell activation, anti-MCAM, anti-CD3 Bispecific T-cell Engagers (MCAM BiTEs) were used, which activate the T-cell receptor in the presence of K562 cells.

Figure 4A:
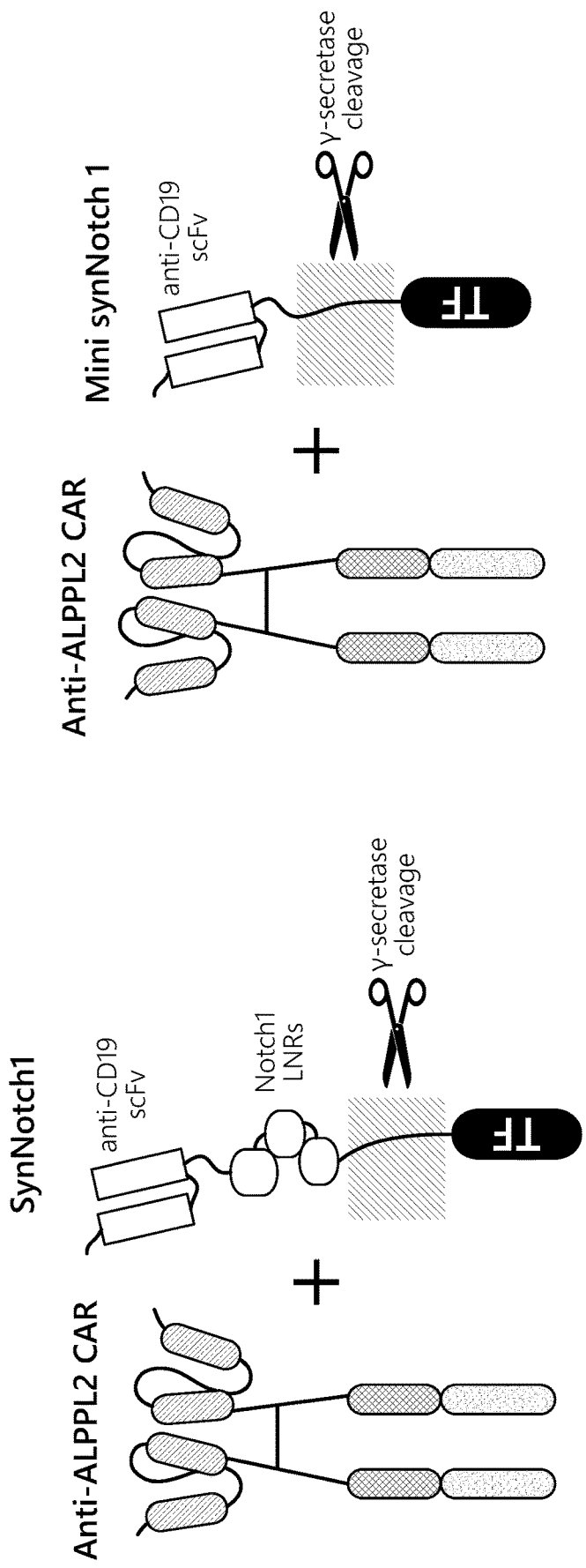
Figure 4B:
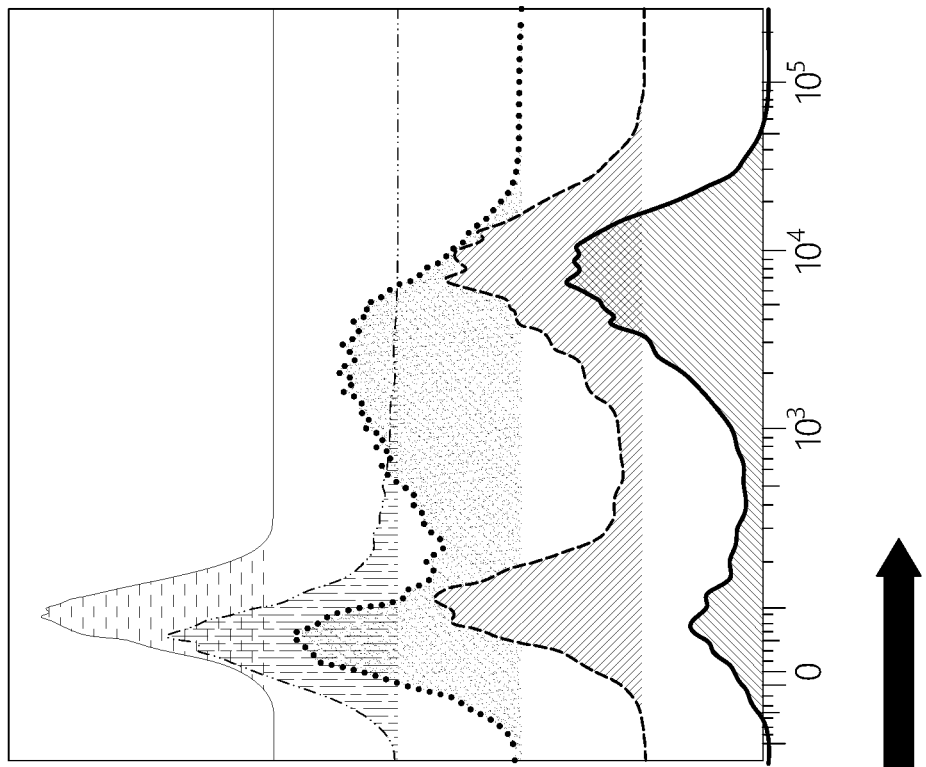
Figure 4B:
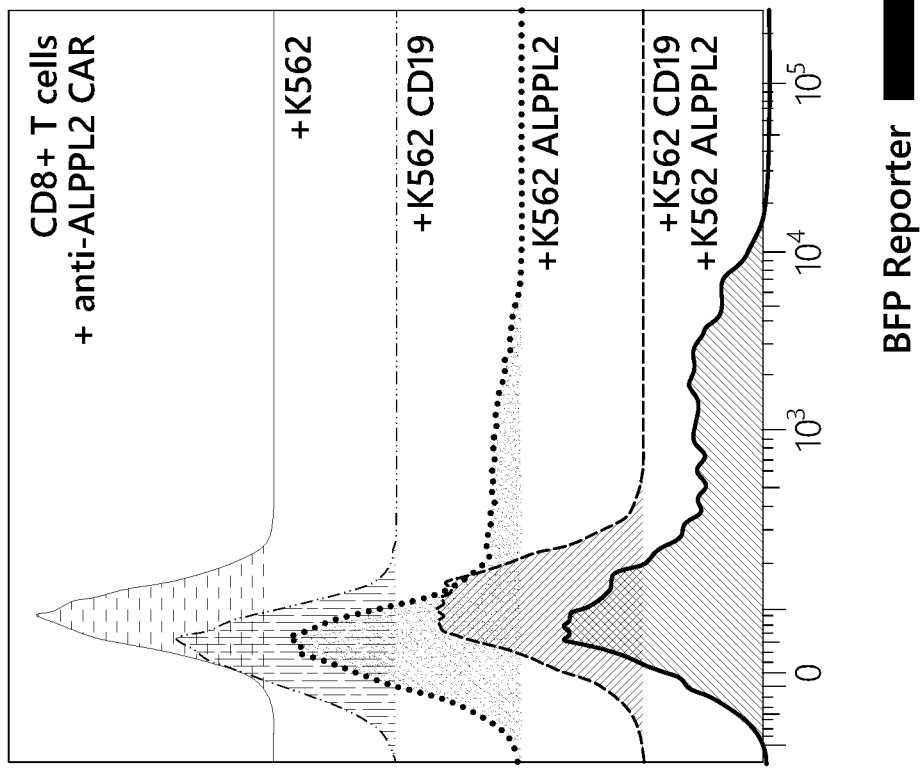

FIGS. 4A-4B schematically summarize the results of experiments where the activation testing of SynNotch and MiniNotch receptor was conducted with co-expressed CAR to assess, e.g., CAR signaling enhancement. In these experiments, SynNotch1 and miniNotch1 were co-transduced with a CAR targeting ALPPL2. As shown in FIG. 4B, $1\times10^5$ double positive T-cells expressing anti-CD19 SynNotch or miniNotch and anti-ALPPL2 CARs were co-cultured with: blank sample (top trace), $1\times10^5$ K562 cells (second trace from top), $1\times10^5$ CD19+K562 cells (third trace from top), $1\times10^5$ ALPPL2+K562 cells (fourth trace from top), or $1\times10^5$ CD19+K562 cells and $1\times10^5$ ALPPL2+K562 cells (bottom trace) for 24 hours. Transcriptional activation of an inducible BFP reporter gene was subsequently measured using a Fortessa X-50 (BD Biosciences).

Figure 5A:
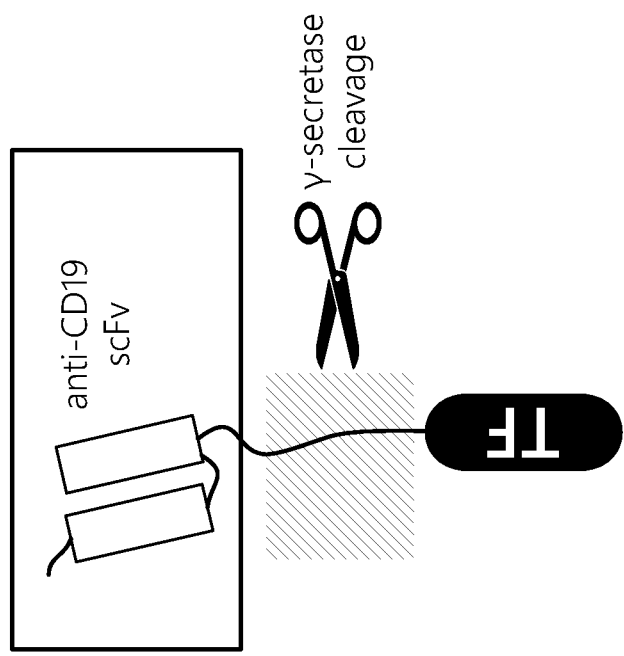
Figure 5B:
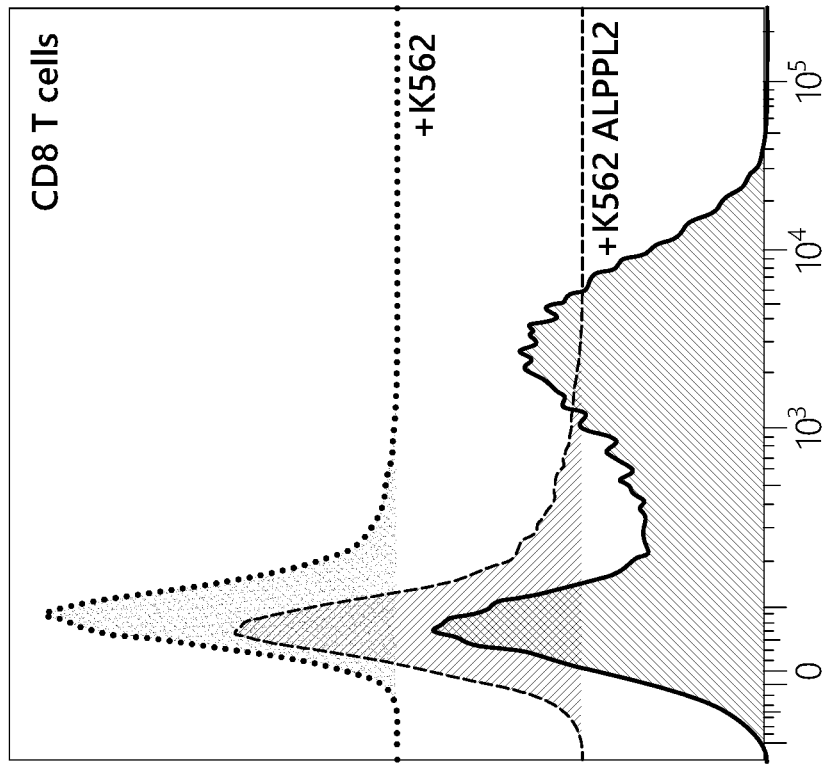
Figure 5B:
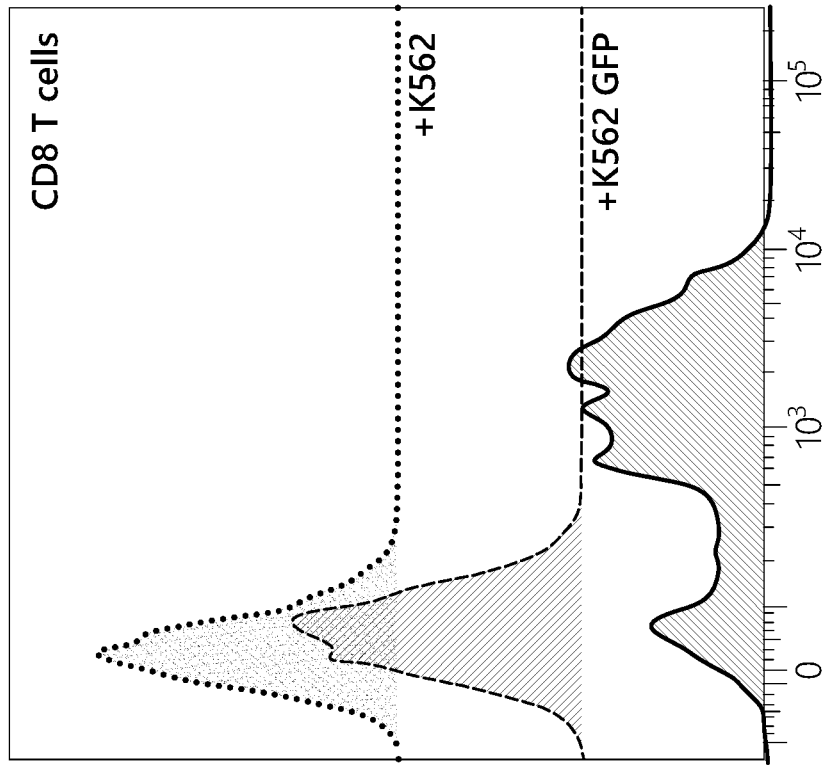

FIGS. 5A-5B schematically summarize the results of experiments to test miniNotch receptors, exemplified by miniNotch1, with other ligand recognition domains. In addition to the anti-CD19 scFv, the anti-GFP LaG17 nanobody and the anti-ALPPL2 scFv were also used. FIG. 5B shows activation testing with additional ligand recognition domains. In these experiments, primary CD8 human T-cells were activated with anti-CD$3^3$/anti-CD28 Dynabeads (Gibco) and transduced with two lentiviral constructs expressing either a Notch receptor or a transcriptional reporter construct.

Figure 6A:
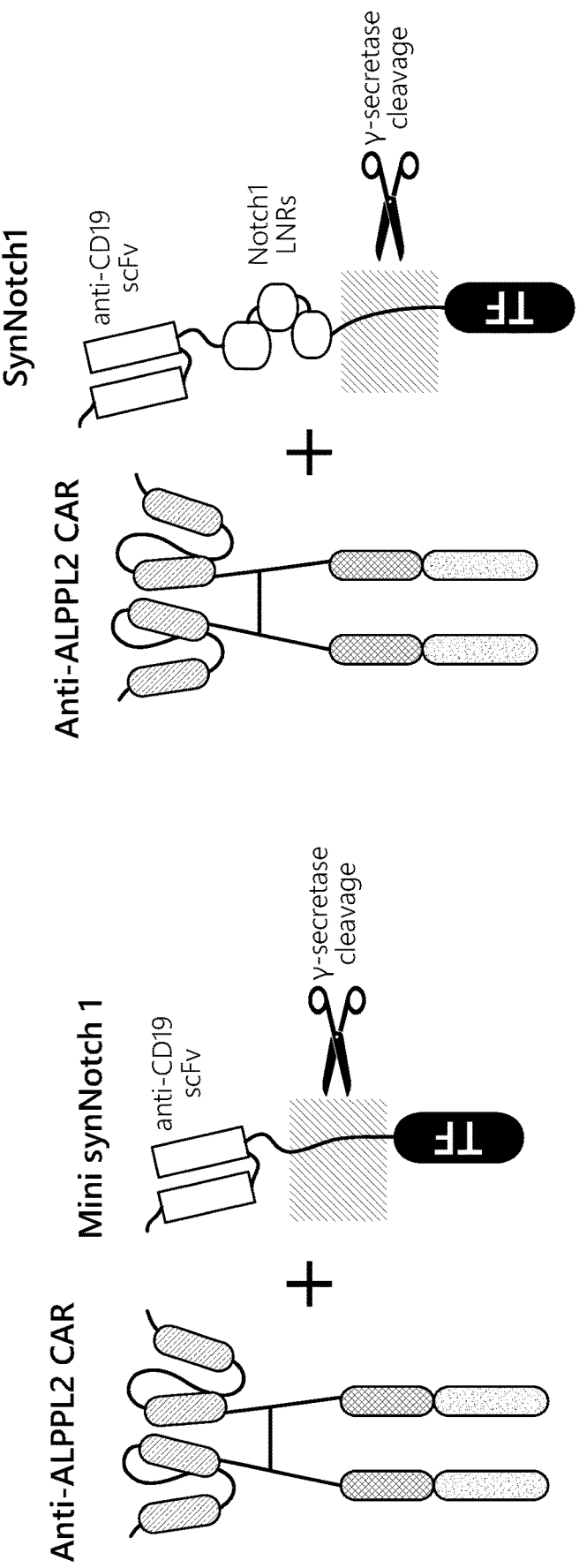
Figure 6B:
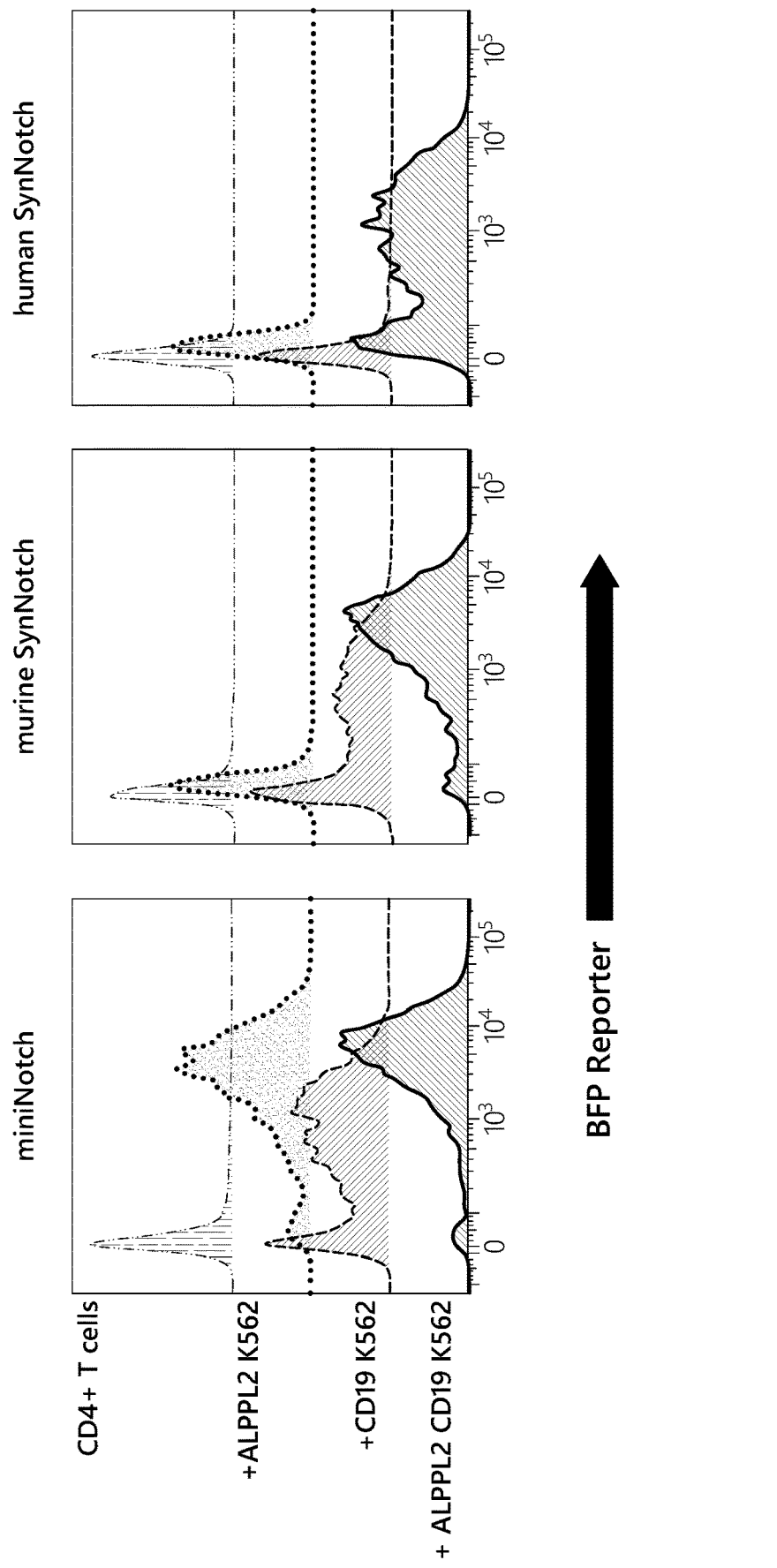

FIGS. 6A-6B schematically summarize the results of experiments performed to assess miniNotch receptor activation with co-expressed CAR, as exemplified by miniNotch1. FIG. 6A shows diagrams for activating an exemplary Mini Notch receptor ("Mini synNotch1") vs. a SynNotch1 receptor by a co-expressed CAR targeting ALPPL2. As shown in FIG. 6B, CD4+ T-cells expressing either one of three anti-CD19 Notch constructs (mini Notch, first-generation murine SynNotch, and first-generation human SynNotch; referring to the three panels from left to right) were co-cultured with negative control (with nothing added; top trace), ALPPL2-expressing K562 cells (second trace from top), CD19-expressing K562 cells (third trace from top), or K562 cells expressing both ALPPL2 and CD19 (bottom trace) for 24 hours. Transcriptional activation of an inducible BFP reporter gene was subsequently measured using a Fortessa X-50 (BD Biosciences).

DETAILED DESCRIPTION OF THE DISCLOSURE

The present disclosure generally relates to, among other things, a new class of engineered chimeric polypeptide receptors, which modulate transcriptional regulation in a ligand-dependent manner. Particularly, the new receptors (termed "miniNotch"), even though derived from Notch, do not require the Notch negative regulatory regions (NRR) previously believed to be essential for the functioning of the receptors. This new class of receptors is synthetic and recombinant, and does not occur in nature. In some embodiments, the non-naturally occurring receptors disclosed herein bind a target cell-surface ligand, which triggers proteolytic cleavage of the receptors and release of a transcriptional regulator that modulates a custom transcriptional program in the cell. The disclosure also provides compositions and methods useful for producing such receptors, nucleic acids encoding same, host cells genetically modified with the nucleic acids, as well as methods for modulating an activity of a cell and/or for the treatment of various conditions or diseases, such as cancers.

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Definitions

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

The terms "administration" and "administering", as used herein, refer to the delivery of a composition or formulation by an administration route including, but not limited to, intravenous, intra-arterial, intracranial, intramuscular, intraperitoneal, subcutaneous, intramuscular, and topical administration, or combinations thereof. The term includes, but is not limited to, administration by a medical professional and self-administration.

"Cancer" refers to the presence of cells possessing characteristics typical of cancer-causing cells, such as uncontrolled proliferation, immortality, metastatic potential, rapid growth and proliferation rate, and certain characteristic morphological features. Some types of cancer cells can aggregate into a mass, such as a tumor, but some cancer cells can exist alone within a subject. A tumor can be a solid tumor, a soft tissue tumor, or a metastatic lesion. As used herein, the term "cancer" also encompass other types of non-tumor cancers. Non-limiting examples include blood cancers or hematological malignancies, such as leukemia, lymphoma, and myeloma. Cancers can include premalignant, as well as malignant cancers.

The terms "host cell" and "recombinant cell" are used interchangeably herein. It is understood that such terms, as well as "cell", "cell culture", "cell line", refer not only to the particular subject cell or cell line but also to the progeny or potential progeny of such a cell or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences, such that progeny may not, in fact, be identical to the parent cell, but are still included within the scope of the term as used herein.

The term "operably linked"," as used herein, denotes a physical or functional linkage between two or more elements, e.g., polypeptide sequences or polynucleotide sequences, which permits them to operate in their intended fashion.

The term "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated over a region that is at least about 20 amino acids or nucleotides in length, or over a region that is 10-100 amino acids or nucleotides in length, or over the entire length of a given sequence. Sequence identity can be calculated using published techniques and widely available computer programs, such as the GCS program package (Devereux et al, Nucleic Acids Res. 12:387, 1984), BLASTP, BLASTN, FASTA (Atschul et al., *J Mol Biol* 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

As used herein, and unless otherwise specified, a "therapeutically effective amount" of an agent is an amount sufficient to provide a therapeutic benefit in the treatment or management of a health condition such as a disease (e.g., a cancer), or to delay or minimize one or more symptoms associated with the disease. A therapeutically effective amount of a compound means an amount of therapeutic agent, alone or in combination with other therapeutic agents, which provides a therapeutic benefit in the treatment or management of the disease. The term "therapeutically effective amount" can encompass an amount that improves overall therapy of the disease, reduces or avoids symptoms or causes of the disease, or enhances the therapeutic efficacy of another therapeutic agent. An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition including a "therapeutically effective amount" will depend on the purpose of the treatment, and will be ascertainable by one skilled in the art using known techniques (see, e.g., Lieberman, *Pharmaceutical Dosage Forms* (vols. 1-3, 2010); Lloyd, *The Art, Science and Technology of Pharmaceutical Compounding* (2016); Pickar, *Dosage Calculations* (2012); and *Remington: The Science and Practice of Pharmacy*, 22nd Edition, 2012, Gennaro, Ed., Lippincott, Williams & Wilkins).

As used herein, a "subject" or an "individual" includes animals, such as human (e.g., human individuals) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Notch Receptors

Notch receptors are large transmembrane proteins that normally communicate signals upon binding to surface-bound ligands expressed on adjacent cells. Notch signals rely on cell-cell contact. Evolutionary divergence of vertebrates and invertebrates has been accompanied by at least two rounds of gene duplication: flies possess a single Notch gene, worms two (GLP-1 and LIN-12), and mammals four (NOTCH1-4). Transduction of Notch signals relies on three key events: (i) ligand recognition; (ii) conformational exposure of the ligand-dependent cleavage site; and (iii) assembly of nuclear transcriptional activation complexes.

Canonical Notch signals are transduced by a process called regulated intramembrane proteolysis. Notch receptors are normally maintained in a resting, proteolytically resistant conformation on the cell surface, but ligand binding initiates a proteolytic cascade that releases the intracellular portion of the receptor (ICN) from the membrane. The critical, regulated cleavage step is effected by ADAM metalloproteases and occurs at a site called S2 immediately external to the plasma membrane. This truncated receptor, dubbed NEXT (for Notch extracellular truncation), remains membrane tethered until it is processed at site S3 by gamma secretase, a multiprotein enzyme complex.

After gamma secretase-mediated cleavage, the ICN ultimately enters the nucleus, where it assembles a transcriptional activation complex that contains a DNA-binding transcription factor called CSL, and a transcriptional coactivator of the Mastermind family. This complex then engages additional coactivator proteins such as p300 to recruit the basal transcription machinery and activate the expression of downstream target genes.

As discussed in greater detail below, Notch receptors have a modular domain organization. The Notch extracellular subunit (NEC) of Notch receptors consist of a series of N-terminal epidermal growth factor receptor (EGFR)-like repeats that are responsible for ligand binding. O-linked glycosylation of these EGFR repeats, including modification by O-fucose, Fringe, and Rumi glycosyltransferases, also modulates the activity of Notch receptors in response to different ligand subtypes in flies and mammals.

The EGFR repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage, so that its N-terminal part (HD-N) terminates the NEC, and its C-terminal half (HD-C) constitutes the beginning of the Notch transmembrane subunit (NTM) subunit. Following the extracellular HD-C region of the NEC is a transmembrane segment and an intracellular region (ICN), which includes a RAM domain (RBP-Jκ associated molecule, which is originally denoted the "RAM23" domain), seven ankyrin (ANK) repeats flanked by two nuclear localization signals (NLS), a transactivation domain (TAD), and a PEST region that is rich in proline (P), glutamic acid (E), serine (S), and threonine (T), and participates in protein degradation. Additional information regarding Notch receptors and Notch-mediated cell signaling can be found in, for example, W. R. Gordon et al., *Dev Cell* (2015) 33:729-36 and W. R. Gordon et al., *J. Cell Sci.* (2008) 121:3109-19, both of which are hereby incorporated by reference.

Compositions of the Disclosure

As described in greater detail below, the present disclosure provides a new class of chimeric polypeptide receptors engineered to modulate transcriptional regulation in a ligand-dependent manner with various advantages over existing synthetic Notch receptors. Particularly, the new receptors, even though derived from Notch, do not require the Notch negative regulatory regions (NRR) previously believed to be essential for the functioning of the receptors.

One skilled in the art will understand that the chimeric polypeptide receptors disclosed herein facilitate amplified activation under certain cellular and environmental contexts. For example, the results of experiments described in Example 4 have demonstrated that the level of activation (e.g., amount of transcriptional output) increases with PKC signaling by treatments with Phorbol-12-Myristate-13-Acetate (PMA) or T-cell activation (e.g., stimulation of the TCR). In particular, the fraction of cells that activate transcription was increased and the level of transcription was increased with certain receptor designs such as Mini synNotch1 (see, e.g., FIG. 2C, bottom panel). This type of feedback on the receptor activity is a new feature that can be exploited to enhance and tune the production of therapeutic payloads by engineered cells. Furthermore, as described in greater detail below, a number of the receptor variants disclosed herein are easier to express than existing SynNotch receptors, as they can be transduced at higher efficiencies and are expressed at higher levels on the cell surface of human primary T cells.

In addition, as described in greater detail below, certain chimeric receptors of the disclosure provide a range of sensitivity, including receptors that are sensitive to the degree of T-cell activation when it is expressed in a T cell. Certain receptors described herein provide both a higher signal level and a wider range of sensitivity. They also provide a range of trade-offs between signal level and noise level (e.g., signal level in the absence of ligand). Additionally, since natural Notch receptors are large with the NEC subunit containing several dozen tandem EGFR-like repeats, by omitting the Notch regulatory regions, or even the entire NEC subunit, polynucleotides encoding the receptors of the disclosure can be made smaller than natural Notch receptors and existing SynNotch-encoding polynucleotides, which facilitates the use of vectors having more limited capacity, or the inclusion of additional elements that would otherwise be excluded by vector capacity-related size constraints.

As described in greater detail below, certain chimeric polypeptide receptors disclosed herein have better activity than existing SynNotch receptors as determined by, e.g., ligand-induced signal levels of a desired transcriptional output, and provide a more modular platform for engineering additional Notch receptors. This modular platform facilitates domains with distinct functions to be easily swapped with corresponding domains from, e.g., other species, enabling customization of receptors activation profile. As described in greater detail in the Examples, miniNotch receptors as provided herein can be customized to a vast degree, with all elements of the receptor extracellular, transmembrane, and intracellular domains available for customization. For example, the testing of miniNotch receptors derived from the four human Notch variants (Notch1-4) demonstrated that all four have different signaling characteristics (e.g. level of activation, sensitivity to T-cell activation). Without being bound to any particular theory, it is believed that the miniNotch receptors described herein can provide higher levels of ligand-induced signal when compared to either murine or human versions of SynNotch1. Existing SynNotch receptors can be engineered with ligand-binding domains such scFvs and nanobodies, but it has been difficult to use natural extracellular domains from receptors/ ligands on SynNotch receptors. In contrast, a number of the second-generation Notch receptors disclosed herein are be amenable to other types of ligand binding domains, thus expanding the landscape of targetable diseases and tissues. For example, compared to existing human SynNotch1, which often expresses and activates poorly, certain miniNotch1 receptors as described herein have demonstrated the ability to accept a wider subset scFvs.

As described in Examples 4-7, certain new chimeric polypeptide receptors have been tested and validated in primary human T cells. These new receptors are expected to show similar performance in mouse models. The receptors disclosed herein may be engineered into various immune cell types for enhanced discrimination and elimination of tumors, or in engineered cells for control of autoimmunity and tissue regeneration. Accordingly, engineered cells, such as immune cells engineered to express one of more of the chimeric receptors disclosed herein, are also within the scope of the disclosure.

Chimeric Polypeptides

This disclosure provides novel, non-naturally occurring recombinant chimeric polypeptides engineered to modulate transcriptional regulation in a ligand-dependent manner. In particular, the new receptors, even though derived from Notch, do not require the Notch regulatory region (NRR) previously believed to be essential for the functioning of the receptors. In some embodiments, the engineered receptors disclosed herein bind a target cell-surface displayed ligand, which triggers proteolytic cleavage of the receptors and release of a transcriptional regulator that modulates a custom transcriptional program in the cell.

In some embodiments, provided herein is a chimeric polypeptide including, from N-terminus to C-terminus: (a) an extracellular ligand-binding domain (ECD) having a binding affinity for a selected ligand; (b) a linking sequence (JMD, juxtamembrane domain); (c) a transmembrane domain (TMD) including one or more ligand-inducible proteolytic cleavage sites; and (d) an intracellular domain (ICD) including a transcriptional regulator, wherein binding of the selected ligand to the ECD induces cleavage at the ligand-inducible proteolytic cleavage site between the transcriptional regulator and the JMD, and wherein the chimeric polypeptide does not include a LIN-12-Notch repeat (LNR) and/or a heterodimerization domain (HD) of a Notch receptor.

Extracellular Domains (ECD)

In some embodiments, the ECD of the chimeric polypeptides receptors disclosed herein has a binding affinity for one or more target ligands. The target ligand is expressed on a cell surface, or is otherwise anchored, immobilized, or restrained so that it can exert a mechanical force on the chimeric receptor. As such, without being bound to any particular theory, binding of the ECD of a chimeric receptor provided herein to a cell-surface ligand does not necessarily remove the target ligand from the target cell surface, but instead enacts a mechanical pulling force on the chimeric receptor. For example, an otherwise soluble ligand may be targeted if it is bound to a surface, or to a molecule in the extracellular matrix. In some embodiments, the target ligand is a cell-surface ligand. Non-limiting examples of suitable ligand types include cell surface receptors; adhesion proteins; carbohydrates, lipids, glycolipids, lipoproteins, and lipopolysaccharides that are surface-bound; integrins; mucins; and lectins. In some embodiments, the ligand is a protein. In some embodiments, the ligand is a carbohydrate.

In some embodiments, the extracellular domain includes the ligand-binding portion of a receptor. In some embodiments, the extracellular domain includes an antigen-binding moiety that binds to one or more target antigens. One skilled in the art upon reading the present disclosure will readily understand that the term "functional fragment thereof" or "functional variant thereof" refers to a molecule having quantitative and/or qualitative biological activity in common with the wild-type molecule from which the fragment or variant was derived. For example, a functional fragment or a functional variant of an antibody is one which retains essentially the same ability to bind to the same epitope as the antibody from which the functional fragment or functional variant was derived. For instance, an antibody capable of binding to an epitope of a cell surface receptor may be truncated at the N-terminus and/or C-terminus, and the retention of its epitope binding activity assessed using assays known to those of skill in the art. In some embodiments, the antigen-binding moiety includes one or more antigen-binding determinants of an antibody or a functional antigen-binding fragment thereof. In some embodiments, the antigen-binding moiety is selected from the group consisting of an antibody, a nanobody, a diabody, a triabody, or a minibody, an F(ab')2 fragment, an F(ab) fragment, a single chain variable fragment (scFv), and a single domain antibody (sdAb), or a functional fragment thereof. In some embodiments, the antigen-binding moiety includes an scFv.

The antigen-binding moiety can include naturally-occurring amino acid sequences or can be engineered, designed, or modified so as to provide desired and/or improved properties, such as, e.g., binding affinity. Generally, the binding affinity of an antigen-binding moiety, e.g., an antibody, for a target antigen (e.g., CD19 antigen) can be calculated by the Scatchard method described by Frankel et al., *Mol. Immunol*, 16:101-06, 1979. In some embodiments, binding affinity is measured by an antigen/antibody dissociation rate. In some embodiments, binding affinity is measured by a competition radioimmunoassay. In some embodiments, binding affinity is measured by ELISA. In some embodiments, antibody affinity is measured by flow cytometry. An antibody that "selectively binds" an antigen (such as CD19) is an antigen-binding moiety that does not significantly bind other antigens but binds the antigen with high affinity, e.g., with an equilibrium constant (KD) of 100 nM or less, such as 60 nM or less, for example, 30 nM or less, such as, 15 nM or less, or 10 nM or less, or 5 nM or less, or 1 nM or less, or 500 pM or less, or 400 pM or less, or 300 pM or less, or 200 pM or less, or 100 pM or less.

A skilled artisan can select an ECD based on the desired localization or function of a cell that is genetically modified to express a chimeric polypeptide or miniNotch receptor of the present disclosure. For example, a chimeric polypeptide or miniNotch receptor with an ECD comprising an antibody specific for a HER2 antigen can target the genetically modified cells to HER2-expressing breast cancer cells. In some embodiments, the ECD of the chimeric polypeptide miniNotch receptors is capable of binding a tumor-associated antigen (TAA) or a tumor-specific antigen (TSA). TAAs include a molecule, such as e.g., protein, present on tumor cells and on normal cells, or on many normal cells, but at much lower concentration than on tumor cells. In contrast, TSAs generally include a molecule, such as e.g., protein which is present on tumor cells but absent from normal cells.

In some cases, the antigen-binding moiety is specific for an epitope present in an antigen that is expressed by a tumor cell, i.e., a tumor-associated antigen. The tumor-associated antigen can be an antigen associated with, e.g., a breast cancer cell, a B cell lymphoma, a pancreatic cancer, a Hodgkin lymphoma cell, an ovarian cancer cell, a prostate cancer cell, a mesothelioma, a lung cancer cell, a non-Hodgkin B-cell lymphoma (B-NHL) cell, an ovarian cancer cell, a prostate cancer cell, a mesothelioma cell, a melanoma cell, a chronic lymphocytic leukemia cell, an acute lymphocytic leukemia cell, a neuroblastoma cell, a glioma, a glioblastoma, a colorectal cancer cell, etc. It will also be understood that a tumor-associated antigen may also be expressed by a non-cancerous cell. In some embodiments, the antigen-binding domain is specific for an epitope present in a tissue-specific antigen. In some embodiments, the antigen-binding domain is specific for an epitope present in a disease-associated antigen. In some embodiments, the antigen-binding domain is specific for an epitope present in an antigen that is both tissue-specific and disease-specific.

Non-limiting examples of suitable target antigens include CD19, B7H3 (CD276), BCMA (CD269), alkaline phosphatase, placental-like 2 (ALPPL2), green fluorescent protein (GFP), enhanced green fluorescent protein (eGFP), and signal regulatory protein α (SIRPα), CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Rα, KIT (CD117), MUC1, NCAM, PAP, PDGFR-β, PRSS21, PSCA, PSMA, ROR1, SSEA-4, TAG72, TEM1/CD248, TEM7R, TSHR, VEGFR2, ALPI, citrullinated vimentin, cMet, and Axl.

In some embodiments, the target antigen is selected from CD19, B7H3 (CD276), BCMA (CD269), CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Rα, KIT (CD117), MUC1, NCAM, PAP, PDGFR-β, PRSS21, PSCA, PSMA, ROR1, SSEA-4, TAG72, TEM1/CD248, TEM7R, TSHR, VEGFR2, ALPI, citrullinated vimentin, cMet, Axl, GPC2, human epidermal growth factor receptor 2 (Her2/neu), CD276 (B7-H3), IL-13Rα1, IL-13Rα2, α-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, AOC3 (VAP-1), CAM-3001, CCL11 (eotaxin-1), CD125, CD147 (basigin), CD154 (CD40L), CD2, CD20, CD23 (IgE receptor), CD25 (a subunit of the heterodimeric IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNF-α, VEGF-A, pyruvate kinase isoenzyme type M2 (tumor M2-PK), CD20, CD5, CD7, CD3, TRBC1, TRBC2, BCMA, CD38, CD123, CD93, CD34, CD1a, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin.

Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin β3 (CD61), galactin, K-Ras (V-Ki-ras2 Kirsten rat sarcoma viral oncogene), Ral-B, GPC2, CD276 (B7H3), or IL-13Rα. In some embodiments, the antigen includes Her2. In some embodiments, the antigen includes ALPPL2. In some embodiments, the antigen includes BCMA. In some embodiments, the antigen-binding moiety of the ECD is specific for a reporter protein, such as GFP and eGFP. Non-limiting examples of such antigen binding moiety include a LaG17 anti-GFP nanobody. In some embodiments, the antigen-binding moiety of the ECD includes an anti-BCMA fully-humanized VH domain (FHVH). In some embodiments, the antigen includes signal regulatory protein α (SIRPα).

Additional antigens suitable for targeting by the chimeric polypeptide receptors disclosed herein include, but are not limited to, GPC2, human epidermal growth factor receptor 2 (Her2/neu), CD276 (B7H3), IL-13Rα1, IL-13Rα2, α-fetoprotein (AFP), carcinoembryonic antigen (CEA), cancer antigen-125 (CA-125), CA19-9, calretinin, MUC-1, epithelial membrane protein (EMA), epithelial tumor antigen (ETA). Other suitable target antigens include, but are not limited to, tyrosinase, melanoma-associated antigen (MAGE), CD34, CD45, CD123, CD93, CD99, CD117, chromogranin, cytokeratin, desmin, glial fibrillary acidic protein (GFAP), gross cystic disease fluid protein (GCDFP-15), ALK, DLK1, FAP, NY-ESO, WT1, HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1.

Additional antigens suitable for targeting by the chimeric receptors disclosed herein include, but are not limited to, those associated with an inflammatory disease such as, AOC3 (VAP-1), CAM-3001, CCL11 (eotaxin-1), CD125, CD147 (basigin), CD154 (CD40L), CD2, CD20, CD23 (IgE receptor), CD25 (a subunit of the heterodimeric IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11α), myostatin, OX-40, scleroscin, SOST, TGFβ1, TNFα, and VEGF-A.

Further antigens suitable for targeting by the chimeric polypeptides and miniNotch receptors disclosed herein include, but are not limited to the pyruvate kinase isoenzyme type M2 (tumor M2-PK), CD20, CD5, CD7, CD3, TRBC1, TRBC2, BCMA, CD38, CD123, CD93, CD34, CD1a, SLAMF7/CS1, FLT3, CD33, CD123, TALLA-1, CSPG4, DLL3, Kappa light chain, Lamba light chain, CD16/FcγRIII, CD64, FITC, CD22, CD27, CD30, CD70, GD2 (ganglioside G2), GD3, EGFRvIII (epidermal growth factor variant III), EGFR and isovariants thereof, TEM-8, sperm protein 17 (Sp17), mesothelin. Further non-limiting examples of suitable antigens include PAP (prostatic acid phosphatase), prostate stem cell antigen (PSCA), prostein, NKG2D, TARP (T cell receptor gamma alternate reading frame protein), Trp-p8, STEAP1 (six-transmembrane epithelial antigen of the prostate 1), an abnormal ras protein, an abnormal p53 protein, integrin β3 (CD61), galactin, K-Ras (V-Ki-ras2 Kirsten rat sarcoma viral oncogene), and Ral-B. In some embodiments, the antigen is GPC2, CD19, Her2/neu, CD276 (B7H3), IL13-Rα1, or IL-13Rα2. In some embodiments, the antigen is ALPPL2. In some embodiments, the antigen is BCMA. In some embodiments, the antigen-binding moiety of the ECD is specific for a reporter protein, such as GFP and eGFP. Non-limiting examples of such antigen binding moiety include a LaG17 anti-GFP nanobody. In some embodiments, the antigen-binding moiety of the ECD includes an anti-BCMA fully-humanized VH domain (FHVH).

In some embodiments, antigens suitable for targeting by the chimeric polypeptides and miniNotch receptors disclosed herein include ligands derived from a pathogen. For example, the antigen can be HER2 produced by HER2-positive breast cancer cells. In some embodiments, the antigen can be CD19 that is expressed on B-cell leukemia.

In some embodiments, the antigen can be EGFR that is expressed on glioblastoma multiform (GBM) but much less expressed so on healthy CNS tissue. In some embodiments, the antigen can be CEA that is associated with cancer in adults, for example colon cancer.

In some embodiments, the antigen-binding moiety of the extracellular domain is specific for a cell surface target, where non-limiting examples of cell surface targets include CD19, CD30, Her2, ALPPL2, BCMA, CD22, ENPP3, EGFR, CD20, CD52, CD11α, and α-integrin. In some embodiments, the chimeric polypeptides and miniNotch receptors disclosed herein include an extracellular domain having an antigen-binding moiety that binds CD19, CEA, HER2, MUC1, CD20, BCMA, ALPPL2, or EGFR. In some embodiments, the chimeric polypeptides and miniNotch receptors disclosed herein include an extracellular domain including an antigen-binding moiety that binds CD19, BCMA, Her2, or ALPPL2.

In some embodiments, the antigen-binding moiety includes an amino acid sequence having at least 70%, at least 75%, at least 80%, at least 85%, at least 90%, at least 95%, at least 96%, at least 97%, at least 98%, at least 99% sequence identity to one or more of SEQ ID NOS: 10-18 in the Sequence Listing. In some embodiments, the antigen-binding moiety includes an amino acid sequence having at least 90% sequence identity to a sequence selected from the group consisting of SEQ ID NOS: 10-18. In some embodiments, the antigen-binding moiety includes an amino acid sequence having at least 95% sequence identity to a sequence selected from the group consisting of SEQ ID NOS: 10-18. In some embodiments, the antigen-binding moiety includes an amino acid sequence having 100% sequence identity to one or more of SEQ ID NOS: 10-18. In some embodiments, the antigen-binding moiety includes an amino acid sequence having a sequence selected from the group consisting of SEQ ID NOS: 10-18, wherein one, two, three, four, or five of the amino acid residues in any one of the SEQ ID NOS: 10-18 is/are substituted by a different amino acid residue.

Linking Polypeptide and JMD

As described above, the chimeric polypeptides and receptors of the disclosure include a linking sequence disposed between the extracellular binding domain (ECD) and the transmembrane domain (TMD). Existing "SynNotch" receptors comprise a heterologous extracellular ligand binding domain, a linking polypeptide having substantial sequence identity with a Notch receptor JMD including the NRR, a TMD, and an ICD. In contrast, the chimeric polypeptides and miniNotch receptors of the disclosure comprise a heterologous extracellular ligand-binding domain, a linking polypeptide having substantial sequence identity with a Notch receptor JMD but lacking the NRR (the LIN-12-Notch repeat (LNR) modules, and the heterodimerization domain), a TMD, and an ICD. Stated differently, in miniNotch receptors, the linking polypeptide replaces the negative regulatory region (NRR) and heterodimerization (HD) domain of the native Notch. Three to 50 amino acid residues (e.g., 3, 4, 5, 6, 7, 8, 9, 10, 11, 12, 13, 14, 15, 16, 17, 18, 19, 20, etc. amino acid residues) can be used as a polypeptide linker. In some embodiments, the length and amino acid composition of the linker polypeptide sequence can be optimized to vary the orientation and/or proximity of the ECD and the TMD relative to one another to achieve a desired activity of the chimeric polypeptide of the disclosure. In some embodiments, the linker polypeptide sequence includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 19-27 in the Sequence Listing. In some embodiments, the linker polypeptide sequence includes an amino acid sequence having at least 90% sequence identity to a sequence selected from the group consisting of SEQ ID NOS: 19-27. In some embodiments, the linker polypeptide sequence includes an amino acid sequence having at least 95% sequence identity to a sequence selected from the group consisting of SEQ ID NOS: 19-27. In some embodiments, the linker polypeptide sequence includes an amino acid sequence having about 100% sequence identity to a sequence selected from the group consisting of SEQ ID NOS: 19-27. In some embodiments, the linker polypeptide sequence includes an amino acid sequence having a sequence selected from the group consisting of SEQ ID NOS: 19-27, wherein one, two, three, four, or five of the amino acid residues in any one of the SEQ ID NOS: 19-27 is/are substituted by a different amino acid residue.

Transmembrane Domains

As described above, the chimeric polypeptides of the disclosure include a transmembrane domain comprising one or more ligand-inducible proteolytic cleavage sites.

Examples of proteolytic cleavage sites in a Notch receptor (e.g., S2 or S3) are as described above. Additional proteolytic cleavage sites suitable for the compositions and methods disclosed herein include, but are not limited to, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue such as Leu, Ile, Val, Phe, Trp, Tyr, Val, Met, and Pro) (SEQ ID NO: 58), e.g., Pro-X-X-Hy-(Ser/Thr) (SEQ ID NO: 59), e.g., Pro-Leu/Gln-Gly-Met-Thr-Ser (SEQ ID NO: 60) or Pro-Leu/Gln-Gly-Met-Thr (SEQ ID NO: 61). Another example of a suitable protease cleavage site is a plasminogen activator cleavage site, e.g., a urokinase plasminogen activator (uPA) or a tissue plasminogen activator (tPA) cleavage site. Another example of a suitable protease cleavage site is a prolactin cleavage site. Specific examples of cleavage sequences of uPA and tPA include sequences comprising Val-Gly-Arg (SEQ ID NO: 62. Another exemplary protease cleavage site that can be included in a proteolytically cleavable linker is a tobacco etch virus (TEV) protease cleavage site, e.g., Glu-Asn-Leu-Tyr-Thr-Gln-Ser (SEQ ID NO: 63), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 64), where cleavage occurs after the lysine residue. Another example of a protease cleavage site that can be included in a proteolytically cleavable linker is a thrombin cleavage site, e.g., Leu-Val-Pro-Arg (SEQ ID NO: 65). Additional suitable linkers comprising protease cleavage sites include sequences cleavable by the following proteases: a PreScission™ protease (a fusion protein comprising human rhinovirus 3C protease and glutathione-S-transferase), a thrombin, cathepsin B, Epstein-Barr virus protease, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator, membrane type 1 matrixmetalloproteinase (MT- MMP), stromelysin 3 (or MMP-11), thermolysin, fibroblast collagenase and stromelysin-1, matrix metalloproteinase 13 (collagenase-3), urokinase plasminogen activator (uPA), tissue-type plasminogen activator (tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the MiniNotch is not possible until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

Generally, the transmembrane domain (TMD) suitable for the chimeric polypeptides and miniNotch receptors disclosed herein can be any transmembrane domain of a Type 1 transmembrane receptor including at least one γ-secretase cleavage site. Detailed description of the structure and function of the γ-secretase complex as well as its substrate proteins, including amyloid precursor protein (APP) and Notch, can, for example, be found in a recent review by Zhang et al., *Frontiers Cell Neurosci* (2014). Non-limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one γ-secretase cleavage site. Additional TMDs suitable for the compositions and methods described herein include, but are not limited to, transmembrane domains from Type 1 transmembrane receptors IL1R1, IL1R2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the disclosure is a TMD derived from the TMD of a member of the calsyntenin family, such as, alcadein alpha and alcadein gamma. In some embodiments, the TMD of the chimeric polypeptides or Notch receptors of the disclosure is a TMD known for Notch receptors. In some embodiments, the TMD of the chimeric polypeptides or Notch receptors of the disclosure is a TMD derived from a different Notch receptor. For example, in a miniNotch based on human Notch1, the Notch1 TMD can be substituted with a human Notch2 TMD, human Notch3 TMD, human Notch4 TMD, or a Notch TMD from a non-human animal such as *Danio rerio*, *Drosophila melanogaster*, *Xenopus laevis*, or *Gallus gallus*.

In some embodiments, the transmembrane domain includes an amino acid sequence exhibiting at least 70%, at least 75%, at least 80%, at least 85%, at least 90%, at least 95%, at least 96%, at least 97%, at least 98%, at least 99% sequence identity to one or more of SEQ ID NOS: 28-36 in the Sequence Listing. In some embodiments, the transmembrane domain includes an amino acid sequence having at least 90% sequence identity to a sequence selected from the group consisting of SEQ ID NOS: 28-36. In some embodiments, the transmembrane domain includes an amino acid sequence having at least 95% sequence identity to a sequence selected from the group consisting of SEQ ID NOS: 28-36. In some embodiments, the transmembrane domain includes an amino acid sequence having 100% sequence identity to one or more of SEQ ID NOS: 28-36. In some embodiments, the transmembrane domain includes an amino acid sequence having a sequence selected from the group consisting of SEQ ID NOS: 28-36, wherein one, two, three, four, or five of the amino acid residues in any one of the SEQ ID NOS: 28-36 is/are substituted by a different amino acid residue.

In some embodiments, the amino acid substitution(s) within the TMD includes one or more substitutions within a "GV" motif of the TMD. In some embodiments, at least one of such substitutions is a substitution to alanine. For example, one, two, three, four, five, or more of the amino acid residues of the sequence FMYVAAAAFVLL-FFVGCGVLLS (SEQ ID NO: 28) may be substituted by a different amino acid residue. In some embodiments, the amino acid residue at position 18 and/or 19 of the "GV" motif within SEQ ID NO: 28 is substituted by a different amino acid residue. In some embodiments, the glycine residue at position 18 of SEQ ID NO: 28 is substituted by a different amino acid residue. In some embodiments, the valine residue at position 19 of SEQ ID NO: 28 is substituted by a different amino acid residue. In some embodiments, the transmembrane domain comprises an amino acid sequence having a sequence corresponding to SEQ ID NO: 28 with a mutation at the position corresponding to position 18 of SEQ ID NO: 28, such as G18A mutations. In some embodiments, the transmembrane domain comprises an amino acid sequence having a sequence corresponding to SEQ ID NO: 28 with a mutation at the position corresponding to position 19 of SEQ ID NO: 28, such as V19A mutations.

Stop-Transfer-Sequences

In some embodiments, the chimeric polypeptides and miniNotch receptors of the disclosure include a stop-transfer-sequence (STS) which constitutes a highly-charged domain located between the TMD and the ICD. Without being bound to any particular theory, such a highly-charged domain disposed between the TMD and the ICD prevents the ICD from entering the membrane. The STS is linked to the TMD and the ICD in the following order, from N-terminus to C-terminus, TMD-STS-ICD. In principle, there are no particular limitations to the length and/or amino acid composition of the STS. In some embodiments, any arbitrary single-chain peptide comprising about 4 to about 40 amino acid residues (e.g., 4, 5, 6, 7, 8, 9, 10, 11, 12, 13, 14, 15, 16, 17, 18, 19, or 20, etc. amino acid residues) can be used as a STS. In some embodiments, the STS includes about 4 to 15, about 6 to 20, about 8 to 25, about 10 to 30, about 12 to 35, about 14 to 40, about 5 to 40, about 10 to 35, about 15 to 30, about 20 to 25, about 20 to 40, about 10 to 30, about 4 to 20, or about 5 to 25 amino acid residues. In some embodiments, the STS includes about 4 to 10, about 5 to 12, about 6 to 14, about 7 to 18, about 8 to 20, about 9 to 22, about 10 to 24, or about 11 to 26 amino acid residues. In some embodiments, the STS includes about 4 to 10 residues, such as, 4, 5, 6, 7, 8, 9, or 10 amino acid residues.

In some embodiments, the STS comprises a sequence having at least 70% sequence identity, such as, at least 70%, at least 75%, at least 80%, at least 85%, at least 90%, at least 95%, at least 96%, at least 97%, at least 98%, or 99% sequence identity to a STS sequence from CLSTN1, CLSTN2, Notch1, Notch2, Notch3, Notch4, CSF1R, CXCL16, DAG1, GHR, PTPRF, AGER, KL, NRG1, LRP1B, Jag2, EPCAM, KCNE3, CDH2, NRG2, PTPRK, BTC, EPHA3, IL1R2, or PTPRM. In some embodiments, the STS comprises a sequence comprising only Lys (K) or Arg (R) in the first 4 residues. In some embodiments, the STS comprises one, two, three, four, five, or more basic residues. In some embodiments, the STS comprises five, four, three, two, one, or zero aromatic residues or residues with hydrophobic and/or bulky side chains.

In some embodiments, the STS includes a sequence having at least 80% sequence identity, such as, at least 80%, at least 85%, at least 90%, at least 95%, at least 96%, at least 97%, at least 98%, or 99% sequence identity to a sequence selected from the group consisting of SEQ ID NOS: 37-45 in the Sequence Listing. In some embodiments, the STS includes an amino acid sequence having at least 90% sequence identity to a sequence selected from the group consisting of SEQ ID NOS: 37-45. In some embodiments, the STS includes an amino acid sequence having at least 95% sequence identity to a sequence selected from the group consisting of SEQ ID NOS: 37-45. In some embodiments, the STS includes an amino acid sequence having about 100% sequence identity to a sequence selected from the group consisting of SEQ ID NOS: 37-45. In some embodiments, the STS includes an amino acid sequence having a sequence selected from the group consisting of SEQ ID NOS: 37-45, wherein one, two, three, four, or five of the amino acid residues in any one of the SEQ ID NOS: 37-45 is/are substituted by a different amino acid residue.

Intracellular Domain

The chimeric polypeptides and miniNotch receptors of the disclosure include a transcriptional regulator. The transcriptional regulator of the disclosure is a polypeptide element that acts to activate or inhibit the transcription of a promoter-driven DNA sequence. Transcriptional regulators suitable for the compositions and methods of the disclosure can be naturally-occurring transcriptional regulators or can be engineered, designed, or modified so as to provide desired and/or improved properties, e.g., modulating transcription. As discussed above, the engineered receptors of the present disclosure are advantageous in that they can provide the ability to trigger a custom transcriptional program in engineered cells. In some embodiments, transcriptional regulator of the disclosure is a custom transcriptional regulator that drives transcription off a specific sequence that only appears once in the engineered cell.

In some embodiments, the transcriptional regulator directly regulates differentiation of the cell. In some embodiments, the transcriptional regulator indirectly modulates differentiation of the cell by modulating the expression of a second transcription factor. It will be understood by one having ordinary skill in the art that a transcriptional regulator can be a transcriptional activator or a transcriptional repressor. In some embodiments, the transcriptional regulator is a transcriptional repressor. In some embodiments, the transcriptional regulator is a transcriptional activator. In some embodiments, the transcriptional regulator can further include a nuclear localization signal. In some embodiments, the transcriptional regulator is selected from Gal4-VP16, Gal4-VP64, tetR-VP64, ZFHD1-VP64, Gal4-KRAB, and HAP1-VP16. In some embodiments, the transcriptional regulator is Gal4-VP64.

Chimeric polypeptides and miniNotch receptors of the present disclosure can be chimeric polypeptides of any length, including chimeric polypeptides that are generally between about 100 amino acids (aa) to about 1000 aa, e.g., from about 100 aa to about 200 aa, from about 150 aa to about 250 aa, from about 200 aa to about 300 aa, from about 250 aa to about 350 aa, from about 300 aa to about 400 aa, from about 350 aa to about 450 aa, from about 400 aa to about 500 aa in length. In some embodiments, the disclosed chimeric polypeptides are generally between about 400 aa to about 450 aa, from about 450 aa to about 500 aa, from about 500 aa to about 550 aa, from about 550 aa to about 600 aa, from about 600 aa to about 650 aa, from about 650 aa to about 700 aa, from about 700 aa to about 750 aa, from about 750 aa to about 800 aa, from about 800 aa to about 850 aa, from about 850 aa to about 900 aa, from about 900 aa to about 950 aa, or from about 950 aa to about 1000 aa in length. In some cases, the chimeric polypeptides of the present disclosure has a length of from about 300 aa to about 400 aa. In some cases, the chimeric polypeptides of the present disclosure has a length of from 300 aa to 350 aa. In some cases, the chimeric polypeptides of the present disclosure has a length of from 300 aa to 325 aa. In some cases, the chimeric polypeptides of the present disclosure has a length of from 350 aa to 400 aa. In some cases, the chimeric polypeptides of the present disclosure has a length of from 750 aa to 850 aa. In some embodiments, the chimeric polypeptides of the present disclosure have a length of about 538 aa, about 543 aa, about 544 aa, or about 598 aa.

Additional Domains

In some embodiments, the Notch extracellular domains located N-terminally to the TMD can further include an additional domain, for example a membrane localization signal such as a CD8A signal, a detectable marker such as a myc tag or his tag, and the like. It is also contemplated that the chimeric polypeptides and miniNotch receptors as described herein can be further engineered to include one or more additional features such as, a signal sequence, a detectable label, a tumor-specific cleavage site, a disease-specific cleavage site, or combinations thereof. For example, several proteases (such as matrix metalloproteases) are upregulated in cancers, allowing tumor-specific cleavage specificity not via a specific cleavage site but via higher levels of specific proteases. Additional information in this regard can be found in, for example, J. S. Dudani et al., Annu. Rev. Cancer Biol. (2018), 2:353-76, which is herein incorporated by reference.

In some embodiments, the chimeric polypeptide or miniNotch receptor of the disclosure comprises: (a) a linking polypeptide comprising an amino acid sequence having at least 80% sequence identity to any one of SEQ ID NO: 19-27; (b) a transmembrane domain comprising an amino acid sequence having at least 80% sequence identity to any one of SEQ ID NOS: 28-36; and (c) a stop-transfer-sequence comprising an amino acid sequence having at least 80% sequence identity to any one of SEQ ID NOS: 37-45. In some embodiments, the chimeric polypeptide or miniNotch receptor of the disclosure comprises: (a) a linking polypeptide comprising an amino acid sequence having at least 90% sequence identity to any one of SEQ ID NO: 19-27; (b) a transmembrane domain comprising an amino acid sequence having at least 90% sequence identity to any one of SEQ ID NOS: 28-36; and (c) a stop-transfer-sequence comprising an amino acid sequence having at least 90% sequence identity to any one of SEQ ID NOS: 37-45. In some embodiments, the chimeric polypeptide of the disclosure comprises: (a) a linking polypeptide comprising an amino acid sequence having at least 95% sequence identity to any one of SEQ ID NO: 19-27; (b) a transmembrane domain comprising an amino acid sequence having at least 95% sequence identity to any one of SEQ ID NOS: 28-36; and (c) a stop-transfer-sequence comprising an amino acid sequence having at least 95% sequence identity to any one of SEQ ID NOS: 37-45.

In some embodiments, the chimeric polypeptide of the disclosure comprises: (a) a linking polypeptide comprising an amino acid sequence selected from the group consisting of SEQ ID NO: 19-27; (b) a transmembrane domain comprising an amino acid sequence selected from the group consisting of SEQ ID NOS: 28-36; and (c) a stop transfer sequence domain comprising an amino acid sequence selected from the group consisting of SEQ ID NOS: 37-45.

In some embodiments, the chimeric polypeptide of the disclosure comprises: (a) a linking polypeptide comprising an amino acid sequence selected from the group consisting of SEQ ID NO: 19-27, wherein one, two, three, four, or five of the amino acid residues in any one of the SEQ ID NOS: 19-27 is/are substituted by a different amino acid residue; (b) a transmembrane domain comprising an amino acid sequence selected from the group consisting of SEQ ID NOS: 28-36, wherein one, two, three, four, or five of the amino acid residues in any one of the SEQ ID NOS: 28-36 is/are substituted by a different amino acid residue; and (c) a stop transfer sequence domain comprising an amino acid sequence selected from the group consisting of SEQ ID NOS: 37-45, wherein one, two, three, four, or five of the amino acid residues in any one of the SEQ ID NOS: 37-45 is/are substituted by a different amino acid residue.

In some embodiments, the chimeric receptor of the disclosure includes an amino acid sequence having at least about 80%, 90%, 95%, 96%, 97, 98%, 99%, or 100% sequence identity to a chimeric receptor disclosed herein. In some embodiments, provided herein are chimeric receptors including an amino acid sequence having at least about 80%, 90%, 95%, 96%, 97, 98%, 99%, or 100% sequence identity to any one of SEQ ID NOs: 1-9 as identified in the Sequence Listing. In some embodiments, the chimeric receptors include an amino acid sequence having at least about 80%, 90%, 95%, 96%, 97, 98%, 99%, or 100% sequence identity to SEQ ID NO: 1. In some embodiments, the chimeric receptors include an amino acid sequence having at least about 80%, 90%, 95%, 96%, 97, 98%, 99%, or 100% sequence identity to SEQ ID NO: 2. In some embodiments, the chimeric receptors include an amino acid sequence having at least about 80%, 90%, 95%, 96%, 97, 98%, 99%, or 100% sequence identity to SEQ ID NO: 3. In some embodiments, the chimeric receptors include an amino acid sequence having at least about 80%, 90%, 95%, 96%, 97, 98%, 99%, or 100% sequence identity to SEQ ID NO: 4.

In some embodiments, the chimeric receptors include an amino acid sequence having at least about 80%, 90%, 95%, 96%, 97, 98%, 99%, or 100% sequence identity to SEQ ID NO: 5. In some embodiments, the chimeric receptors include an amino acid sequence having at least about 80%, 90%, 95%, 96%, 97, 98%, 99%, or 100% sequence identity to SEQ ID NO: 6. In some embodiments, the chimeric receptors include an amino acid sequence having at least about 80%, 90%, 95%, 96%, 97, 98%, 99%, or 100% sequence identity to SEQ ID NO: 7. In some embodiments, the chimeric receptors include an amino acid sequence having at least about 80%, 90%, 95%, 96%, 97, 98%, 99%, or 100% sequence identity to SEQ ID NO: 8. In some embodiments, the chimeric receptors include an amino acid sequence having at least about 80%, 90%, 95%, 96%, 97, 98%, 99%, or 100% sequence identity to SEQ ID NO: 9.

Nucleic Acid Molecules

In another aspect, provided herein are various nucleic acid molecules comprising nucleotide sequences encoding the chimeric polypeptides and miniNotch receptors of the disclosure, including expression cassettes, and expression vectors containing these nucleic acid molecules operably linked to heterologous nucleic acid sequences such as, for example, regulatory sequences which facilitate in vivo expression of the receptor in a host cell.

Nucleic acid molecules of the present disclosure can be of any length, including, for example, between about 1.5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or between about 30 Kb and about 50 Kb.

In some embodiments, provided herein is a nucleic acid molecule comprising a nucleotide sequence encoding a chimeric polypeptide or miniNotch receptor including, from N-terminus to C-terminus: (a) an ECD comprising a binding moiety having a binding affinity for a selected ligand; (b) a linking polypeptide; (c) a TMD including one or more ligand-inducible proteolytic cleavage sites; and (d) an ICD including a transcriptional regulator, wherein binding of the selected ligand to the ECD induces cleavage at the ligand-inducible proteolytic cleavage site between the transcriptional regulator and the linking polypeptide, and wherein the chimeric polypeptide does not include a LIN-12-Notch repeat (LNR) and/or a heterodimerization domain (HD) of a Notch receptor.

In some embodiments, the nucleotide sequence is incorporated into an expression cassette or an expression vector. It will be understood that an expression cassette generally includes a construct of genetic material that contains coding sequences and enough regulatory information to direct proper transcription and/or translation of the coding sequences in a recipient cell, in vivo and/or ex vivo. Generally, the expression cassette may be inserted into a vector for targeting to a desired host cell and/or into an individual. As such, in some embodiments, an expression cassette of the disclosure include a coding sequence for the chimeric polypeptide as disclosed herein, which is operably linked to expression control elements, such as a promoter, and optionally, any or a combination of other nucleic acid sequences that affect the transcription or translation of the coding sequence.

In some embodiments, the nucleotide sequence is incorporated into an expression vector. It will be understood by one skilled in the art that the term "vector" generally refers to a recombinant polynucleotide construct designed for transfer between host cells, and that may be used for the purpose of transformation, e.g., the introduction of heterologous DNA into a host cell. As such, in some embodiments, the vector can be a replicon, such as a plasmid, phage, or cosmid, into which another DNA segment may be inserted so as to bring about the replication of the inserted segment. In some embodiments, the expression vector can be an integrating vector.

In some embodiments, the expression vector can be a viral vector. As will be appreciated by one of skill in the art, the term "viral vector" is widely used to refer either to a nucleic acid molecule (e.g., a transfer plasmid) that includes virus-derived nucleic acid elements that generally facilitate transfer of the nucleic acid molecule or integration into the genome of a cell or to a viral particle that mediates nucleic acid transfer. Viral particles generally include various viral components and sometimes also host cell components in addition to nucleic acid(s). The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

In some embodiments, provided herein are nucleic acid molecules encoding a polypeptide with an amino acid sequence having at least about 80%, 90%, 95%, 96%, 97, 98%, 99%, or 100% sequence identity to a chimeric receptor disclosed herein. In some embodiments, provided herein are nucleic acid molecules encoding a polypeptide with an amino acid sequence having at least about 80%, 90%, 95%, 96%, 97, 98%, 99%, or 100% sequence identity to any one of SEQ ID NOS: 1-9 identified in the Sequence Listing. In some embodiments, the nucleic acid molecules encode a polypeptide with an amino acid sequence having at least about 80%, 90%, 95%, 96%, 97, 98%, 99%, or 100% sequence identity to SEQ ID NO: 1. In some embodiments, the nucleic acid molecules encode a polypeptide with an amino acid sequence having at least about 80%, 90%, 95%, 96%, 97, 98%, 99%, or 100% sequence identity to SEQ ID NO: 2. In some embodiments, the nucleic acid molecules encode a polypeptide with an amino acid sequence having at least about 80%, 90%, 95%, 96%, 97, 98%, 99%, or 100% sequence identity to SEQ ID NO: 3. In some embodiments, the nucleic acid molecules encode a polypeptide with an amino acid sequence having at least about 80%, 90%, 95%, 96%, 97, 98%, 99%, or 100% sequence identity to SEQ ID NO: 4. In some embodiments, the nucleic acid molecules encode a polypeptide with an amino acid sequence having at least about 80%, 90%, 95%, 96%, 97, 98%, 99%, or 100% sequence identity to SEQ ID NO: 5. In some embodiments, the nucleic acid molecules encode a polypeptide with an amino acid sequence having at least about 80%, 90%, 95%, 96%, 97, 98%, 99%, or 100% sequence identity to SEQ ID NO: 6. In some embodiments, the nucleic acid molecules encode a polypeptide with an amino acid sequence having at least about 80%, 90%, 95%, 96%, 97, 98%, 99%, or 100% sequence identity to SEQ ID NO: 7. In some embodiments, the nucleic acid molecules encode a polypeptide with an amino acid sequence having at least about 80%, 90%, 95%, 96%, 97, 98%, 99%, or 100% sequence identity to SEQ ID NO: 8. In some embodiments, the nucleic acid molecules encode a polypeptide with an amino acid sequence having at least about 80%, 90%, 95%, 96%, 97, 98%, 99%, or 100% sequence identity to SEQ ID NO: 9.

The nucleic acid sequences encoding the chimeric receptors can be optimized for expression in the host cell of interest. For example, the G-C content of the sequence can be adjusted to average levels for a given cellular host, as calculated by reference to known genes expressed in the host cell. Methods for codon optimization are known in the art. Codon usages within the coding sequence of the chimeric receptor disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Some embodiments disclosed herein relate to vectors or expression cassettes including a recombinant nucleic acid molecule encoding the chimeric receptors disclosed herein. The expression cassette generally contains coding sequences and sufficient regulatory information to direct proper transcription and/or translation of the coding sequences in a recipient cell, in vivo and/or ex vivo. The expression cassette may be inserted into a vector for targeting to a desired host cell and/or into an individual. An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, i.e., operably linked.

Also provided herein are vectors, plasmids, or viruses containing one or more of the nucleic acid molecules encoding any chimeric receptor or miniNotch receptor disclosed herein. The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). *Molecular Cloning: A Laboratory Manual* (4th ed.). Cold Spring Harbor, N.Y.: Cold Spring Harbor Laboratory and Sambrook, J., & Russel, D. W. (2001). *Molecular Cloning: A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual: The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferre, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference.

DNA vectors can be introduced into eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection. Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.). For example, a chimeric receptor as disclosed herein can be produced in a eukaryotic host, such as a mammalian cells (e.g., COS cells, NIH 3T3 cells, or HeLa cells). These cells are available from many sources, including the American Type Culture Collection (Manassas, Va.). In selecting an expression system, care should be taken to ensure that the components are compatible with one another. Artisans or ordinary skill are able to make such a determination. Furthermore, if guidance is required in selecting an expression system, skilled artisans may consult P. Jones, "Vectors: Cloning Applications", John Wiley and Sons, New York, N.Y., 2009).

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies); some or all of the non-coding sequences that lie upstream or downstream from a coding sequence (e.g., the coding sequence of a chimeric receptor) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Recombinant Cells and Cell Cultures

The nucleic acid of the present disclosure can be introduced into a host cell, such as a human T lymphocyte, to produce a recombinant cell containing the nucleic acid molecule. Accordingly, some embodiments of the disclosure relate to a methods for making a recombinant cell, including (a) providing a cell capable of protein expression and (b) contacting the provided cell with a recombinant nucleic acid of the disclosure.

Introduction of the nucleic acid molecules of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Accordingly, in some embodiments, the nucleic acid molecules can be delivered by viral or non-viral delivery means and methods known in the art. For example, the nucleic acid molecule can be stably integrated in the host genome, or can be episomally replicating, or present in the recombinant host cell as a mini-circle expression vector for a transient expression. Accordingly, in some embodiments, the nucleic acid molecule is maintained and replicated in the recombinant host cell as an episomal unit. In some embodiments, the nucleic acid molecule is stably integrated into the genome of the recombinant cell. Stable integration can be achieved using classical random genomic recombination techniques or with more precise genome editing techniques such as guide RNA-directed CRISPR/Cas9 genome editing, DNA-guided endonuclease genome editing with NgAgo (*Natronobacterium gregoryi* Argonaute), or TALENs genome editing (transcription activator-like effector nucleases). In some embodiments, the nucleic acid molecule is present in the recombinant host cell as a mini-circle expression vector for a transient expression.

The nucleic acid molecules can be encapsulated in a viral capsid or a lipid nanoparticle. Alternatively, endonuclease polypeptide(s) can be delivered by viral or non-viral delivery means and methods known in the art, such as electroporation or lipid nanoparticles. For example, introduction of nucleic acids into cells may be achieved using viral transduction methods. In a non-limiting example, adeno-associated virus (AAV) is a non-enveloped virus that can be engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral systems are also amenable to nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. Host cells can be either untransformed cells or cells that have already been transfected with at least one nucleic acid molecule.

In some embodiments, the recombinant cell is a prokaryotic cell or a eukaryotic cell. In some embodiments, the cell is in vivo. In some embodiments, the cell is ex vivo. In some embodiments, the cell is in vitro. In some embodiments, the recombinant cell is an animal cell. In some embodiments, the animal cell is a mammalian cell. In some embodiments, the animal cell is a human cell. In some embodiments, the cell is a non-human primate cell. In some embodiments, the mammalian cell is an immune cell, a neuron, an epithelial cell, and endothelial cell, or a stem cell. In some embodiments, the recombinant cell is an immune system cell, e.g., a lymphocyte (e.g., a T cell or NK cell), or a dendritic cell. In some embodiments, the immune cell is a B cell, a monocyte, a natural killer (NK) cell, a basophil, an eosinophil, a neutrophil, a dendritic cell, a macrophage, a regulatory T cell, a helper T cell ($T_H$), a cytotoxic T cell ($T_{CTL}$), or other T cell. In some embodiments, the immune system cell is a T lymphocyte.

In some embodiments, the cell is a stem cell. In some embodiments, the cell is a hematopoietic stem cell. In some embodiments of the cell, the cell is a lymphocyte. In some embodiments, the cell is a precursor T cell or a T regulatory (Treg) cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells.

In some embodiments of the cell, the cell is a CD4+ T helper lymphocyte cell selected from the group consisting of naïve CD4+ T cells, central memory CD4+ T cells, effector memory CD4+ T cells, and bulk CD4+ T cells. In some embodiments, the cell can be obtained by leukapheresis performed on a sample obtained from a subject. In some embodiments, the subject is a human patient.

In some embodiments, the recombinant cell further includes a second nucleic acid molecule as disclosed herein, wherein the first nucleic acid molecule and the second nucleic acid molecule do not have the same sequence. In some embodiments, the recombinant cell further includes a second chimeric polypeptide as disclosed herein, wherein the first chimeric polypeptide or miniNotch receptor and the second chimeric polypeptide or miniNotch receptor do not have the same sequence. In some embodiments, the first chimeric polypeptide modulates the expression and/or activity of the second chimeric polypeptide.

In some embodiments, the recombinant cell further includes an expression cassette encoding a protein of interest operably linked to a promoter, wherein expression of the protein of interest is modulated (e.g., inhibited, repressed, or induced) by the transcriptional regulator. In some embodiments, the protein of interest is heterologous to recombinant cell. In principle, there are no particular limitations with regard to suitable proteins whose expression can be modulated by the transcriptional regulator. Exemplary types of proteins whose expression can be modulated by the methods disclosed herein include cytokines, cytotoxins, chemokines, immunomodulators, pro-apoptotic factors, anti-apoptotic factors, hormones, differentiation factors, dedifferentiation factors, immune cell receptors or reporters. In some embodiments, the immune cell receptor comprises a T-cell receptor (TCR). In some embodiments, the immune cell receptor comprises a chimeric antigen receptor (CAR). In some embodiments, the expression cassette encoding the protein of interest is incorporated into the same nucleic acid molecule that encodes the chimeric receptor of the disclosure. In some embodiments, the expression cassette encoding the protein of interest is incorporated into a second expression vector that is separate from the nucleic acid molecule encoding the chimeric receptor of the disclosure.

In another aspect, provided herein are various cell cultures comprising at least one recombinant cell as disclosed herein, and a culture medium. Generally, the culture medium can be any suitable culture medium for the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Pharmaceutical Compositions

In some embodiments, the nucleic acids, and recombinant cells of the disclosure can be incorporated into compositions, including pharmaceutical compositions. Such compositions generally include the nucleic acids, and/or recombinant cells, and a pharmaceutically acceptable excipient, e.g., carrier.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.), or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

In some embodiments, the chimeric polypeptides and Notch receptors of the disclosure can also be administered by transfection or infection using methods known in the art, including but not limited to the methods described in McCaffrey et al. (*Nature* 418:6893, 2002), Xia et al. (*Nature Biotechnol.* 20:1006-10, 2002), or Putnam (*Am. J. Health Syst. Pharm.* 53:151-60, 1996, erratum at *Am. J. Health Syst. Pharm.* 53:325, 1996).

Methods of the Disclosure

Administration of any one of the therapeutic compositions described herein, e.g., nucleic acids, recombinant cells, and pharmaceutical compositions, can be used to treat patients for relevant health conditions or diseases, such as cancers and chronic infections. In some embodiments, the nucleic acids, recombinant cells, and pharmaceutical compositions described herein can be incorporated into therapeutic agents for use in methods of treating an individual who has, who is suspected of having, or who may be at high risk for developing one or more autoimmune disorders or diseases associated with checkpoint inhibition. Exemplary autoimmune disorders and diseases can include, without limitation, cancers and chronic infection.

Accordingly, in one aspect, some embodiments of the disclosure relate to methods for modulating (e.g., stimulating or inhibiting) an activity of a target cell in an individual, the methods include administering to the individual a first therapy including one or more of nucleic acids, recombinant cells, and pharmaceutical compositions as disclosed herein, wherein the first therapy modulates (e.g., inhibits or stimulates) an activity of the target cell. For example, an activity of the target cell may be inhibited if its proliferation is reduced, if its pathologic or pathogenic behavior is reduced, if it is destroyed or killed, etc. Inhibition includes a reduction of the measured pathologic or pathogenic behavior of at least about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the methods include administering to the individual an effective number of the recombinant cells as disclosed herein, wherein the recombinant cells modulate an activity of the target cells in the individual. Generally, the target cells of the disclosed methods can be any cell in the individual and can be, for example an acute myeloma leukemia cell, an anaplastic lymphoma cell, an astrocytoma cell, a B-cell cancer cell, a breast cancer cell, a colon cancer cell, an ependymoma cell, an esophageal cancer cell, a glioblastoma cell, a glioma cell, a leiomyosarcoma cell, a liposarcoma cell, a liver cancer cell, a lung cancer cell, a mantle cell lymphoma cell, a melanoma cell, a neuroblastoma cell, a non-small cell lung cancer cell, an oligodendroglioma cell, an ovarian cancer cell, a pancreatic cancer cell, a peripheral T-cell lymphoma cell, a renal cancer cell, a sarcoma cell, a stomach cancer cell, a carcinoma cell, a mesothelioma cell, or a sarcoma cell. In some embodiments, the target cell is a pathogenic cell.

In another aspect, some embodiments of the disclosure relate to methods for the treatment of a health condition (e.g., disease) in an individual in need thereof, the methods include administering to the individual a first therapy including one or more of the recombinant cells comprising a chimeric polypeptide or miniNotch receptor as disclosed herein, and/or pharmaceutical compositions as disclosed herein, wherein the first therapy treats the health condition in the individual. In some embodiments, the methods include administering to the individual a first therapy including an effective number of the recombinant cells as disclosed herein, wherein the recombinant cells treat the health condition.

In another aspect, some embodiments of the disclosure relate to methods for assisting in the treatment of a health condition (e.g., disease) in an individual in need thereof, the methods including administering to the individual a first therapy including one or more of chimeric polypeptides or miniNotch receptors, nucleic acids, recombinant cells, and pharmaceutical compositions as disclosed herein, and a second therapy, wherein the first and second therapies together treat the health condition in the individual. In some embodiments, the methods include administering to the individual a first therapy including an effective number of the recombinant cells as disclosed herein, wherein the recombinant cells treat the health condition.

Administration of Recombinant Cells to an Individual

In some embodiments, the methods of the disclosure involve administering an effective amount of the recombinants cells of the disclosure into an individual in need of such treatment. This administering step can be accomplished using any method of delivery known in the art. For example, the recombinant cells can be infused directly in the individual's bloodstream or otherwise administered to the individual.

In some embodiments, the methods disclosed herein include administering, which term is used interchangeably with "introducing," implanting," and "transplanting," recombinant cells into an individual, by a method or route that results in at least partial localization of the introduced cells at a desired site such that a desired effect(s) is(are) produced. The recombinant cells or their differentiated progeny can be administered by any appropriate route that results in delivery to a desired location in the individual where at least a portion of the administered cells or components of the cells remain viable. The period of viability of the cells after administration to an individual can be as short as a few hours, e.g., twenty-four hours, to a few days, to as long as several years, or even the life time of the individual, i.e., long-term engraftment.

When provided prophylactically, the recombinant cells described herein can be administered to an individual in advance of any symptom of a disease or condition to be treated. Accordingly, in some embodiments the prophylactic administration of a recombinant cell population prevents the occurrence of symptoms of the disease or condition.

When provided therapeutically in some embodiments, recombinant cells are provided at (or after) the onset of a symptom or indication of a disease or condition, e.g., upon the onset of disease or condition.

For use in the various embodiments described herein, an effective amount of recombinant cells as disclosed herein, can be at least $10^2$ cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The recombinant cells can be derived from one or more donors or can be obtained from an autologous source. In some embodiments, the recombinant cells are expanded in culture prior to administration to an individual in need thereof.

In some embodiments, the delivery of a recombinant cell composition (e.g., a composition comprising a plurality of recombinant cells according to any of the cells described herein) into an individual by a method or route results in at least partial localization of the cell composition at a desired site. A composition comprising recombinant cells can be administered by any appropriate route that results in effective treatment in the individual, e.g., administration results in delivery to a desired location in the individual where at least a portion of the composition delivered, e.g., at least $1\times10^4$ cells, is delivered to the desired site for a period of time. Modes of administration include injection, infusion, instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, delivery by injection or infusion is a preferred mode of administration.

In some embodiments, the recombinant cells are administered systemically, e.g., via infusion or injection. For example, a population of recombinant cells are administered other than directly into a target site, tissue, or organ, such that it enters, the individual's circulatory system and, thus is subject to metabolism and other similar biological processes.

The efficacy of a treatment comprising any of the compositions provided herein for the treatment of a disease or condition can be determined by a skilled clinician. However, one skilled in the art will appreciate that a treatment is considered effective if any one or all of the signs or symptoms or markers of disease are improved or ameliorated. Efficacy can also be measured by failure of an individual to worsen as assessed by decreased hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

As discussed above, a therapeutically effective amount includes an amount of a therapeutic composition that is sufficient to promote a particular beneficial effect when administered to an individual, such as one who has, is suspected of having, or is at risk for a disease. In some embodiments, an effective amount includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

In some embodiments of the disclosed methods, the individual is a mammal. In some embodiments, the mammal is a human. In some embodiments, the individual has or is suspected of having a disease associated with inhibition of cell signaling mediated by a cell surface ligand or antigen. The diseases suitable for being treated by the compositions and methods of the disclosure include, but are not limited to, cancers, autoimmune diseases, inflammatory diseases, and infectious diseases. In some embodiments, the disease is a cancer or a chronic infection.

Additional Therapies

As discussed above, the recombinant cells, and pharmaceutical compositions described herein can be administered in combination with one or more additional therapeutic agents such as, for example, chemotherapeutics or anti-cancer agents or anti-cancer therapies. Administration "in combination with" one or more additional therapeutic agents includes simultaneous (concurrent) and consecutive administration in any order. In some embodiments, the one or more additional therapeutic agents, chemotherapeutics, anti-cancer agents, or anti-cancer therapies is selected from the group consisting of chemotherapy, radiotherapy, immunotherapy, hormonal therapy, toxin therapy, and surgery. "Chemotherapy" and "anti-cancer agent" are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Methods for Modulating an Activity of a Cell

In another aspect, provided herein are various methods for modulating an activity of a cell. The methods comprise the steps of: (a) providing an effective number of any of the recombinant cells provided herein, and (b) contacting it with a selected ligand, wherein binding of the selected ligand to the extracellular ligand-binding domain induces cleavage of a ligand-inducible proteolytic cleavage site and releases the transcriptional regulator, wherein the released transcriptional regulator modulates (e.g., inhibits or stimulates) an activity of the recombinant cell. One skilled in the art upon reading the present disclosure will appreciate that the disclosed methods can be carried out in vivo, ex vivo, or in vitro.

Non-limiting exemplary cellular activities that can be modulated using the methods provided herein include, but are not limited to, gene expression, proliferation, apoptosis, non-apoptotic death, differentiation, dedifferentiation, migration, secretion of gene products, cellular adhesion, and cytolytic activity.

In some embodiments, the released transcriptional regulator modulates expression of a gene product of the cell. In some embodiments, the released transcriptional regulator modulates expression of a heterologous gene product in the cell. A heterologous gene product is one that is not normally found in the cell, e.g., not normally produced by the cell. For example, the cell can be genetically modified with a nucleic acid comprising a nucleotide sequence encoding the heterologous gene product.

In some embodiments, the heterologous gene product is a secreted gene product. In some embodiments, the heterologous gene product is a cell surface gene product. In some cases, the heterologous gene product is an intracellular gene product. In some embodiments, the released transcriptional regulator simultaneously modulates expression of two or more heterologous gene products in the cell.

In some embodiments, the heterologous gene product in the cell is selected from the group consisting of a chemokine, a chemokine receptor, a chimeric antigen receptor, a cytokine, a cytokine receptor, a differentiation factor, a growth factor, a growth factor receptor, a hormone, a metabolic enzyme, a pathogen derived protein, a proliferation inducer, a receptor, an RNA guided nuclease, a site-specific nuclease, a T-cell receptor (TCR), a chimeric antigen receptor (CAR), a toxin, a toxin-derived protein, a transcriptional regulator, a transcriptional activator, a transcriptional repressor, a translation regulator, a translational activator, a translational repressor, an activating immuno-receptor, an antibody, an apoptosis inhibitor, an apoptosis inducer, an engineered T-cell receptor, an immuno-activator, an immuno-inhibitor, and an inhibiting immuno-receptor.

In some embodiments, the released transcriptional regulator modulates differentiation of the cell, and wherein the cell is an immune cell, a stem cell, a progenitor cell, or a precursor cell.

The chimeric receptors of the disclosure provide a higher degree of expression than a standard SynNotch receptor, when using identical binding domains and ICDs. Depending on the ligand/binding domain pair and their affinity, the chimeric receptor or MiniNotch receptor can provide expression enhancement of about 10%, about 15%, about 20%, about 25%, about 30%, about 35%, about 40%, about 45%, or about 50% higher than a corresponding SynNotch receptor.

Additionally, the chimeric receptors of the disclosure can provide transcriptional regulation that responds to the degree of T cell activation, independent of ligand binding. For example, when expressed in a T-cell, some receptors of the disclosure provide a stronger ligand-induced signal when the T-cell is activated as compared to the ligand-induced signal produced when the T-cell is not activated. This permits additional flexibility in use, for example in cases where it is desired to enhance or suppress a T cell response when activated despite the absence of the chimeric receptor ligand.

Systems and Kits

Also provided herein are systems and kits including the chimeric polypeptides, miniNotch receptors, recombinant nucleic acids, recombinant cells, or pharmaceutical compositions provided and described herein as well as written instructions for making and using the same. For example, provided herein, in some embodiments, are systems and/or kits that include one or more of: an chimeric polypeptide as described herein, a miniNotch receptor as described herein, a recombinant nucleic acids as described herein, a recombinant cell as described herein, or a pharmaceutical composition as described herein. In some embodiments, the systems and/or kits of the disclosure further include one or more syringes (including pre-filled syringes) and/or catheters (including pre-filled syringes) used to administer one any of the provided chimeric polypeptides, miniNotch receptors, recombinant nucleic acids, recombinant cells, or pharmaceutical compositions to an individual. In some embodiments, a kit can have one or more additional therapeutic agents that can be administered simultaneously or sequentially with the other kit components for a desired purpose, e.g., for modulating an activity of a cell, inhibiting a target cancer cell, or treating a health condition (e.g., disease) in an individual in need thereof.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the chimeric receptor polypeptides.

In some embodiments, the components of a system or kit can be in separate containers. In some other embodiments, the components of a system or kit can be combined in a single container.

In some embodiments, a system or kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub-packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above.

Additional embodiments are disclosed in further detail in the following examples, which are provided by way of illustration and are not in any way intended to limit the scope of this disclosure or the claims.

Example 1

Design and Construction of Chimeric Receptor and Response Element Constructs

This Example describes the design and construction of a family of chimeric Notch receptors. Detailed information for various exemplary receptors of the disclosure can be found in Tables 1 and 2 below.

TABLE 1. This table provides a brief description for each of the chimeric Notch receptors, their corresponding components, as well as corresponding sequence identifiers as set forth in the Sequence Listing. ECD: extracellular domain; N-JMD: N-terminal juxtamembrane domain (i.e., linking polypeptide); TMD: transmembrane domain; STS: stop-transfer-sequence; TF: transcriptional factor.

TABLE 1

| Construct ID | Receptor Description | ECD | N-JMD | TMD | STS | TF | Full sequence |
|---|---|---|---|---|---|---|---|
| pRay050 (miniNotch1) | antiCD19scFv-Notch1deltaNRR-Gal4VP64 | SEQ ID NO: 10 | SEQ ID NO: 19 | SEQ ID NO: 28 | SEQ ID NO: 37 | SEQ ID NO: 46 | SEQ ID NO: 1 |
| pIZ605 (miniNotch2) | antiCD19scFv-Notch3deltaNRR-Gal4VP64 | SEQ ID NO: 11 | SEQ ID NO: 20 | SEQ ID NO: 29 | SEQ ID NO: 38 | SEQ ID NO: 47 | SEQ ID NO: 2 |
| pIZ608 (miniNotch3) | antiCD19scFv-Notch2deltaNRR-Gal4VP64 | SEQ ID NO: 12 | SEQ ID NO: 21 | SEQ ID NO: 30 | SEQ ID NO: 39 | SEQ ID NO: 48 | SEQ ID NO: 3 |
| pIZ611 (miniNotch4) | antiCD19scFv-Notch4deltaECD-Gal4VP64 | SEQ ID NO: 13 | SEQ ID NO: 22 | SEQ ID NO: 31 | SEQ ID NO: 40 | SEQ ID NO: 49 | SEQ ID NO: 4 |
| pIZ621 | antiCD19scFv-Notch1deltaNRR-Notch2STS-Gal4VP64 | SEQ ID NO: 14 | SEQ ID NO: 23 | SEQ ID NO: 32 | SEQ ID NO: 41 | SEQ ID NO: 50 | SEQ ID NO: 5 |

TABLE 1-continued

| Construct ID | Receptor Description | ECD | N-JMD | TMD | STS | TF | Full sequence |
|---|---|---|---|---|---|---|---|
| pIZ627 | antiCD19scFv-Notch2deltaNRR-Notch1STS-Gal4VP64 | SEQ ID NO: 15 | SEQ ID NO: 24 | SEQ ID NO: 33 | SEQ ID NO: 42 | SEQ ID NO: 51 | SEQ ID NO: 6 |
| pIZ640 | antiCD19scFv-Notch4deltaECD-Notch2STS-Gal4VP64 | SEQ ID NO: 16 | SEQ ID NO: 25 | SEQ ID NO: 34 | SEQ ID NO: 43 | SEQ ID NO: 52 | SEQ ID NO: 7 |
| pRay050LaG17 | antiGFPnanobody(LaG17)-Notch1deltaNRR-Gal4VP64 | SEQ ID NO: 17 | SEQ ID NO: 26 | SEQ ID NO: 35 | SEQ ID NO: 44 | SEQ ID NO: 53 | SEQ ID NO: 8 |
| pRay038 | antiCD19scFv-Notch1deltaECD-Gal4VP64 | SEQ ID NO: 18 | SEQ ID NO: 27 | SEQ ID NO: 36 | SEQ ID NO: 45 | SEQ ID NO: 54 | SEQ ID NO: 9 |

TABLE 2. This table provides a brief description for each of the chimeric Notch receptors and the respective components (with components separated by commas). Unless otherwise noted, the entry refers to a protein of human origin. For example, "Notch1, Notch1" indicates that two sequence from Notch1 were fused to generate this protein module.

TABLE 2

| Construct ID | Receptor Description | ECD | N-JMD | TMD | STS | TF |
|---|---|---|---|---|---|---|
| pRay050 (miniNotch1) | SynNotch1 with Notch Regulatory Region (NRR) deleted and remaining fragments fused | CD8α signal peptide, myc-tag, anti-CD19 scFv | Notch1, Notch1 | Notch1 | Notch1 | Gal4, VP64 |
| pIZ605 (miniNotch3) | SynNotch3 with Notch Regulatory Region (NRR) deleted and remaining fragments fused | CD8α signal peptide, myc-tag, anti-CD19 scFv | Notch3, Notch3 | Notch3 | Notch3 | Gal4, VP64 |
| pIZ608 (miniNotch2) | miniNotch2: SynNotch2 with Notch Regulatory Region (NRR) deleted and remaining fragments fused | CD8α signal peptide, myc-tag, anti-CD19 scFv | Notch2, Notch2 | Notch2 | Notch2 | Gal4, VP64 |
| pIZ611 (miniNotch4) | miniNotch4: SynNotch4 with Notch Regulatory Region (NRR) deleted and remaining fragments fused | CD8α signal peptide, myc-tag, anti-CD19 scFv | Notch4 | Notch4 | Notch4 | Gal4, VP64 |
| pIZ621 | miniNotch1 with Notch1 STS replaced by Notch2 STS | CD8α signal peptide, myc-tag, anti-CD19 scFv | Notch1, Notch1 | Notch1 | Notch2 | Gal4, VP64 |
| pIZ627 | miniNotch2 with Notch2 STS replaced by Notch1 STS | CD8α signal peptide, myc-tag, anti-CD19 scFv | Notch2, Notch2 | Notch2 | Notch1 | Gal4, VP64 |
| pIZ640 | miniNotch4 with Notch4 STS replaced by Notch2 STS | CD8α signal peptide, myc-tag, anti-CD19 scFv | Notch4 | Notch4 | Notch2 | Gal4, VP64 |
| pRay050LaG17 | pRay050 with anti-Lag17 binding domain | CD8α signal peptide, myc-tag, LaG17 | Notch1, Notch1 | Notch1 | Notch1 | Gal4, VP64 |
| pRay038 | miniNotch1 with only JMD-TMD-STS (larger NRR deletion) | CD8α signal peptide, myc-tag, anti-CD19 scFv | Notch1 | Notch1 | Notch1 | Gal4, VP64 |

The chimeric receptors described in Tables 1-2 above were built by fusing a single-chain antigen-binding fragment (scFv) recognizing CD19 (Porter D L et al., 2011) or an anti-GFP nanobody (LaG17) to the corresponding receptor scaffold and a synthetic transcriptional regulator GAL4-VP64. For the construction of these receptors, DNA fragments coding for the amino acid sequences provided in Table 1 and Sequence Listing were PCR amplified from synthesized gene fragments or plasmids containing DNA sequence for the indicated protein, and assembled using standard cloning techniques (e.g., overhang PCR, fusion PCR, and In-fusion cloning) with flanking translation start and stop sequences, into a BamHI cloning site of the lentiviral expression vector pHR-SIN-pGK (L. Morsut et al., Cell (2016) 164:780-91; Addgene plasmid #76120).

The transcriptional regulator GAL4-VP64 used in these experiments contained a DNA domain from yeast GAL4 transcription factor fused to an activation domain VP64, which consists of a tetrameric repeat of the minimal activation domain (amino acids 437-447) of the herpes simplex protein VP16. All receptors contained an N-terminal CD8a signal peptide (MALPVTALLLPLALLLHAARP) (SEQ ID NO: 55) for membrane targeting and a myc-tag (EQKLISEEDL) (SEQ ID NO: 56) for suitable determination of surface expression with an antibody conjugated to a fluorescent dye (α-myc A647®, Cell Signaling Technology, Cat #2233). The receptors were each cloned into a modified lentiviral pHR' SIN:CSW vector (KT Roybal et al., Cell 2016 Oct. 6; 167(2):419-32) containing a phosphoglycerate kinase (PGK) promoter for all primary T cell experiments described in Examples 3-4 below.

The pHR' SIN:CSW vector was also modified to produce the response element plasmids. For this purpose, five copies of a target sequence for binding of GAL4 DBD domain (GGAGCACTGTCCTCCGAACG) (SEQ ID NO: 57) were cloned 5' to a minimal pybTATA promoter. Also included in the response element plasmids is a PGK promoter that constitutively drives expression of a yellow fluorescent reporter protein (mCitrine) to suitably identify successfully transduced T cells.

For the construction of all inducible BFP vectors, the coding sequence for a blue fluorescent reporter protein (BFP) was cloned via a BamHI site in the multiple cloning site located 3' to the GAL4 response elements. For the construction of all inducible CAR vectors, the CARs were tagged C-terminally with a green fluorescent reporter protein (GFP) and were cloned via a BamHI site in the multiple cloning site located 3' to the GAL4 response elements. All constructs were cloned via cloning kit (In-Fusion® cloning, Clontech #ST0345) according to the manufacturer's instructions.

Example 2

Primary Human T-Cell Isolation and Culture

This Example describes the isolation and culture of primary human T cells that were subsequently used in various cell transduction experiments described in Example 3 below.

In these experiments, primary CD4$^+$ and CD8$^+$ T cells were isolated from blood after apheresis and enriched by negative selection using human T-cell isolation kits (human CD4$^+$ or CD8$^+$ enrichment cocktail; STEMCELL Technologies Cat #15062 and 15063). Blood was obtained from Blood Centers of the Pacific (San Francisco, Calif.) as approved by the University Institutional Review Board. T cells were cryopreserved in growth medium (RPMI-1640, UCSF cell culture core) with 20% human AB serum (Valley Biomedical Inc., #HP1022) and 10% DMSO. After thawing, T cells were cultured in human T cell medium containing X-VIVO 15 (Lonza #04-418Q), 5% Human AB serum and 10 mM neutralized N-acetyl L-Cysteine (Sigma-Aldrich #A9165) supplemented with 30 units/mL IL-2 (NCI BRB Preclinical Repository) for all experiments.

Example 3

Human T Cells were Stably Transduced with Lentiviral Vectors

The Example describes a general protocol used for lentiviral transduction of human T cells.

Generally, lentiviral vectors pseudo-typed with vesicular stomatitis virus envelope G protein (VSV-G) (pantropic vectors) were produced via transfection of Lenti-X™ 293T cells (Clontech #11131D) with a pHR' SIN:CSW transgene expression vector and the viral packaging plasmids pCMVdR8.91 and pMD2.G using Minis TransIT®-Lenti #MIR 6606). Generally, primary T cells were thawed the same day and, after 24 hours in culture, were stimulated with beads having anti-CD3 and anti-CD28 antibodies bound to the surface (Human T-Activator CD3/CD28 Dynabeads®, Life Technologies #11131D) at a 1:3 cell:bead ratio. At 48 hours, viral supernatant was harvested and the primary T cells were exposed to the virus for 24 hours. At Day 5 post T-cell stimulation, the beads were removed, and the T cells expanded until Day 14 when they were rested and could be used in assays. T cells were sorted for assays with a Beckton Dickinson (BD Biosciences) FACSAria™ II flow cytometer. AND-gate T cells exhibiting basal CAR expression were gated out during sorting.

Example 4

MiniNotch Design, Expression and Activation

Figures 1A, 1B:
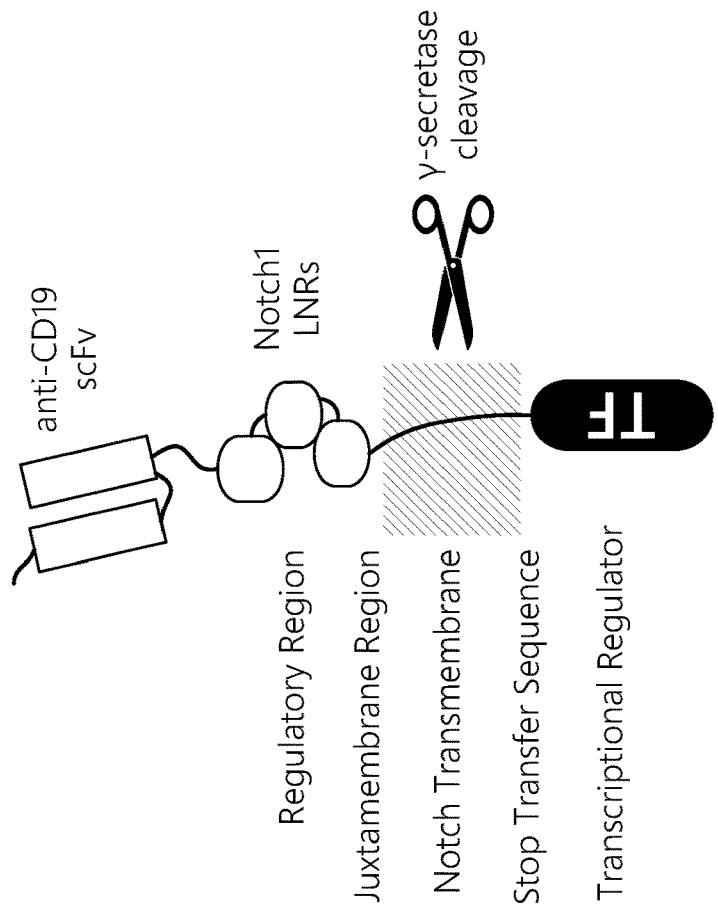
FIGS. 1A-1B schematically illustrate differences between a SynNotch receptor and a chimeric polypeptide of the disclosure.
Figure 2A:
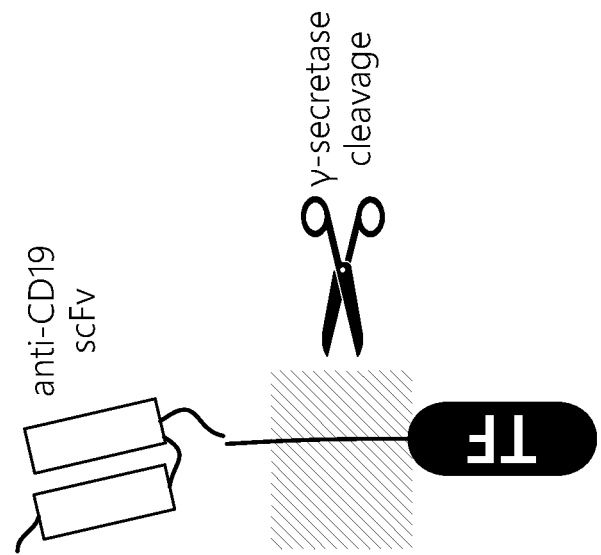
FIGS. 2A-2C schematically summarize the design of MiniNotch receptors, their expression in human CD4+ T-cells, and TCR activation, in comparison with first-generation of SynNotch receptors.
Figure 2A:
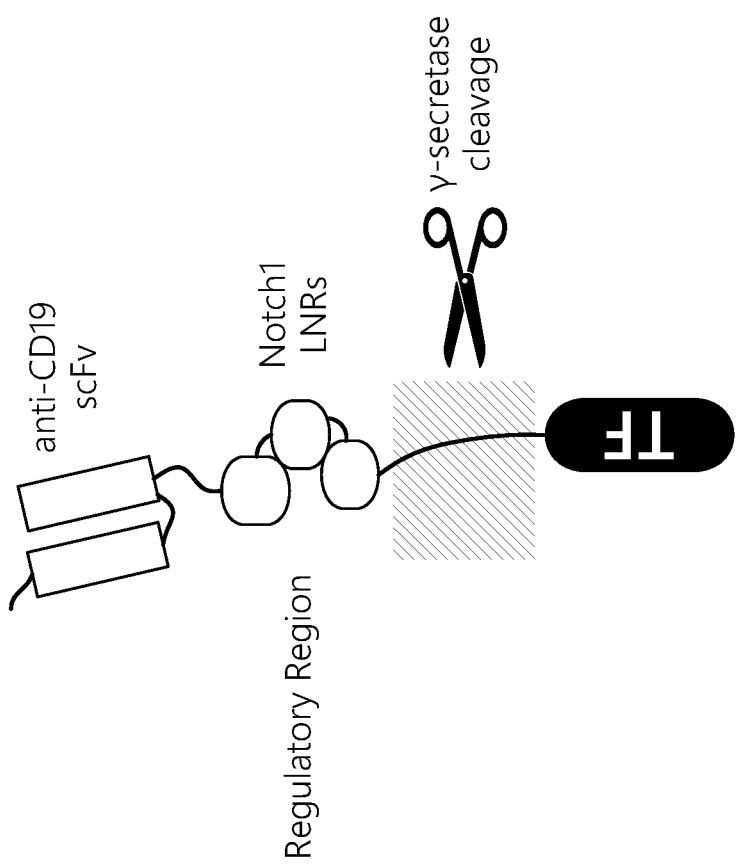
Figure 2B:
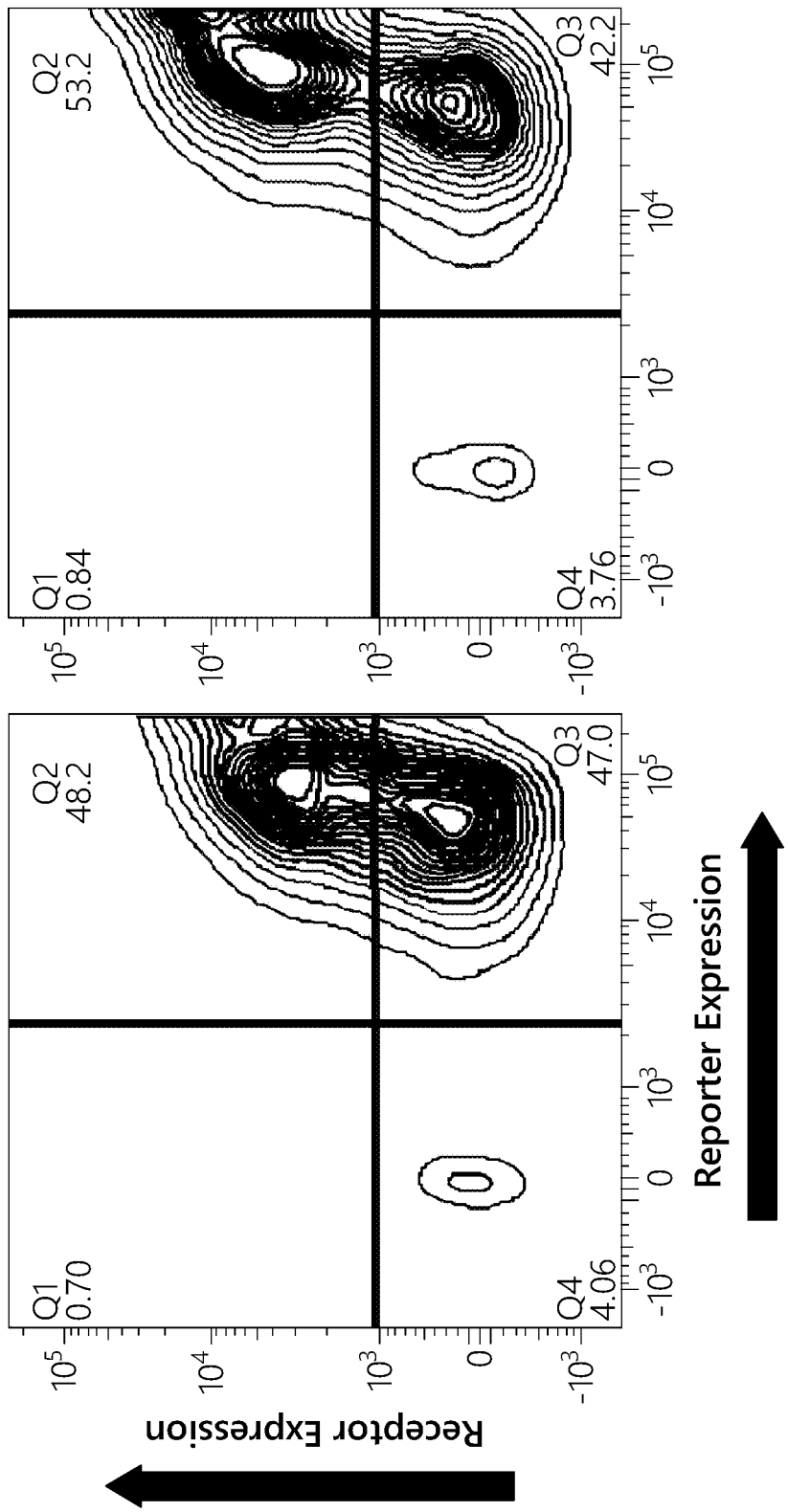
Figure 2C:
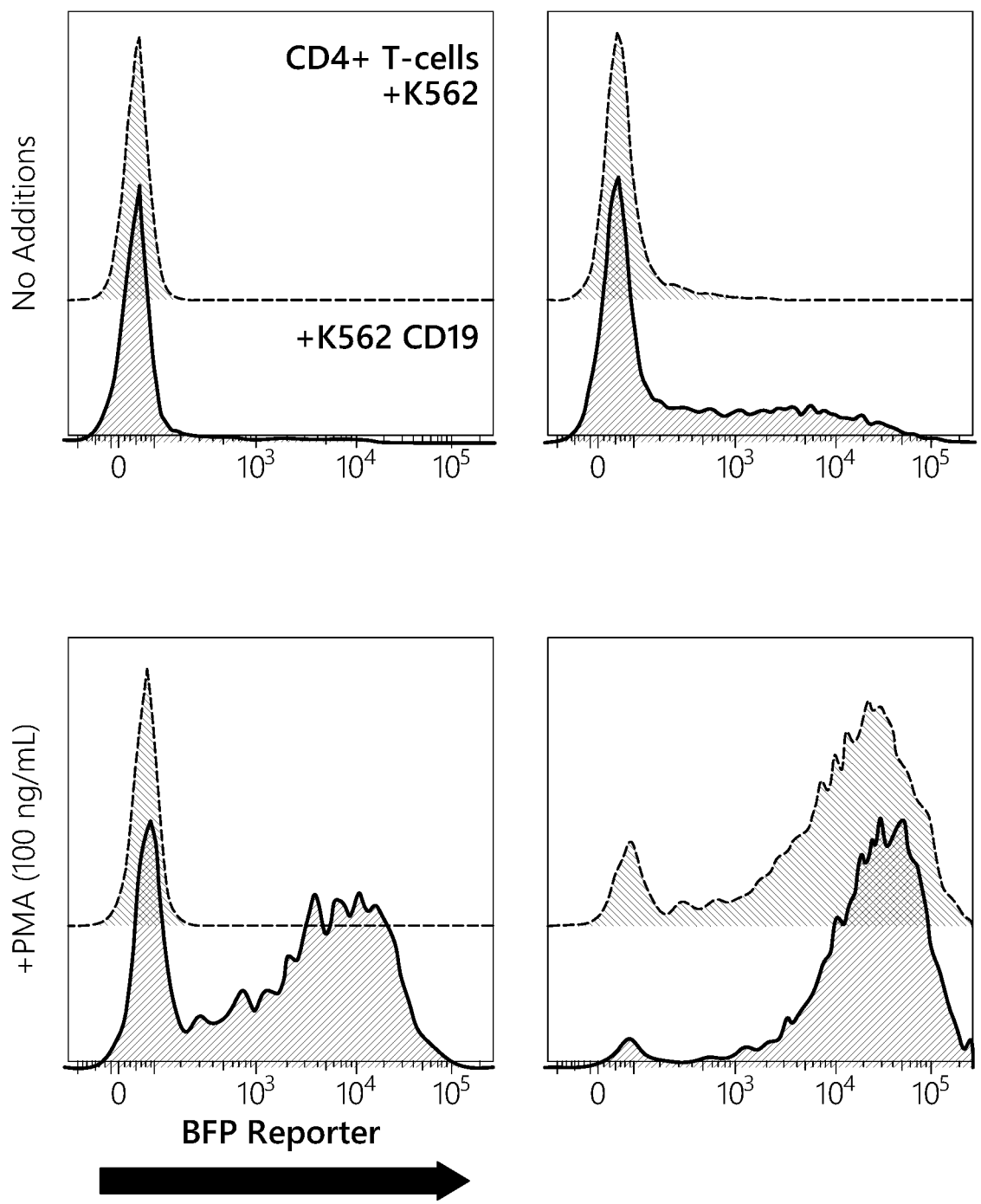

This Example describes the design of MiniNotch receptors, and experiments performed to demonstrate their expression inhuman CD4+ T-cell and TCR activation. FIG. 2B depicts exemplary flow cytometry data showing that MiniNotch receptors are expressed in human CD4+ T-cell. In these experiments, primary human T-cells were activated with anti-CD$^3$/anti-CD28 Dynabeads (Gibco) and transduced with two lentiviral constructs expressing either a Notch receptor or a transcriptional reporter construct. Receptor expression was measured using an AlexaFluor647-tagged anti-myc antibody (Cell Signaling). Reporter expression was measured through a constitutive mCitrine gene carried on the reporter plasmid. Double positive cells were sorted for on Day 5 post initial T-cell stimulation and expanded further for activation testing. FIG. 2C depicts TCR activation by the MiniNotch receptors. The top panel summarizes the results of a receptor activation testing without TCR activation. 1×10$^5$ double positive T-cells expressing anti-CD19 receptors were co-cultured with: 1×10$^5$ K562 cells (blue) or 1×10$^5$ CD19+ K562 cells (red) for 24 hours. Transcriptional activation of an inducible BFP reporter gene was subsequently measured using a Fortessa X-50 (BD Biosciences). The bottom panel summarizes the results of a receptor activation with TCR activation. In this experiment, phorbol 12-myristate 13-acetate (PMA), a DAG analog, was added to co-cultures to simulate PKC signaling).

Example 5

SynNotch Versus MiniNotch Receptor Activation with Concurrent T-Cell Activation This Example describes experiments performed to compare SynNotch activation versus MiniNotch receptor activation performed with concurrent T-cell activation. In these experiments, to simulate T-cell activation, anti-MCAM, anti-CD3 Bi-specific T-cell Engagers (MCAM BiTEs) were used, which activate the T-cell receptor in the presence of K562 cells (FIG. 3). $1 \times 10^5$ double positive T-cells expressing anti-CD19 receptors were co-cultured with: MCAM BiTEs (yellow), $1 \times 10^5$ K562 cells+MCAM BiTEs (blue), or $1 \times 10^5$ CD19+ K562 cells+ MCAM BiTEs (red) for 24 hours. Transcriptional activation of an inducible BFP reporter gene was subsequently measured using a Fortessa X-50 (BD Biosciences).

Example 6

SynNotch Versus MiniNotch Receptor Activation with Co-Expressed CAR

This Example describes experiments where the activation testing of SynNotch and MiniNotch receptor was conducted with co-expressed CAR. In these experiments, SynNotch1 and miniNotch1 were co-transduced with a CAR targeting ALPPL2 (FIG. 4A). As shown in FIG. 4B, $1 \times 10^5$ double positive T-cells expressing anti-CD19 SynNotch or miniNotch and anti-ALPPL2 CARs were co-cultured with: blank sample (dark green), $1 \times 10^5$ K562 cells (light green), $1 \times 10^5$ CD19+K562 cells (orange), $1 \times 10^5$ ALPPL2+K562 cells (blue), or $1 \times 10^5$ CD19+K562 cells and $1 \times 10^5$ ALPPL2+ K562 cells (red) for 24 hours. Transcriptional activation of an inducible BFP reporter gene was subsequently measured using a Fortessa X-50 (BD Biosciences).

Example 7

Testing of MiniNotch Receptors with Other Ligand Recognition Domains

This Example describes experiments performed to demonstrate that other ligand recognition domains, in addition to the anti-CD19 scFV, can also be used. As shown illustrated in FIG. 5A, the anti-GFP LagG17 nanobody and the anti-ALPPL2 scFV can also be used. FIG. 5B summarizes the results of activation testing with additional ligand recognition domains. In these experiments, primary CD8+ human T-cells were activated with anti-CD3/anti-CD28 Dynabeads (Gibco) and transduced with two lentiviral constructs expressing either a receptor or a transcriptional reporter construct. Receptor expression was measured using an AlexaFluor647-tagged anti-myc antibody (Cell Signaling). Reporter expression was measured through a constitutive fluorescent protein gene found on the reporter plasmid. Double positive cells were sorted for on Day 5 post initial T-cell stimulation and expanded further for activation testing.

For testing, $1 \times 10^5$ double positive CD8+ T-cells expressing anti-GFP or anti-ALPPL2 miniNotch are co-cultured with: nothing (orange), $1 \times 10^5$ K562 cells (blue), or $1 \times 10^5$ surface GFP K562 cells/ALPPL2+ K562 cells (red) for 24 hours. Transcriptional activation of an inducible BFP reporter gene was subsequently measured using a Fortessa X-50 (BD Biosciences).

Example 8

Stimulation of Primary T Cells In Vitro

This Example describes experiments performed to demonstrate the stimulation of primary T cells in vitro by the chimeric miniNotch polypeptides described herein.

For all in vitro T-cell stimulations, $1 \times 10^5$ T cells were co-cultured with sender cells at a 1:1 ratio in flat bottom 96-well tissue culture plates. The cultures were analyzed at 24 hours for reporter activation with a BD Fortessa™ X-50. All flow cytometry analysis was performed in FlowJo™ software (TreeStar, Inc.).

Each of the miniNotch constructs pRay050 (miniNotch1), pIZ605 (miniNotch2), pIZ608 (miniNotch3), pIZ611 (miniNotch4) were able to stimulate primary T cells as determined by expression of BFP reporter gene.

The results of this experiment is summarized in Table 3 below.

TABLE 3

| Receptor | "Switch-like" | Sensitive to T-cell activation |
| --- | --- | --- |
| MiniNotch-1 | Yes | Yes |
| MiniNotch-2 | No-Always ON | No |
| MiniNotch-3 | Yes-noisier than MiniNotch-1 | No |
| MiniNotch-4 | Yes-noisier than MiniNotch-1 | No |

It was also observed that (1) the dipeptide -Gln-His-(QH) was not found in the miniNotch1 construct but in the miniNotch1-QH construct, which is identical the pRay050 construct with the exception of a STS having two amino acid residues longer in length, and that (2) addition of "QH" dipeptide to the STS of the miniNotch1 mildly improves receptor signal.

Example 9

This Example describes the generation of myelogenous leukemia cells expressing CD19 at equivalent levels as Daudi tumors.

The cancer cell lines used were K562 myelogenous leukemia cells (ATCC #CCL-243) and Daudi B cell lymphoblasts (ATCC #CCL-213). The K562 cells were lentivirally transduced to stably express human CD19 at equivalent levels as Daudi tumors. CD19 levels were determined by staining the cells with α-CD19 APC (Biolegend® #302212). All cell lines were sorted for expression of the transgenes.

Example 10

Generation of Reporter Jurkat T Cells

This Example describes the generation of reporter Jurkat T cells that were subsequent used for the screening of transmembrane domains (TMD) and/or stop-transfer sequences (STS). In the present disclosure, these reporter Jurkat cells were used for all experiments performed for miniNotch receptors in Jurkat cells.

In these experiments, E6-1 Jurkat T cells (ATCC #TIB-152) were lentivirally transduced with a reporter plasmid carrying an inducible BFP reporter gene and a constitutive mCitrine reporter gene, as described previously (Roybal K T et al., *Cell*, 164:1-10, 2016). Reporter-positive Jurkat cells were sorted for mCitrine expression using a Beckton Dickinson (BD Biosciences) FACSAria™ II flow cytometer and expanded.

Lentiviral particles were produced with the receptor transgene expression vector as described previously (Morsut et al., Cell (2016) 164:780-91). Reporter-positive Jurkat cells were transduced with individual receptors and expanded for experimentation in 96 well plates.

Example 11

This Example describes experiments performed to demonstrate the stimulation of Jurkat T cells in vitro by the chimeric miniNotch polypeptides described herein.

For all in vitro Jurkat T-cell stimulations, $1 \times 10^5$ Jurkat T cells were co-cultured with sender cells at a 1:1 ratio in flat bottom 96-well tissue culture plates. The cultures were analyzed at 24 hours for receptor (myc) expression and reporter activation with a BD Fortessa X-50™. All flow cytometry analysis was performed in FlowJo™ software (TreeStar, Inc.). Receptors with positive TMD and STS hits, along with a selection of negative hits, were confirmed in human primary T-cells using the above protocols.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

Example 12

This Example describes the results of experiments performed to demonstrate receptor activation with co-expressed CAR. FIG. 6A shows diagrams for activating an exemplary Mini Notch receptor ("Mini synNotch1") vs. a SynNotch1 receptor by a co-expressed CAR targeting ALPPL2. As shown in FIG. 6B, $1 \times 10^5$ double positive T-cells expressing anti-CD19 receptors were co-cultured with no additions (top trace), $1 \times 10^5$ ALPPL2+K562 cells (second trace from top), $1 \times 10^5$ CD19+K562 cells (third trace from top), or $1 \times 10^5$ ALPPL2+CD19+K562 cells (bottom trace). Transcriptional activation of an inducible BFP reporter gene was subsequently measured using a Fortessa X-50 (BD Biosciences). Activation using murine and human original synNotch constructs were included for comparison.

Example 13

This Example describes the results of experiments as described herein for some chimeric Notch receptors provided herein and described in Table 1.

TABLE 4

| Construct ID | Receptor Description | Experiment Results for Activity |
| --- | --- | --- |
| pRay050 (miniNotch1) | antiCD19scFv-Notch1deltaNRR-Gal4VP64 | Noisy background at sorting; Noise decreased with T-cell rest; Activated with ligand; Sensitive to T-cell activation. |
| pIZ605 (miniNotch2) | antiCD19scFv-Notch3deltaNRR-Gal4VP64 | Noisier background than miniNotch1 but activated with target cells; Not sensitive to T-cell activation. |
| pIZ608 (miniNotch3) | antiCD19scFv-Notch2deltaNRR-Gal4VP64 | Always on. |
| pIZ611 (miniNotch4) | antiCD19scFv-Notch4deltaECD-Gal4VP64 | Cleaner background at sorting but poor activation; Not sensitive to T-cell activation. |
| pIZ621 | antiCD19scFv-Notch1deltaNRR-Notch2STS-Gal4VP64 | Notch2 STS roughly doubled background noise and signal of pRay050. |
| pIZ627 | antiCD19scFv-Notch2deltaNRR-Notch1STS-Gal4VP64 | Notch1 STS strongly reduced noise of miniNotch2; A switch-like receptor. |
| pIZ640 | antiCD19scFv-Notch4deltaECD-Notch2STS-Gal4VP64 | Notch2 STS strongly improved activation of miniNotch4; Behaved like pIZ343. |
| pRay050LaG17 | antiGFPnanobody (LaG17)-Notch1deltaNRR-Gal4VP64 | Activated similarly to pRay050 but in response to GFP ligand. |
| pRay038 | antiCD19scFv-Notch1deltaECD-Gal4VP64 | Activated with ligand; Not sensitive to TCR signaling. |

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

REFERENCES

Dudani J. S., Warren A. D., and Bhatia S. N., Harnessing Protease Activity to Improve Cancer Care. Annu. Rev. Cancer Biol. 2018. 2:353-76.

David L. Porter, M.D., Bruce L. Levine, Ph.D., Michael Kalos, Ph.D., Adam Bagg, M.D., and Carl H. June, M.D. Chimeric Antigen Receptor—Modified T Cells in Chronic Lymphoid Leukemia. N. Engl J Med. 2011 Aug. 25; 365(8): 725-733.

Morsut L, Roybal K T, Xiong X, Gordley R M, Coyle S M, Thomson M, and Lim W A. Engineering Customized Cell Sensing and Response Behaviors Using Synthetic Notch Receptors. Cell. 2016 February 11; 164(4): 780-791.

Naso M F, Tomkowicz B, Perry W L 3rd, Strohl W R. Adeno-Associated Virus (AAV) as a Vector for Gene Therapy. BioDrugs. 2017; 31(4):317-334.

Nasri M, Karimi A, Allahbakhshian Farsani M. Production, purification and titration of a lentivirus-based vector for gene delivery purposes. Cytotechnology. 2014; 66(6): 1031-1038.

Roybal K T, Jasper Z. Williams, Leonardo Morsut, Levi J. Rupp, Isabel Kolinko, Joseph H. Choe, Whitney J. Walker, Krista A. McNally, and Wendell A. Lim. Engineering T cells with Customized Therapeutic Response Programs Using Synthetic Notch Receptors. Cell. 2016 Oct. 6; 167(2): 419-432.

Samulski and Muzyczka (2014). AAV-Mediated Gene Therapy for Research and Therapeutic Purposes. Annu. Rev. Virol. 1, 427.

Sakuma, et al. (2012). Lentiviral vectors: basic to translational. Biochem. J. 443, 603.

Watson D. J., Wolfe J. H. Viral vectors for gene therapy: methods and protocols. Totowa, N.J., USA: Humana Press; 2003. pp. 383-404.

What is claimed is:

1. A chimeric polypeptide comprising, from N-terminus to C-terminus:
   a) an extracellular ligand-binding domain comprising a single chain variable fragment (scFv) having a binding affinity for a selected ligand;
   b) a linking polypeptide comprising the sequence of SEQ ID NO: 19;
   c) a transmembrane domain from a human Notch receptor comprising one or more ligand-inducible proteolytic cleavage sites; and
   d) an intracellular domain comprising a transcriptional regulator, wherein binding of the selected ligand to the extracellular ligand-binding domain induces cleavage at the ligand-inducible proteolytic cleavage site disposed between the transcriptional regulator and the linking polypeptide,
   and wherein the chimeric polypeptide does not comprise a LIN-12-Notch repeat (LNR) nor a heterodimerization domain (HD) of a Notch receptor.

2. The chimeric polypeptide of claim 1, wherein the transmembrane domain further comprises a stop-transfer-sequence.

3. The chimeric polypeptide of claim 1, wherein the scFv is capable of binding to a ligand on the surface of a cell.

4. The chimeric polypeptide of claim 3, wherein the cell is a human cell.

5. The chimeric polypeptide of claim 3, wherein the cell is a tumor cell.

6. The chimeric polypeptide of claim 1, wherein the ligand comprises a protein or a carbohydrate.

7. The chimeric polypeptide of claim 1, wherein the ligand is selected from the group consisting of CD19, CD59, CD66, CD73, CD80 (B7.1), CD86 (B7.2), CD94, CD134, CD140 (PDGFR4), CD152, CD154, CD158, CD178, CD181 (CXCR1), CD182 (CXCR2), CD183 (CXCR3), CD246, CD273 (PD-L2), CD274 (PD-L1), CD295, CD340 (HER2), FGFR2, CEA, AFP, CA125, MUC-1, MAGE, alkaline phosphatase, placental-like 2 (ALPPL2), green fluorescent protein (GFP), enhanced green fluorescent Protein (eGFP), and signal regulatory protein α (SIRPα).

8. The chimeric polypeptide of claim 1, wherein the ligand is selected from cell surface receptors, adhesion proteins, integrins, mucins, lectins, tumor associated antigens, and tumor-specific antigens.

9. The chimeric polypeptide of claim 1, wherein the ligand is a tumor-associated antigen selected from the group consisting of CD19, B7H3 (CD276), BCMA, CD123, CD171, CD179a, CD20, CD213A2, CD22, CD24, CD246, CD272, CD30, CD33, CD38, CD44v6, CD46, CD71, CD97, CEA, CLDN6, CLECL1, CS-1, EGFR, EGFRvIII, ELF2M, EpCAM, EphA2, Ephrin B2, FAP, FLT3, GD2, GD3, GM3, GPRC5D, HER2 (ERBB2/neu), IGLL1, IL-11Ra, KIT (CD117), MUC1, NCAM, PAP, PDGFR-beta, PRSS21, PSCA, PSMA, ROR1, SSEA-4, TAG72, TEM1/CD248, TEM7R, TSHR, VEGFR2, BCMA (CD269), ALPPL2, ALPI, citrullinated vimentin, cMet, and Axl.

10. The chimeric polypeptide of claim 1, wherein the ligand-inducible proteolytic cleavage site is a gamma-secretase cleavage site.

11. The chimeric polypeptide of claim 1, wherein the intracellular domain comprises a nuclear localization sequence and a transcriptional regulator sequence selected from the group consisting of Gal4-VP16, Gal4-VP64, tetR-VP64, ZFHD1-VP64, Gal4-KRAB, and HAP1-VP16.

12. The chimeric polypeptide of claim 1, further comprising a signal sequence, a detectable label, a tumor-specific cleavage site, a disease-specific cleavage site, and combinations thereof.

13. A recombinant cell comprising: a chimeric polypeptide according to claim 1.

14. The chimeric polypeptide of claim 1, wherein the transmembrane domain is from human Notch 1 receptor.

15. The chimeric polypeptide of claim 1, wherein the transmembrane domain is from human Notch 2 receptor.

16. The chimeric polypeptide of claim 1, wherein the transmembrane domain is from human Notch 3 receptor.

17. The chimeric polypeptide of claim 1, wherein the transmembrane domain is from human Notch 4 receptor.

* * * * *

SEQUENCE LISTING

<160> NUMBER OF SEQ ID NOS: 65

<210> SEQ ID NO 1
<211> LENGTH: 543
<212> TYPE: PRT
<213> ORGANISM: Artificial sequence
<220> FEATURE:
<223> OTHER INFORMATION: Synthetic construct

<400> SEQUENCE: 1

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Ile Leu Asp Tyr Ser Phe Gly Gly Gly Ala Gly Arg Asp Ile Pro
        275                 280                 285

Pro Pro Leu Ile Glu Glu Thr Val Pro Pro Pro Ala Gln Leu
    290                 295                 300

His Phe Met Tyr Val Ala Ala Ala Phe Val Leu Leu Phe Phe Val
305                 310                 315                 320

Gly Cys Gly Val Leu Leu Ser Arg Lys Arg Arg Met Lys Leu Leu
                325                 330                 335

Ser Ser Ile Glu Gln Ala Cys Asp Ile Cys Arg Leu Lys Lys Leu Lys
            340                 345                 350

Cys Ser Lys Glu Lys Pro Lys Cys Ala Lys Cys Leu Lys Asn Asn Trp

```
                355                 360                 365
Glu Cys Arg Tyr Ser Pro Lys Thr Lys Arg Ser Pro Leu Thr Arg Ala
370                 375                 380

His Leu Thr Glu Val Glu Ser Arg Leu Glu Arg Leu Glu Gln Leu Phe
385                 390                 395                 400

Leu Leu Ile Phe Pro Arg Glu Asp Leu Asp Met Ile Leu Lys Met Asp
                405                 410                 415

Ser Leu Gln Asp Ile Lys Ala Leu Leu Thr Gly Leu Phe Val Gln Asp
                420                 425                 430

Asn Val Asn Lys Asp Ala Val Thr Asp Arg Leu Ala Ser Val Glu Thr
            435                 440                 445

Asp Met Pro Leu Thr Leu Arg Gln His Arg Ile Ser Ala Thr Ser Ser
        450                 455                 460

Ser Glu Glu Ser Ser Asn Lys Gly Gln Arg Gln Leu Thr Val Ser Ala
465                 470                 475                 480

Ala Ala Gly Gly Ser Gly Gly Ser Gly Gly Ser Asp Ala Leu Asp Asp
                485                 490                 495

Phe Asp Leu Asp Met Leu Gly Ser Asp Ala Leu Asp Asp Phe Asp Leu
                500                 505                 510

Asp Met Leu Gly Ser Asp Ala Leu Asp Asp Phe Asp Leu Asp Met Leu
            515                 520                 525

Gly Ser Asp Ala Leu Asp Asp Phe Asp Leu Asp Met Leu Gly Ser
        530                 535                 540

<210> SEQ ID NO 2
<211> LENGTH: 536
<212> TYPE: PRT
<213> ORGANISM: Artificial sequence
<220> FEATURE:
<223> OTHER INFORMATION: Synthetic construct

<400> SEQUENCE: 2

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Ser Gly
        130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
```

```
                180             185             190
Pro Pro Arg Lys Gly Leu Glu Trp Leu Gly Val Ile Trp Gly Ser Glu
            195                 200                 205
Thr Thr Tyr Tyr Asn Ser Ala Leu Lys Ser Arg Leu Thr Ile Ile Lys
            210                 215                 220
Asp Asn Ser Lys Ser Gln Val Phe Leu Lys Met Asn Ser Leu Gln Thr
225                 230                 235                 240
Asp Asp Thr Ala Ile Tyr Tyr Cys Ala Lys His Tyr Tyr Gly Gly
                245                 250                 255
Ser Tyr Ala Met Asp Tyr Trp Gly Gln Gly Thr Ser Val Thr Val Ser
            260                 265                 270
Ser Ala Pro Ala Ala Pro Glu Val Ser Glu Pro Arg Pro Leu
            275                 280                 285
Glu Pro Pro Glu Pro Ser Val Pro Leu Leu Pro Leu Leu Val Ala Gly
            290                 295                 300
Ala Val Leu Leu Leu Val Ile Leu Val Leu Gly Val Met Val Ala Arg
305                 310                 315                 320
Arg Lys Arg Glu His Met Lys Leu Leu Ser Ser Ile Glu Gln Ala Cys
                325                 330                 335
Asp Ile Cys Arg Leu Lys Lys Leu Lys Cys Ser Lys Glu Lys Pro Lys
                340                 345                 350
Cys Ala Lys Cys Leu Lys Asn Asn Trp Glu Cys Arg Tyr Ser Pro Lys
            355                 360                 365
Thr Lys Arg Ser Pro Leu Thr Arg Ala His Leu Thr Glu Val Glu Ser
            370                 375                 380
Arg Leu Glu Arg Leu Glu Gln Leu Phe Leu Leu Ile Phe Pro Arg Glu
385                 390                 395                 400
Asp Leu Asp Met Ile Leu Lys Met Asp Ser Leu Gln Asp Ile Lys Ala
                405                 410                 415
Leu Leu Thr Gly Leu Phe Val Gln Asp Asn Val Asn Lys Asp Ala Val
            420                 425                 430
Thr Asp Arg Leu Ala Ser Val Glu Thr Asp Met Pro Leu Thr Leu Arg
            435                 440                 445
Gln His Arg Ile Ser Ala Thr Ser Ser Ser Glu Glu Ser Ser Asn Lys
            450                 455                 460
Gly Gln Arg Gln Leu Thr Val Ser Ala Ala Gly Gly Ser Gly Gly
465                 470                 475                 480
Ser Gly Gly Ser Asp Ala Leu Asp Asp Phe Asp Leu Asp Met Leu Gly
                485                 490                 495
Ser Asp Ala Leu Asp Asp Phe Asp Leu Asp Met Leu Gly Ser Asp Ala
            500                 505                 510
Leu Asp Asp Phe Asp Leu Asp Met Leu Gly Ser Asp Ala Leu Asp Asp
            515                 520                 525
Phe Asp Leu Asp Met Leu Gly Ser
530                 535

<210> SEQ ID NO 3
<211> LENGTH: 533
<212> TYPE: PRT
<213> ORGANISM: Artificial sequence
<220> FEATURE:
<223> OTHER INFORMATION: Synthetic construct

<400> SEQUENCE: 3

Met Ala Leu Pro Val Thr Ala Leu Leu Leu Pro Leu Ala Leu Leu Leu
```

```
1               5                   10                  15
His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
            50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
            165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
            210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
            260                 265                 270

Ser Leu Tyr Thr Ala Pro Pro Ser Thr Pro Ala Thr Ser Leu Thr
            275                 280                 285

Pro Glu Arg Thr Gln Leu Leu Tyr Leu Leu Ala Val Ala Val Val Ile
            290                 295                 300

Ile Leu Phe Ile Ile Leu Leu Gly Val Ile Met Ala Lys Arg Lys Arg
305                 310                 315                 320

Lys His Met Lys Leu Leu Ser Ser Ile Glu Gln Ala Cys Asp Ile Cys
            325                 330                 335

Arg Leu Lys Lys Leu Lys Cys Ser Lys Glu Lys Pro Lys Cys Ala Lys
            340                 345                 350

Cys Leu Lys Asn Asn Trp Glu Cys Arg Tyr Ser Pro Lys Thr Lys Arg
            355                 360                 365

Ser Pro Leu Thr Arg Ala His Leu Thr Glu Val Glu Ser Arg Leu Glu
            370                 375                 380

Arg Leu Glu Gln Leu Phe Leu Leu Ile Phe Pro Arg Glu Asp Leu Asp
385                 390                 395                 400

Met Ile Leu Lys Met Asp Ser Leu Gln Asp Ile Lys Ala Leu Leu Thr
            405                 410                 415

Gly Leu Phe Val Gln Asp Asn Val Asn Lys Asp Ala Val Thr Asp Arg
            420                 425                 430
```

```
Leu Ala Ser Val Glu Thr Asp Met Pro Leu Thr Leu Arg Gln His Arg
            435                 440                 445

Ile Ser Ala Thr Ser Ser Glu Glu Ser Ser Asn Lys Gly Gln Arg
        450                 455                 460

Gln Leu Thr Val Ser Ala Ala Gly Ser Gly Gly Ser Gly Gly
465                 470                 475                 480

Ser Asp Ala Leu Asp Asp Phe Asp Leu Asp Met Leu Gly Ser Asp Ala
                485                 490                 495

Leu Asp Asp Phe Asp Leu Asp Met Leu Gly Ser Asp Ala Leu Asp Asp
            500                 505                 510

Phe Asp Leu Asp Met Leu Gly Ser Asp Ala Leu Asp Asp Phe Asp Leu
            515                 520                 525

Asp Met Leu Gly Ser
        530

<210> SEQ ID NO 4
<211> LENGTH: 531
<212> TYPE: PRT
<213> ORGANISM: Artificial sequence
<220> FEATURE:
<223> OTHER INFORMATION: Synthetic construct

<400> SEQUENCE: 4

Met Ala Leu Pro Val Thr Ala Leu Leu Leu Pro Leu Ala Leu Leu Leu
1               5                  10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255
```

```
Ser Tyr Ala Met Asp Tyr Trp Gly Gln Gly Thr Ser Val Thr Val Ser
            260                 265                 270

Ser Val His Pro His Ala Gly Thr Ala Pro Pro Ala Asn Gln Leu Pro
            275                 280                 285

Trp Pro Val Leu Cys Ser Pro Val Ala Gly Val Ile Leu Leu Ala Leu
            290                 295                 300

Gly Ala Leu Leu Val Leu Gln Leu Ile Arg Arg Arg Arg Arg Glu His
305                 310                 315                 320

Met Lys Leu Leu Ser Ser Ile Glu Gln Ala Cys Asp Ile Cys Arg Leu
            325                 330                 335

Lys Lys Leu Lys Cys Ser Lys Glu Lys Pro Lys Cys Ala Lys Cys Leu
            340                 345                 350

Lys Asn Asn Trp Glu Cys Arg Tyr Ser Pro Lys Thr Lys Arg Ser Pro
            355                 360                 365

Leu Thr Arg Ala His Leu Thr Glu Val Glu Ser Arg Leu Glu Arg Leu
            370                 375                 380

Glu Gln Leu Phe Leu Leu Ile Phe Pro Arg Glu Asp Leu Asp Met Ile
385                 390                 395                 400

Leu Lys Met Asp Ser Leu Gln Asp Ile Lys Ala Leu Leu Thr Gly Leu
            405                 410                 415

Phe Val Gln Asp Asn Val Asn Lys Asp Ala Val Thr Asp Arg Leu Ala
            420                 425                 430

Ser Val Glu Thr Asp Met Pro Leu Thr Leu Arg Gln His Arg Ile Ser
            435                 440                 445

Ala Thr Ser Ser Ser Glu Glu Ser Ser Asn Lys Gly Gln Arg Gln Leu
            450                 455                 460

Thr Val Ser Ala Ala Gly Gly Ser Gly Ser Gly Gly Ser Asp
465                 470                 475                 480

Ala Leu Asp Asp Phe Asp Leu Asp Met Leu Gly Ser Asp Ala Leu Asp
            485                 490                 495

Asp Phe Asp Leu Asp Met Leu Gly Ser Asp Ala Leu Asp Asp Phe Asp
            500                 505                 510

Leu Asp Met Leu Gly Ser Asp Ala Leu Asp Asp Phe Asp Leu Asp Met
            515                 520                 525

Leu Gly Ser
    530

<210> SEQ ID NO 5
<211> LENGTH: 544
<212> TYPE: PRT
<213> ORGANISM: Artificial sequence
<220> FEATURE:
<223> OTHER INFORMATION: Synthetic construct

<400> SEQUENCE: 5

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80
```

```
His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
            260                 265                 270

Ser Ile Leu Asp Tyr Ser Phe Gly Gly Ala Gly Arg Asp Ile Pro
        275                 280                 285

Pro Pro Leu Ile Glu Glu Thr Val Glu Pro Pro Pro Ala Gln Leu
290                 295                 300

His Phe Met Tyr Val Ala Ala Ala Phe Val Leu Leu Phe Phe Val
305                 310                 315                 320

Gly Cys Gly Val Leu Leu Ser Lys Arg Lys Arg Lys His Met Lys Leu
                325                 330                 335

Leu Ser Ser Ile Glu Gln Ala Cys Asp Ile Cys Arg Leu Lys Lys Leu
            340                 345                 350

Lys Cys Ser Lys Glu Lys Pro Lys Cys Ala Lys Cys Leu Lys Asn Asn
        355                 360                 365

Trp Glu Cys Arg Tyr Ser Pro Lys Thr Lys Arg Ser Pro Leu Thr Arg
370                 375                 380

Ala His Leu Thr Glu Val Glu Ser Arg Leu Glu Arg Leu Glu Gln Leu
385                 390                 395                 400

Phe Leu Leu Ile Phe Pro Arg Glu Asp Leu Asp Met Ile Leu Lys Met
                405                 410                 415

Asp Ser Leu Gln Asp Ile Lys Ala Leu Leu Thr Gly Leu Phe Val Gln
            420                 425                 430

Asp Asn Val Asn Lys Asp Ala Val Thr Asp Arg Leu Ala Ser Val Glu
        435                 440                 445

Thr Asp Met Pro Leu Thr Leu Arg Gln His Arg Ile Ser Ala Thr Ser
450                 455                 460

Ser Ser Glu Glu Ser Ser Asn Lys Gly Gln Arg Gln Leu Thr Val Ser
465                 470                 475                 480

Ala Ala Ala Gly Gly Ser Gly Gly Ser Gly Gly Ser Asp Ala Leu Asp
                485                 490                 495
```

```
Asp Phe Asp Leu Asp Met Leu Gly Ser Asp Ala Leu Asp Phe Asp
                500                 505                 510

Leu Asp Met Leu Gly Ser Asp Ala Leu Asp Phe Asp Leu Asp Met
            515                 520                 525

Leu Gly Ser Asp Ala Leu Asp Asp Phe Asp Leu Asp Met Leu Gly Ser
        530                 535                 540

<210> SEQ ID NO 6
<211> LENGTH: 532
<212> TYPE: PRT
<213> ORGANISM: Artificial sequence
<220> FEATURE:
<223> OTHER INFORMATION: Synthetic construct

<400> SEQUENCE: 6

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Leu Tyr Thr Ala Pro Pro Ser Thr Pro Pro Ala Thr Ser Leu Thr
        275                 280                 285

Pro Glu Arg Thr Gln Leu Leu Tyr Leu Leu Ala Val Ala Val Val Ile
    290                 295                 300

Ile Leu Phe Ile Ile Leu Leu Gly Val Ile Met Ala Arg Lys Arg Arg
305                 310                 315                 320
```

```
Arg Met Lys Leu Leu Ser Ser Ile Glu Gln Ala Cys Asp Ile Cys Arg
            325                 330                 335

Leu Lys Lys Leu Lys Cys Ser Lys Glu Lys Pro Lys Cys Ala Lys Cys
        340                 345                 350

Leu Lys Asn Asn Trp Glu Cys Arg Tyr Ser Pro Lys Thr Lys Arg Ser
        355                 360                 365

Pro Leu Thr Arg Ala His Leu Thr Glu Val Glu Ser Arg Leu Glu Arg
    370                 375                 380

Leu Glu Gln Leu Phe Leu Ile Phe Pro Arg Glu Asp Leu Asp Met
385                 390                 395                 400

Ile Leu Lys Met Asp Ser Leu Gln Asp Ile Lys Ala Leu Leu Thr Gly
            405                 410                 415

Leu Phe Val Gln Asp Asn Val Asn Lys Asp Ala Val Thr Asp Arg Leu
        420                 425                 430

Ala Ser Val Glu Thr Asp Met Pro Leu Thr Leu Arg Gln His Arg Ile
        435                 440                 445

Ser Ala Thr Ser Ser Ser Glu Glu Ser Ser Asn Lys Gly Gln Arg Gln
    450                 455                 460

Leu Thr Val Ser Ala Ala Ala Gly Gly Ser Gly Gly Ser Gly Gly Ser
465                 470                 475                 480

Asp Ala Leu Asp Asp Phe Asp Leu Asp Met Leu Gly Ser Asp Ala Leu
                485                 490                 495

Asp Asp Phe Asp Leu Asp Met Leu Gly Ser Asp Ala Leu Asp Asp Phe
            500                 505                 510

Asp Leu Asp Met Leu Gly Ser Asp Ala Leu Asp Asp Phe Asp Leu Asp
        515                 520                 525

Met Leu Gly Ser
    530

<210> SEQ ID NO 7
<211> LENGTH: 530
<212> TYPE: PRT
<213> ORGANISM: Artificial sequence
<220> FEATURE:
<223> OTHER INFORMATION: Synthetic construct

<400> SEQUENCE: 7

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140
```

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
            260                 265                 270

Ser Val His Pro His Ala Gly Thr Ala Pro Ala Asn Gln Leu Pro
        275                 280                 285

Trp Pro Val Leu Cys Ser Pro Val Ala Gly Val Ile Leu Leu Ala Leu
290                 295                 300

Gly Ala Leu Leu Val Leu Gln Leu Ile Lys Arg Lys Arg Lys His Met
305                 310                 315                 320

Lys Leu Leu Ser Ser Ile Glu Gln Ala Cys Asp Ile Cys Arg Leu Lys
                325                 330                 335

Lys Leu Lys Cys Ser Lys Glu Lys Pro Lys Cys Ala Lys Cys Leu Lys
            340                 345                 350

Asn Asn Trp Glu Cys Arg Tyr Ser Pro Lys Thr Lys Arg Ser Pro Leu
        355                 360                 365

Thr Arg Ala His Leu Thr Glu Val Glu Ser Arg Leu Glu Arg Leu Glu
    370                 375                 380

Gln Leu Phe Leu Leu Ile Phe Pro Arg Glu Asp Leu Asp Met Ile Leu
385                 390                 395                 400

Lys Met Asp Ser Leu Gln Asp Ile Lys Ala Leu Leu Thr Gly Leu Phe
                405                 410                 415

Val Gln Asp Asn Val Asn Lys Asp Ala Val Thr Asp Arg Leu Ala Ser
            420                 425                 430

Val Glu Thr Asp Met Pro Leu Thr Leu Arg Gln His Arg Ile Ser Ala
        435                 440                 445

Thr Ser Ser Ser Glu Glu Ser Ser Asn Lys Gly Gln Arg Gln Leu Thr
    450                 455                 460

Val Ser Ala Ala Ala Gly Gly Ser Gly Gly Ser Gly Gly Ser Asp Ala
465                 470                 475                 480

Leu Asp Asp Phe Asp Leu Asp Met Leu Gly Ser Asp Ala Leu Asp Asp
                485                 490                 495

Phe Asp Leu Asp Met Leu Gly Ser Asp Ala Leu Asp Asp Phe Asp Leu
            500                 505                 510

Asp Met Leu Gly Ser Asp Ala Leu Asp Asp Phe Asp Leu Asp Met Leu
        515                 520                 525

Gly Ser
    530

<210> SEQ ID NO 8
<211> LENGTH: 699
<212> TYPE: PRT

<213> ORGANISM: Artificial sequence
<220> FEATURE:
<223> OTHER INFORMATION: Synthetic construct

<400> SEQUENCE: 8

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Met
            20                  25                  30

Ala Asp Val Gln Leu Val Glu Ser Gly Gly Leu Val Gln Ala Gly
        35                  40                  45

Gly Ser Leu Arg Leu Ser Cys Ala Ala Ser Gly Arg Thr Ile Ser Met
    50                  55                  60

Ala Ala Met Ser Trp Phe Arg Gln Ala Pro Gly Lys Glu Arg Glu Phe
65              70                  75                  80

Val Ala Gly Ile Ser Arg Ser Ala Gly Ser Ala Val His Ala Asp Ser
                85                  90                  95

Val Lys Gly Arg Phe Thr Ile Ser Arg Asp Asn Thr Lys Asn Thr Leu
            100                 105                 110

Tyr Leu Gln Met Asn Ser Leu Lys Ala Glu Asp Thr Ala Val Tyr Tyr
        115                 120                 125

Cys Ala Val Arg Thr Ser Gly Phe Phe Gly Ser Ile Pro Arg Thr Gly
130                 135                 140

Thr Ala Phe Asp Tyr Trp Gly Gln Gly Thr Gln Val Thr Val Ser Ile
145                 150                 155                 160

Leu Asp Tyr Ser Phe Gly Gly Gly Ala Gly Arg Asp Ile Pro Pro Pro
                165                 170                 175

Leu Ile Glu Glu Thr Val Glu Pro Pro Pro Ala Gln Leu His Phe
            180                 185                 190

Met Tyr Val Ala Ala Ala Phe Val Leu Leu Phe Phe Val Gly Cys
        195                 200                 205

Gly Val Leu Leu Ser Arg Lys Arg Arg Arg Met Lys Leu Leu Ser Ser
210                 215                 220

Ile Glu Gln Ala Cys Asp Ile Cys Arg Leu Lys Lys Leu Lys Cys Ser
225                 230                 235                 240

Lys Glu Lys Pro Lys Cys Ala Lys Cys Leu Lys Asn Asn Trp Glu Cys
                245                 250                 255

Arg Tyr Ser Pro Lys Thr Lys Arg Ser Pro Leu Thr Arg Ala His Leu
            260                 265                 270

Thr Glu Val Glu Ser Arg Leu Glu Arg Leu Glu Gln Leu Phe Leu Leu
        275                 280                 285

Ile Phe Pro Arg Glu Asp Leu Asp Met Ile Leu Lys Met Asp Ser Leu
290                 295                 300

Gln Asp Ile Lys Ala Leu Leu Thr Gly Leu Phe Val Gln Asp Asn Val
305                 310                 315                 320

Asn Lys Asp Ala Val Thr Asp Arg Leu Ala Ser Val Glu Thr Asp Met
                325                 330                 335

Pro Leu Thr Leu Arg Gln His Arg Ile Ser Ala Thr Ser Ser Ser Glu
            340                 345                 350

Glu Ser Ser Asn Lys Gly Gln Arg Gln Leu Thr Val Ser Ala Ala Ala
        355                 360                 365

Gly Gly Ser Gly Gly Ser Gly Gly Ser Asp Ala Leu Asp Asp Phe Asp
370                 375                 380

Leu Asp Met Leu Gly Ser Asp Ala Leu Asp Asp Phe Asp Leu Asp Met

```
                385                 390                 395                 400
Leu Gly Ser Asp Ala Leu Asp Asp Phe Asp Leu Asp Met Leu Gly Ser
                    405                 410                 415
Asp Ala Leu Asp Asp Phe Asp Leu Asp Met Leu Gly Ser Ile Leu Asp
                420                 425                 430
Tyr Ser Phe Gly Gly Gly Ala Gly Arg Asp Ile Pro Pro Pro Leu Ile
            435                 440                 445
Glu Glu Thr Val Glu Pro Pro Pro Ala Gln Leu His Phe Met Tyr
        450                 455                 460
Val Ala Ala Ala Ala Phe Val Leu Leu Phe Phe Val Gly Cys Gly Val
465                 470                 475                 480
Leu Leu Ser Arg Lys Arg Arg Met Lys Leu Leu Ser Ser Ile Glu
                485                 490                 495
Gln Ala Cys Asp Ile Cys Arg Leu Lys Lys Leu Lys Cys Ser Lys Glu
            500                 505                 510
Lys Pro Lys Cys Ala Lys Cys Leu Lys Asn Asn Trp Glu Cys Arg Tyr
        515                 520                 525
Ser Pro Lys Thr Lys Arg Ser Pro Leu Thr Arg Ala His Leu Thr Glu
    530                 535                 540
Val Glu Ser Arg Leu Glu Arg Leu Glu Gln Leu Phe Leu Leu Ile Phe
545                 550                 555                 560
Pro Arg Glu Asp Leu Asp Met Ile Leu Lys Met Asp Ser Leu Gln Asp
                565                 570                 575
Ile Lys Ala Leu Leu Thr Gly Leu Phe Val Gln Asp Asn Val Asn Lys
            580                 585                 590
Asp Ala Val Thr Asp Arg Leu Ala Ser Val Glu Thr Asp Met Pro Leu
        595                 600                 605
Thr Leu Arg Gln His Arg Ile Ser Ala Thr Ser Ser Glu Glu Ser
    610                 615                 620
Ser Asn Lys Gly Gln Arg Gln Leu Thr Val Ser Ala Ala Ala Gly Gly
625                 630                 635                 640
Ser Gly Gly Ser Gly Gly Ser Asp Ala Leu Asp Asp Phe Asp Leu Asp
                645                 650                 655
Met Leu Gly Ser Asp Ala Leu Asp Asp Phe Asp Leu Asp Met Leu Gly
            660                 665                 670
Ser Asp Ala Leu Asp Asp Phe Asp Leu Asp Met Leu Gly Ser Asp Ala
        675                 680                 685
Leu Asp Asp Phe Asp Leu Asp Met Leu Gly Ser
    690                 695

<210> SEQ ID NO 9
<211> LENGTH: 520
<212> TYPE: PRT
<213> ORGANISM: Artificial sequence
<220> FEATURE:
<223> OTHER INFORMATION: Synthetic construct

<400> SEQUENCE: 9

Met Ala Leu Pro Val Thr Ala Leu Leu Leu Pro Leu Ala Leu Leu Leu
1               5                   10                  15
His Ala Ala Arg Pro Glu Gln Lys Leu Ile Ser Glu Glu Asp Leu Asp
                20                  25                  30
Ile Gln Met Thr Gln Thr Thr Ser Ser Leu Ser Ala Ser Leu Gly Asp
            35                  40                  45
Arg Val Thr Ile Ser Cys Arg Ala Ser Gln Asp Ile Ser Lys Tyr Leu
```

```
                50              55              60
Asn Trp Tyr Gln Gln Lys Pro Asp Gly Thr Val Lys Leu Leu Ile Tyr
 65                      70                  75                  80

His Thr Ser Arg Leu His Ser Gly Val Pro Ser Arg Phe Ser Gly Ser
                         85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
                115                 120                 125

Phe Gly Gly Gly Thr Lys Leu Glu Ile Thr Gly Gly Gly Gly Ser Gly
                130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
                195                 200                 205

Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
                260                 265                 270

Ser Glu Pro Pro Pro Ala Gln Leu His Phe Met Tyr Val Ala Ala
                275                 280                 285

Ala Ala Phe Val Leu Leu Phe Phe Val Gly Cys Gly Val Leu Leu Ser
                290                 295                 300

Arg Lys Arg Arg Arg Met Lys Leu Leu Ser Ser Ile Glu Gln Ala Cys
305                 310                 315                 320

Asp Ile Cys Arg Leu Lys Lys Leu Lys Cys Ser Lys Glu Lys Pro Lys
                325                 330                 335

Cys Ala Lys Cys Leu Lys Asn Asn Trp Glu Cys Arg Tyr Ser Pro Lys
                340                 345                 350

Thr Lys Arg Ser Pro Leu Thr Arg Ala His Leu Thr Glu Val Glu Ser
                355                 360                 365

Arg Leu Glu Arg Leu Glu Gln Leu Phe Leu Leu Ile Phe Pro Arg Glu
370                 375                 380

Asp Leu Asp Met Ile Leu Lys Met Asp Ser Leu Gln Asp Ile Lys Ala
385                 390                 395                 400

Leu Leu Thr Gly Leu Phe Val Gln Asp Asn Val Asn Lys Asp Ala Val
                405                 410                 415

Thr Asp Arg Leu Ala Ser Val Glu Thr Asp Met Pro Leu Thr Leu Arg
                420                 425                 430

Gln His Arg Ile Ser Ala Thr Ser Ser Ser Glu Glu Ser Ser Asn Lys
                435                 440                 445

Gly Gln Arg Gln Leu Thr Val Ser Ala Ala Gly Gly Ser Gly Gly
                450                 455                 460

Ser Gly Gly Ser Asp Ala Leu Asp Asp Phe Asp Leu Asp Met Leu Gly
465                 470                 475                 480
```

```
Ser Asp Ala Leu Asp Asp Phe Asp Leu Asp Met Leu Gly Ser Asp Ala
            485                 490                 495

Leu Asp Asp Phe Asp Leu Asp Met Leu Gly Ser Asp Ala Leu Asp Asp
        500                 505                 510

Phe Asp Leu Asp Met Leu Gly Ser
        515                 520

<210> SEQ ID NO 10
<211> LENGTH: 273
<212> TYPE: PRT
<213> ORGANISM: Artificial sequence
<220> FEATURE:
<223> OTHER INFORMATION: Synthetic construct

<400> SEQUENCE: 10

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
            260                 265                 270

Ser

<210> SEQ ID NO 11
<211> LENGTH: 273
<212> TYPE: PRT
<213> ORGANISM: Artificial sequence
<220> FEATURE:
```

<223> OTHER INFORMATION: Synthetic construct

<400> SEQUENCE: 11

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser

<210> SEQ ID NO 12
<211> LENGTH: 273
<212> TYPE: PRT
<213> ORGANISM: Artificial sequence
<220> FEATURE:
<223> OTHER INFORMATION: Synthetic construct

<400> SEQUENCE: 12

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
130                 135                 140

Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser

<210> SEQ ID NO 13
<211> LENGTH: 273
<212> TYPE: PRT
<213> ORGANISM: Artificial sequence
<220> FEATURE:
<223> OTHER INFORMATION: Synthetic construct

<400> SEQUENCE: 13

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
130                 135                 140

Gly Gly Gly Ser Gly Gly Gly Gly Ser Glu Val Lys Leu Gln Glu Ser

```
            145                 150                 155                 160
Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
                195                 200                 205

Thr Thr Tyr Tyr Asn Ser Ala Leu Lys Ser Arg Leu Thr Ile Ile Lys
                210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
                260                 265                 270

Ser

<210> SEQ ID NO 14
<211> LENGTH: 273
<212> TYPE: PRT
<213> ORGANISM: Artificial sequence
<220> FEATURE:
<223> OTHER INFORMATION: Synthetic construct

<400> SEQUENCE: 14

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
                35                  40                  45

Arg Val Thr Ile Ser Cys Arg Ala Ser Gln Asp Ile Ser Lys Tyr Leu
            50                  55                  60

Asn Trp Tyr Gln Gln Lys Pro Asp Gly Thr Val Lys Leu Leu Ile Tyr
65              70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
                115                 120                 125

Phe Gly Gly Gly Thr Lys Leu Glu Ile Thr Gly Gly Gly Gly Ser Gly
            130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
                195                 200                 205

Thr Thr Tyr Tyr Asn Ser Ala Leu Lys Ser Arg Leu Thr Ile Ile Lys
                210                 215                 220

Asp Asn Ser Lys Ser Gln Val Phe Leu Lys Met Asn Ser Leu Gln Thr
225                 230                 235                 240
```

```
Asp Asp Thr Ala Ile Tyr Tyr Cys Ala Lys His Tyr Tyr Gly Gly
            245                 250                 255

Ser Tyr Ala Met Asp Tyr Trp Gly Gln Gly Thr Ser Val Thr Val Ser
            260                 265                 270

Ser

<210> SEQ ID NO 15
<211> LENGTH: 273
<212> TYPE: PRT
<213> ORGANISM: Artificial sequence
<220> FEATURE:
<223> OTHER INFORMATION: Synthetic construct

<400> SEQUENCE: 15

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Gly Gly
                245                 250                 255

Ser Tyr Ala Met Asp Tyr Trp Gly Gln Gly Thr Ser Val Thr Val Ser
            260                 265                 270

Ser

<210> SEQ ID NO 16
<211> LENGTH: 273
<212> TYPE: PRT
<213> ORGANISM: Artificial sequence
<220> FEATURE:
<223> OTHER INFORMATION: Synthetic construct
```

<400> SEQUENCE: 16

```
Met Ala Leu Pro Val Thr Ala Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65              70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
            210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser
```

<210> SEQ ID NO 17
<211> LENGTH: 429
<212> TYPE: PRT
<213> ORGANISM: Artificial sequence
<220> FEATURE:
<223> OTHER INFORMATION: Synthetic construct

<400> SEQUENCE: 17

```
Met Ala Leu Pro Val Thr Ala Leu Leu Pro Leu Ala Leu Leu Leu
1               5                   10                  15

His Ala Ala Arg Pro Glu Gln Lys Leu Ile Ser Glu Glu Asp Leu Met
            20                  25                  30

Ala Asp Val Gln Leu Val Glu Ser Gly Gly Gly Leu Val Gln Ala Gly
            35                  40                  45

Gly Ser Leu Arg Leu Ser Cys Ala Ala Ser Gly Arg Thr Ile Ser Met
    50                  55                  60

Ala Ala Met Ser Trp Phe Arg Gln Ala Pro Gly Lys Glu Arg Glu Phe
```

```
            65                  70                  75                  80
Val Ala Gly Ile Ser Arg Ser Ala Gly Ser Ala Val His Ala Asp Ser
                85                  90                  95

Val Lys Gly Arg Phe Thr Ile Ser Arg Asp Asn Thr Lys Asn Thr Leu
            100                 105                 110

Tyr Leu Gln Met Asn Ser Leu Lys Ala Glu Asp Thr Ala Val Tyr Tyr
            115                 120                 125

Cys Ala Val Arg Thr Ser Gly Phe Phe Gly Ser Ile Pro Arg Thr Gly
            130                 135                 140

Thr Ala Phe Asp Tyr Trp Gly Gln Gly Thr Gln Val Thr Val Ser Ile
145                 150                 155                 160

Leu Asp Tyr Ser Phe Gly Gly Ala Gly Arg Asp Ile Pro Pro Pro
                165                 170                 175

Leu Ile Glu Glu Thr Val Glu Pro Pro Pro Ala Gln Leu His Phe
                180                 185                 190

Met Tyr Val Ala Ala Ala Phe Val Leu Leu Phe Phe Val Gly Cys
                195                 200                 205

Gly Val Leu Leu Ser Arg Lys Arg Arg Arg Met Lys Leu Leu Ser Ser
            210                 215                 220

Ile Glu Gln Ala Cys Asp Ile Cys Arg Leu Lys Lys Leu Lys Cys Ser
225                 230                 235                 240

Lys Glu Lys Pro Lys Cys Ala Lys Cys Leu Lys Asn Asn Trp Glu Cys
                245                 250                 255

Arg Tyr Ser Pro Lys Thr Lys Arg Ser Pro Leu Thr Arg Ala His Leu
            260                 265                 270

Thr Glu Val Glu Ser Arg Leu Glu Arg Leu Glu Gln Leu Phe Leu Leu
            275                 280                 285

Ile Phe Pro Arg Glu Asp Leu Asp Met Ile Leu Lys Met Asp Ser Leu
            290                 295                 300

Gln Asp Ile Lys Ala Leu Leu Thr Gly Leu Phe Val Gln Asp Asn Val
305                 310                 315                 320

Asn Lys Asp Ala Val Thr Asp Arg Leu Ala Ser Val Glu Thr Asp Met
                325                 330                 335

Pro Leu Thr Leu Arg Gln His Arg Ile Ser Ala Thr Ser Ser Ser Glu
            340                 345                 350

Glu Ser Ser Asn Lys Gly Gln Arg Gln Leu Thr Val Ser Ala Ala Ala
            355                 360                 365

Gly Gly Ser Gly Gly Ser Gly Gly Ser Asp Ala Leu Asp Asp Phe Asp
            370                 375                 380

Leu Asp Met Leu Gly Ser Asp Ala Leu Asp Asp Phe Asp Leu Asp Met
385                 390                 395                 400

Leu Gly Ser Asp Ala Leu Asp Asp Phe Asp Leu Asp Met Leu Gly Ser
                405                 410                 415

Asp Ala Leu Asp Asp Phe Asp Leu Asp Met Leu Gly Ser
            420                 425

<210> SEQ ID NO 18
<211> LENGTH: 273
<212> TYPE: PRT
<213> ORGANISM: Artificial sequence
<220> FEATURE:
<223> OTHER INFORMATION: Synthetic construct

<400> SEQUENCE: 18

Met Ala Leu Pro Val Thr Ala Leu Leu Leu Pro Leu Ala Leu Leu Leu
```

-continued

```
          1               5                  10                 15
        His Ala Ala Arg Pro Glu Gln Lys Leu Ile Ser Glu Glu Asp Leu Asp
                        20                  25                 30

Ile Gln Met Thr Gln Thr Thr Ser Ser Leu Ser Ala Ser Leu Gly Asp
                        35                  40                 45

Arg Val Thr Ile Ser Cys Arg Ala Ser Gln Asp Ile Ser Lys Tyr Leu
                    50                  55                 60

Asn Trp Tyr Gln Gln Lys Pro Asp Gly Thr Val Lys Leu Leu Ile Tyr
         65                 70                  75                 80

His Thr Ser Arg Leu His Ser Gly Val Pro Ser Arg Phe Ser Gly Ser
                            85                  90                 95

Gly Ser Gly Thr Asp Tyr Ser Leu Thr Ile Ser Asn Leu Glu Gln Glu
                       100                 105                110

Asp Ile Ala Thr Tyr Phe Cys Gln Gln Gly Asn Thr Leu Pro Tyr Thr
                       115                 120                125

Phe Gly Gly Gly Thr Lys Leu Glu Ile Thr Gly Gly Gly Gly Ser Gly
                   130                 135                140

Gly Gly Gly Ser Gly Gly Gly Ser Glu Val Lys Leu Gln Glu Ser
        145                 150                 155                160

Gly Pro Gly Leu Val Ala Pro Ser Gln Ser Leu Ser Val Thr Cys Thr
                        165                 170                175

Val Ser Gly Val Ser Leu Pro Asp Tyr Gly Val Ser Trp Ile Arg Gln
                        180                 185                190

Pro Pro Arg Lys Gly Leu Glu Trp Leu Gly Val Ile Trp Gly Ser Glu
                        195                 200                205

Thr Thr Tyr Tyr Asn Ser Ala Leu Lys Ser Arg Leu Thr Ile Ile Lys
                        210                 215                220

Asp Asn Ser Lys Ser Gln Val Phe Leu Lys Met Asn Ser Leu Gln Thr
        225                 230                 235                240

Asp Asp Thr Ala Ile Tyr Tyr Cys Ala Lys His Tyr Tyr Gly Gly
                        245                 250                255

Ser Tyr Ala Met Asp Tyr Trp Gly Gln Gly Thr Ser Val Thr Val Ser
                        260                 265                270

Ser
```

<210> SEQ ID NO 19
<211> LENGTH: 32
<212> TYPE: PRT
<213> ORGANISM: Artificial sequence
<220> FEATURE:
<223> OTHER INFORMATION: Synthetic construct

<400> SEQUENCE: 19

```
        Ile Leu Asp Tyr Ser Phe Gly Gly Gly Ala Gly Arg Asp Ile Pro Pro
         1               5                  10                 15

Pro Leu Ile Glu Glu Thr Val Glu Pro Pro Pro Ala Gln Leu His
                        20                  25                 30
```

<210> SEQ ID NO 20
<211> LENGTH: 24
<212> TYPE: PRT
<213> ORGANISM: Artificial sequence
<220> FEATURE:
<223> OTHER INFORMATION: Synthetic construct

<400> SEQUENCE: 20

Ala Pro Ala Ala Ala Pro Glu Val Ser Glu Glu Pro Arg Pro Leu Glu

```
1               5                   10                  15
Pro Pro Glu Pro Ser Val Pro Leu
            20

<210> SEQ ID NO 21
<211> LENGTH: 20
<212> TYPE: PRT
<213> ORGANISM: Artificial sequence
<220> FEATURE:
<223> OTHER INFORMATION: Synthetic construct

<400> SEQUENCE: 21

Leu Tyr Thr Ala Pro Pro Ser Thr Pro Pro Ala Thr Ser Leu Thr Pro
1               5                   10                  15

Glu Arg Thr Gln
            20

<210> SEQ ID NO 22
<211> LENGTH: 16
<212> TYPE: PRT
<213> ORGANISM: Artificial sequence
<220> FEATURE:
<223> OTHER INFORMATION: Synthetic construct

<400> SEQUENCE: 22

Val His Pro His Ala Gly Thr Ala Pro Pro Ala Asn Gln Leu Pro Trp
1               5                   10                  15

<210> SEQ ID NO 23
<211> LENGTH: 32
<212> TYPE: PRT
<213> ORGANISM: Artificial sequence
<220> FEATURE:
<223> OTHER INFORMATION: Synthetic construct

<400> SEQUENCE: 23

Ile Leu Asp Tyr Ser Phe Gly Gly Gly Ala Gly Arg Asp Ile Pro Pro
1               5                   10                  15

Pro Leu Ile Glu Glu Thr Val Glu Pro Pro Pro Ala Gln Leu His
            20                  25                  30

<210> SEQ ID NO 24
<211> LENGTH: 20
<212> TYPE: PRT
<213> ORGANISM: Artificial sequence
<220> FEATURE:
<223> OTHER INFORMATION: Synthetic construct

<400> SEQUENCE: 24

Leu Tyr Thr Ala Pro Pro Ser Thr Pro Pro Ala Thr Ser Leu Thr Pro
1               5                   10                  15

Glu Arg Thr Gln
            20

<210> SEQ ID NO 25
<211> LENGTH: 16
<212> TYPE: PRT
<213> ORGANISM: Artificial sequence
<220> FEATURE:
<223> OTHER INFORMATION: Synthetic construct

<400> SEQUENCE: 25

Val His Pro His Ala Gly Thr Ala Pro Pro Ala Asn Gln Leu Pro Trp
1               5                   10                  15
```

<210> SEQ ID NO 26
<211> LENGTH: 32
<212> TYPE: PRT
<213> ORGANISM: Artificial sequence
<220> FEATURE:
<223> OTHER INFORMATION: Synthetic construct

<400> SEQUENCE: 26

Ile Leu Asp Tyr Ser Phe Gly Gly Gly Ala Gly Arg Asp Ile Pro Pro
1               5                   10                  15

Pro Leu Ile Glu Glu Thr Val Glu Pro Pro Pro Ala Gln Leu His
            20                  25                  30

<210> SEQ ID NO 27
<211> LENGTH: 9
<212> TYPE: PRT
<213> ORGANISM: Artificial sequence
<220> FEATURE:
<223> OTHER INFORMATION: Synthetic construct

<400> SEQUENCE: 27

Glu Pro Pro Pro Pro Ala Gln Leu His
1               5

<210> SEQ ID NO 28
<211> LENGTH: 22
<212> TYPE: PRT
<213> ORGANISM: Artificial sequence
<220> FEATURE:
<223> OTHER INFORMATION: Synthetic construct

<400> SEQUENCE: 28

Phe Met Tyr Val Ala Ala Ala Ala Phe Val Leu Leu Phe Phe Val Gly
1               5                   10                  15

Cys Gly Val Leu Leu Ser
            20

<210> SEQ ID NO 29
<211> LENGTH: 22
<212> TYPE: PRT
<213> ORGANISM: Artificial sequence
<220> FEATURE:
<223> OTHER INFORMATION: Synthetic construct

<400> SEQUENCE: 29

Leu Pro Leu Leu Val Ala Gly Ala Val Leu Leu Val Ile Leu Val
1               5                   10                  15

Leu Gly Val Met Val Ala
            20

<210> SEQ ID NO 30
<211> LENGTH: 23
<212> TYPE: PRT
<213> ORGANISM: Artificial sequence
<220> FEATURE:
<223> OTHER INFORMATION: Synthetic construct

<400> SEQUENCE: 30

Leu Leu Tyr Leu Leu Ala Val Ala Val Ile Ile Leu Phe Ile Ile
1               5                   10                  15

Leu Leu Gly Val Ile Met Ala
            20

<210> SEQ ID NO 31

```
<211> LENGTH: 24
<212> TYPE: PRT
<213> ORGANISM: Artificial sequence
<220> FEATURE:
<223> OTHER INFORMATION: Synthetic construct

<400> SEQUENCE: 31

Pro Val Leu Cys Ser Pro Val Ala Gly Val Ile Leu Leu Ala Leu Gly
1               5                   10                  15

Ala Leu Leu Val Leu Gln Leu Ile
            20

<210> SEQ ID NO 32
<211> LENGTH: 22
<212> TYPE: PRT
<213> ORGANISM: Artificial sequence
<220> FEATURE:
<223> OTHER INFORMATION: Synthetic construct

<400> SEQUENCE: 32

Phe Met Tyr Val Ala Ala Ala Ala Phe Val Leu Leu Phe Phe Val Gly
1               5                   10                  15

Cys Gly Val Leu Leu Ser
            20

<210> SEQ ID NO 33
<211> LENGTH: 23
<212> TYPE: PRT
<213> ORGANISM: Artificial sequence
<220> FEATURE:
<223> OTHER INFORMATION: Synthetic construct

<400> SEQUENCE: 33

Leu Leu Tyr Leu Leu Ala Val Ala Val Val Ile Ile Leu Phe Ile Ile
1               5                   10                  15

Leu Leu Gly Val Ile Met Ala
            20

<210> SEQ ID NO 34
<211> LENGTH: 24
<212> TYPE: PRT
<213> ORGANISM: Artificial sequence
<220> FEATURE:
<223> OTHER INFORMATION: Synthetic construct

<400> SEQUENCE: 34

Pro Val Leu Cys Ser Pro Val Ala Gly Val Ile Leu Leu Ala Leu Gly
1               5                   10                  15

Ala Leu Leu Val Leu Gln Leu Ile
            20

<210> SEQ ID NO 35
<211> LENGTH: 22
<212> TYPE: PRT
<213> ORGANISM: Artificial sequence
<220> FEATURE:
<223> OTHER INFORMATION: Synthetic construct

<400> SEQUENCE: 35

Phe Met Tyr Val Ala Ala Ala Ala Phe Val Leu Leu Phe Phe Val Gly
1               5                   10                  15

Cys Gly Val Leu Leu Ser
            20
```

```
<210> SEQ ID NO 36
<211> LENGTH: 22
<212> TYPE: PRT
<213> ORGANISM: Artificial sequence
<220> FEATURE:
<223> OTHER INFORMATION: Synthetic construct

<400> SEQUENCE: 36

Phe Met Tyr Val Ala Ala Ala Ala Phe Val Leu Leu Phe Phe Val Gly
1               5                   10                  15

Cys Gly Val Leu Leu Ser
            20

<210> SEQ ID NO 37
<211> LENGTH: 5
<212> TYPE: PRT
<213> ORGANISM: Artificial sequence
<220> FEATURE:
<223> OTHER INFORMATION: Synthetic construct

<400> SEQUENCE: 37

Arg Lys Arg Arg Arg
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic construct

<400> SEQUENCE: 38

Arg Arg Lys Arg Glu His
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic construct

<400> SEQUENCE: 39

Lys Arg Lys Arg Lys His
1               5

<210> SEQ ID NO 40
<211> LENGTH: 7
<212> TYPE: PRT
<213> ORGANISM: Artificial sequence
<220> FEATURE:
<223> OTHER INFORMATION: Synthetic construct

<400> SEQUENCE: 40

Arg Arg Arg Arg Arg Glu His
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic construct

<400> SEQUENCE: 41

Lys Arg Lys Arg Lys His
1               5
```

<210> SEQ ID NO 42
<211> LENGTH: 5
<212> TYPE: PRT
<213> ORGANISM: Artificial sequence
<220> FEATURE:
<223> OTHER INFORMATION: Synthetic construct

<400> SEQUENCE: 42

Arg Lys Arg Arg Arg
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic construct

<400> SEQUENCE: 43

Lys Arg Lys Arg Lys His
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic construct

<400> SEQUENCE: 44

Arg Lys Arg Arg Arg
1               5

<210> SEQ ID NO 45
<211> LENGTH: 5
<212> TYPE: PRT
<213> ORGANISM: Artificial sequence
<220> FEATURE:
<223> OTHER INFORMATION: Synthetic construct

<400> SEQUENCE: 45

Arg Lys Arg Arg Arg
1               5

<210> SEQ ID NO 46
<211> LENGTH: 211
<212> TYPE: PRT
<213> ORGANISM: Artificial sequence
<220> FEATURE:
<223> OTHER INFORMATION: Synthetic construct

<400> SEQUENCE: 46

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu

```
            85                  90                  95
Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
            130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
                195                 200                 205

Leu Gly Ser
            210

<210> SEQ ID NO 47
<211> LENGTH: 211
<212> TYPE: PRT
<213> ORGANISM: Artificial sequence
<220> FEATURE:
<223> OTHER INFORMATION: Synthetic construct

<400> SEQUENCE: 47

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
            50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
            130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
                195                 200                 205

Leu Gly Ser
            210
```

<210> SEQ ID NO 48
<211> LENGTH: 211
<212> TYPE: PRT
<213> ORGANISM: Artificial sequence
<220> FEATURE:
<223> OTHER INFORMATION: Synthetic construct

<400> SEQUENCE: 48

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ala Ala Gly Gly Ser Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
            180                 185                 190

Leu Asp Met Leu Gly Ser Asp Ala Leu Asp Asp Phe Asp Leu Asp Met
        195                 200                 205

Leu Gly Ser
    210
```

<210> SEQ ID NO 49
<211> LENGTH: 211
<212> TYPE: PRT
<213> ORGANISM: Artificial sequence
<220> FEATURE:
<223> OTHER INFORMATION: Synthetic construct

<400> SEQUENCE: 49

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95
```

```
Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
            130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                    165                 170                 175

Asp Phe Asp Leu Asp Met Leu Gly Ser Asp Ala Leu Asp Phe Asp
                    180                 185                 190

Leu Asp Met Leu Gly Ser Asp Ala Leu Asp Asp Phe Asp Leu Asp Met
            195                 200                 205

Leu Gly Ser
            210

<210> SEQ ID NO 50
<211> LENGTH: 211
<212> TYPE: PRT
<213> ORGANISM: Artificial sequence
<220> FEATURE:
<223> OTHER INFORMATION: Synthetic construct

<400> SEQUENCE: 50

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
            130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                    165                 170                 175

Asp Phe Asp Leu Asp Met Leu Gly Ser Asp Ala Leu Asp Phe Asp
                    180                 185                 190

Leu Asp Met Leu Gly Ser Asp Ala Leu Asp Asp Phe Asp Leu Asp Met
            195                 200                 205

Leu Gly Ser
            210

<210> SEQ ID NO 51
<211> LENGTH: 211
```

```
<212> TYPE: PRT
<213> ORGANISM: Artificial sequence
<220> FEATURE:
<223> OTHER INFORMATION: Synthetic construct

<400> SEQUENCE: 51
```

| | | | | | | | | | | | | | | |
|---|---|---|---|---|---|---|---|---|---|---|---|---|---|---|
| Met | Lys | Leu | Leu | Ser | Ser | Ile | Glu | Gln | Ala | Cys | Asp | Ile | Cys | Arg | Leu |
| 1 | | | | 5 | | | | | 10 | | | | | 15 |

Met Lys Leu Leu Ser Ser Ile Glu Gln Ala Cys Asp Ile Cys Arg Leu
1               5                  10                 15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
            180                 185                 190

Leu Asp Met Leu Gly Ser Asp Ala Leu Asp Asp Phe Asp Leu Asp Met
            195                 200                 205

Leu Gly Ser
        210

```
<210> SEQ ID NO 52
<211> LENGTH: 211
<212> TYPE: PRT
<213> ORGANISM: Artificial sequence
<220> FEATURE:
<223> OTHER INFORMATION: Synthetic construct

<400> SEQUENCE: 52
```

Met Lys Leu Leu Ser Ser Ile Glu Gln Ala Cys Asp Ile Cys Arg Leu
1               5                  10                 15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
                195                 200                 205

Leu Gly Ser
        210

<210> SEQ ID NO 53
<211> LENGTH: 211
<212> TYPE: PRT
<213> ORGANISM: Artificial sequence
<220> FEATURE:
<223> OTHER INFORMATION: Synthetic construct

<400> SEQUENCE: 53

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ala Ala Ala Gly Gly Ser Gly Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
                195                 200                 205

Leu Gly Ser
        210

<210> SEQ ID NO 54
<211> LENGTH: 211
<212> TYPE: PRT
<213> ORGANISM: Artificial sequence
<220> FEATURE:
<223> OTHER INFORMATION: Synthetic construct

<400> SEQUENCE: 54

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Glu Ser Ser Asn Lys Gly Gln Arg Gln Leu
        130                 135                 140

Thr Val Ser Ala Ala Gly Gly Ser Gly Ser Gly Gly Ser Asp
145                 150                 155                 160

Ala Leu Asp Asp Phe Asp Leu Asp Met Leu Gly Ser Asp Ala Leu Asp
                165                 170                 175

Asp Phe Asp Leu Asp Met Leu Gly Ser Asp Ala Leu Asp Asp Phe Asp
                180                 185                 190

Leu Asp Met Leu Gly Ser Asp Ala Leu Asp Asp Phe Asp Leu Asp Met
        195                 200                 205

Leu Gly Ser
    210
```

<210> SEQ ID NO 55
<211> LENGTH: 21
<212> TYPE: PRT
<213> ORGANISM: Artificial sequence
<220> FEATURE:
<223> OTHER INFORMATION: Synthetic construct

<400> SEQUENCE: 55

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 56
<211> LENGTH: 10
<212> TYPE: PRT
<213> ORGANISM: Artificial sequence
<220> FEATURE:
<223> OTHER INFORMATION: Synthetic construct

<400> SEQUENCE: 56

```
Glu Gln Lys Leu Ile Ser Glu Glu Asp Leu
1               5                   10
```

<210> SEQ ID NO 57
<211> LENGTH: 20

```
<212> TYPE: DNA
<213> ORGANISM: Artificial sequence
<220> FEATURE:
<223> OTHER INFORMATION: Synthetic construct

<400> SEQUENCE: 57
ggagcactgt cctccgaacg                                                    20

<210> SEQ ID NO 58
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(3)
<223> OTHER INFORMATION: X can be any amino acid residue
<220> FEATURE:
<221> NAME/KEY: MISC_FEATURE
<222> LOCATION: (4)..(4)
<223> OTHER INFORMATION: X represents a hydrophobic residue such as Leu,
      Ile, Val, Phe, Trp, Tyr, Val, Met, and Pro

<400> SEQUENCE: 58

Pro Xaa Xaa Xaa
1

<210> SEQ ID NO 59
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(3)
<223> OTHER INFORMATION: X can be any amino acid residue
<220> FEATURE:
<221> NAME/KEY: MISC_FEATURE
<222> LOCATION: (4)..(4)
<223> OTHER INFORMATION: X represents a hydrophobic residue such as Leu,
      Ile, Val, Phe, Trp, Tyr, Val, Met, and Pro
<220> FEATURE:
<221> NAME/KEY: MISC_FEATURE
<222> LOCATION: (5)..(5)
<223> OTHER INFORMATION: X is either Ser or Thr

<400> SEQUENCE: 59

Pro Xaa Xaa Xaa Xaa
1               5

<210> SEQ ID NO 60
<211> LENGTH: 6
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is either Leu or Gln

<400> SEQUENCE: 60

Pro Xaa Gly Met Thr Ser
1               5

<210> SEQ ID NO 61
<211> LENGTH: 5
<212> TYPE: PRT
<213> ORGANISM: Artificial sequence
```

```
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X is either Leu or Gln

<400> SEQUENCE: 61

Pro Xaa Gly Met Thr
1               5

<210> SEQ ID NO 62
<211> LENGTH: 3
<212> TYPE: PRT
<213> ORGANISM: Artificial sequence
<220> FEATURE:
<223> OTHER INFORMATION: Synthetic construct

<400> SEQUENCE: 62

Val Gly Arg
1

<210> SEQ ID NO 63
<211> LENGTH: 7
<212> TYPE: PRT
<213> ORGANISM: Artificial sequence
<220> FEATURE:
<223> OTHER INFORMATION: Synthetic construct

<400> SEQUENCE: 63

Glu Asn Leu Tyr Thr Gln Ser
1               5

<210> SEQ ID NO 64
<211> LENGTH: 5
<212> TYPE: PRT
<213> ORGANISM: Artificial sequence
<220> FEATURE:
<223> OTHER INFORMATION: Synthetic construct

<400> SEQUENCE: 64

Asp Asp Asp Asp Lys
1               5

<210> SEQ ID NO 65
<211> LENGTH: 4
<212> TYPE: PRT
<213> ORGANISM: Artificial sequence
<220> FEATURE:
<223> OTHER INFORMATION: Synthetic construct

<400> SEQUENCE: 65

Leu Val Pro Arg
1
```